(12) United States Patent
Obika et al.

(10) Patent No.: US 8,541,562 B2
(45) Date of Patent: Sep. 24, 2013

(54) BRIDGED ARTIFICIAL NUCLEOSIDE AND NUCLEOTIDE

(75) Inventors: Satoshi Obika, Osaka (JP); Yoshiyuki Hari, Osaka (JP); Tetsuya Kodama, Osaka (JP); Aiko Yahara, Osaka (JP); Masaru Nishida, Osaka (JM)

(73) Assignee: Osaka University, Osaka (JP)

( * ) Notice: Subject to any disclaimer, the term of this patent is extended or adjusted under 35 U.S.C. 154(b) by 0 days.

(21) Appl. No.: 13/502,611

(22) PCT Filed: Oct. 19, 2010

(86) PCT No.: PCT/JP2010/068409
§ 371 (c)(1),
(2), (4) Date: Apr. 18, 2012

(87) PCT Pub. No.: WO2011/052436
PCT Pub. Date: May 5, 2011

(65) Prior Publication Data
US 2012/0208991 A1    Aug. 16, 2012

(30) Foreign Application Priority Data
Oct. 29, 2009 (JP) ................ 2009-248979
Feb. 4, 2010 (JP) ................ 2010-023209

(51) Int. Cl.
*C07H 21/02* (2006.01)
*C07H 19/00* (2006.01)
*C07H 19/02* (2006.01)

(52) U.S. Cl.
USPC ............ 536/23.1; 536/27.1; 536/28.1

(58) Field of Classification Search
None
See application file for complete search history.

(56) References Cited

U.S. PATENT DOCUMENTS

| | | | |
|---|---|---|---|
| 6,268,490 B1 | 7/2001 | Imanishi et al. | |
| 6,403,566 B1 | 6/2002 | Wang | |
| 7,427,672 B2 | 9/2008 | Imanishi et al. | |
| 7,615,619 B2 | 11/2009 | Imanishi et al. | |

FOREIGN PATENT DOCUMENTS

| | | |
|---|---|---|
| WO | 98/39352 | 9/1998 |
| WO | 99/60855 | 12/1999 |
| WO | 03/068795 | 8/2003 |
| WO | 2005/021570 | 3/2005 |

OTHER PUBLICATIONS

C. Wahlestedt et al., "Potent and nontoxic antisense oligonucleotides containing locked nucleic acids", Proc. Natl. Acad. Sci. USA, 2000, vol. 97, No. 10, pp. 5633-5638.
Y. Hari et al., "Synthesis and properties of 2'-O,4'-C-methyleneoxymethylene bridged nucleic acid", Bioorg. Med. Chem., 2006, vol. 14, pp. 1029-1038.
K. Miyashita et al., "N-Methyl substituted 2',4'-BNA NC: a highly nuclease-resistant nucleic acid analogue with high-affinity RNA selective hybridization", Chem. Commun., 2007, pp. 3765-3767.
S.M.A. Rahman et al., "Design, Synthesis, and Properties of 2',4'-BNC NC: A Bridged Nucleic Acid Analogue", J. Am. Chem. Soc., 2008, vol. 130, No. 14, pp. 4886-4896.
M. Kuwahara et al., "Systematic analysis of enzymatic DNA polymerization using oligo-DNA templates and triphosphate analogs involving 2',4'-bridged nucleosides", Nucleic Acids Res., 2008, vol. 36, No. 13, pp. 4257-4265.
S. Obika et al., "2'-O,4'-C-Methylene Bridged Nucleic Acid (2',4'-BNA): Synthesis and Triplex-Forming Properties", Bioorg. Med. Chem., 2001, vol. 9, pp. 1001-1011.
T. Imanishi, "Overview of 40 Year's Chemical Study", Yakugaku Zasshi, 2009, vol. 129, No. 1, pp. 107-134 and partial English translation.
Proceedings of the 124th Annual Meeting of the Pharmaceutical Society of Japan, 2004, 124(2), 53, 30[P2]I-279, published on Mar. 5, 2004 and partial English translation.
Proceedings of the 129th Annual Meeting of the Pharmaceutical Society of Japan, 2009, 129(2), 60, 26H-pm06, published on Mar. 5, 2009 and partial English translation.
S.K. Singh et al., "LNA (locked nucleic acids): synthesis and high-affinity nucleic acid recognition", Chem. Commun., 1998, pp. 455-456.
A.A. Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition", Tetrahedron, 1998, vol. 54, pp. 3607-3630.
Koji Morita et al., "2'-O,4'-C-Ethylene-Bridged Nucleic Acids (ENA): Highly Nuclease-Resistant and Thermodynamically Stable Oligonucleotides for Antisense Drug", Bioorganic & Medicinal Chemistry Letters, 12(2002), pp. 73-76.
Sanjay K. Singh et al., "Synthesis of Novel Bicyclo [2.2.1] Ribonucleosides: 2'-Amino- and 2'-Thio-LNA Monomeric Nucleosides", J. Org. Chem., 1998, 63, pp. 6078-6079.
Oommen P. Varghese et al, "Conformationally Constrained 2'-N,4'-C-Ethylene-Bridged Thymidine (Aza-ENA-T): Synthesis, Structure, Physical, and Biochemical Studies of Aza-ENA-T-Modified Oligonucleotides", J. Am. Chem. Soc., 2006, 128, pp. 15173-15187.
Yahara, A. et al., Synthesis and properties of a novel 2',4'-BNA bearing a urea bridged structure, Nucleic Acids Symposium Series, Sep. 2009, vol. 53, No. 1, pp. 11-12.

(Continued)

*Primary Examiner* — Traviss C McIntosh, III
(74) *Attorney, Agent, or Firm* — Renner, Otto, Boisselle & Sklar, LLP

(57) ABSTRACT

It is an object of the present invention to provide a novel molecule for antisense therapies which is not susceptible to nuclease degradation in vivo and has a high binding affinity and specificity for the target mRNAs and which can efficiently regulate expression of specific genes. The novel artificial nucleoside of the present invention has an amide bond introduced into a bridge structure of 2',4'-BNA/LNA. The oligonucleotide containing the 2',4'-bridged artificial nucleotide has a binding affinity for a single-stranded RNA comparable to known 2',4'-BNA/LNA and has an increased nuclease resistance over LNA. Particularly, it is expected to be applied to nucleic acid drugs because of its much stronger binding affinity for single-stranded RNAs than S-oligo's affinity.

19 Claims, 1 Drawing Sheet

(56) References Cited

OTHER PUBLICATIONS

Nishida, M. et al., Synthesis and chemical properties of a novel 2',4'-bridged nucleic acid analog with a seven-membered cyclic carbamate structure, Nucleic Acids Symposium Series, 2007, No. 51, pp. 157-158.

PCT/JP2010/068409; International Search Report dated Dec. 1, 2010.

R. Kumar et al.; "The First Analogues of LNA (Locked Nucleic Acids): Phosphorothioate-LNA and 2'-Thio-LNA", Bioorganic & Medicinal Chemistry Letters, 1998, vol. 8, pp. 2219-2222.

Sanjay K. et al.; "Synthesis of 2'-Amino-LNA; A Novel Conformationally Restricted High-Affinity Oligonucleotide Analogue with a Handle", Journal of Organic Chemistry, 1998, vol. 63, pp. 10035-10039.

Satoshi Obika et al., "Novel Bridged Nucleic Acids for Development of Nucleic Acid Medicine"; Abstract of the 29th Medicinal Chemistry Symposium, The Pharmaceutical Society of Japan, Division of Medicinal Chemistry, 2010, pp. 304-305, including English abstract.

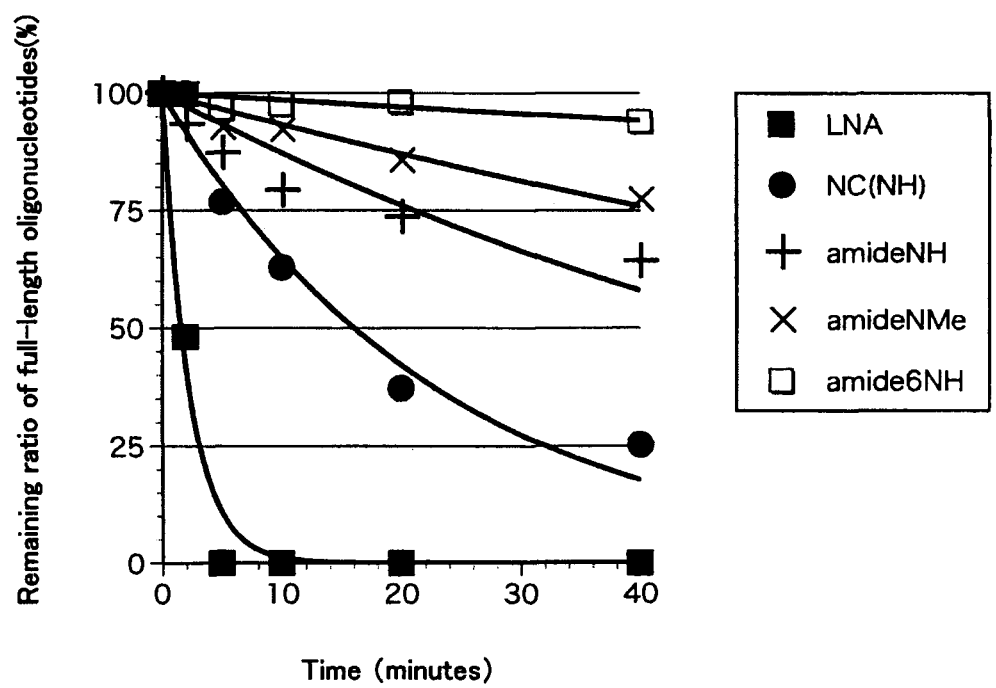

BRIDGED ARTIFICIAL NUCLEOSIDE AND NUCLEOTIDE

TECHNICAL FIELD

The present invention relates to novel bridged artificial nucleosides and nucleotides. More specifically, the invention relates to the bridged artificial nucleosides and nucleotides having high binding affinities to single-stranded RNAs and high nuclease resistance.

BACKGROUND ART

Treatments of disorders using nucleic acid drugs include antisense therapies, antigene therapies, aptamers, siRNAs and the like. An antisense therapy is the procedure for treatment or prevention of diseases involving inhibiting a translation process of pathogenic RNAs by externally introducing disease-associated mRNAs and their complementary oligonucleotides (antisense strands) to form the double strands. SiRNAs have the similar mechanism as the antisense therapies, involving inhibiting translation from mRNAs to proteins by administration of double-stranded RNAs to the body. Meanwhile, in the antigene therapies, transcription of DNA to RNA is inhibited by externally introducing triple-strand-forming oligonucleotides corresponding to the DNA sites transcribed into the pathogenic RNA. Aptamers, which are small nucleic acid molecules (oligonucleotides), exert their functions by binding to disease-related biological components, such as proteins.

Although various artificial nucleic acids has been developed as materials for such nucleic acid drugs, there has not been found ideal molecules yet. For example, the materials developed for nucleic acid drugs to date include S-oligo (phosphorothioate), 2',4'-BNA (bridged nucleic acid)/LNA (locked nucleic acid) (See Patent Documents 1 to 3 and Non-patent Documents 1 to 4). S-oligo is commercially available as an antisense drug for cytomegalovirus in United States. While this drug has a high nuclease resistance, it has a problem to be improved concerning about its low binding affinity to the target nucleic acid strands. Every 2',4'-BNA/LNAs which have ever been developed have high binding affinities to their target nucleic acid strands and they are the most promising molecules as the materials for the future nucleic acid drugs. However, they still remain to be improved with regard to their nuclease resistance which is not enough to be stable in vivo.

PRIOR ART DOCUMENTS

Patent Documents
  Patent Document 1: WO98/39352
  Patent Document 2: WO2005/021570
  Patent Document 3: WO2003/068795
Non-Patent Documents
  Non-Patent Document 1: C. Wahlestedt et al., Proc. Natl. Acad. Sci. USA, 2000, Vol. 97, No. 10, pp. 5633-5638.
  Non-Patent Document 2: Y. Hari et al., Bioorg. Med. Chem., 2006, Vol. 14, pp. 1029-1038.
  Non-Patent Document 3: K. Miyashita et al., Chem. Commun., 2007, pp. 3765-3767.
  Non-Patent Document 4: S. M. A. Rahman et al., J. Am. Chem. Soc., 2008, Vol. 130, No. 14, pp. 4886-4896.
  Non-Patent Document 5: M. Kuwahara et al., Nucleic Acids Res., 2008, Vol. 36, No. 13, pp. 4257-4265.
  Non-Patent Document 6: S. Obika et al., Bioorg. Med. Chem., 2001, Vol. 9, pp. 1001-1011.

SUMMARY OF INVENTION

Problems to be Solved by the Invention

It is desired to develop a novel molecule for antisense therapies which is not susceptible to nuclease degradation in vivo and has a high binding affinity and specificity for the target mRNAs and which can efficiently regulate expression of specific genes.

Means for Solving the Problems

The inventors have found that the novel bridged artificial nucleic acids having both of a good binding affinity for a single-stranded RNA and a nuclease resistance can be provided by introducing an amide bond into a bridge structure of 2',4'-BNA/LNA and have reached to the present invention.

The present invention provides compounds represented by the following formula I or formula II and salts thereof.

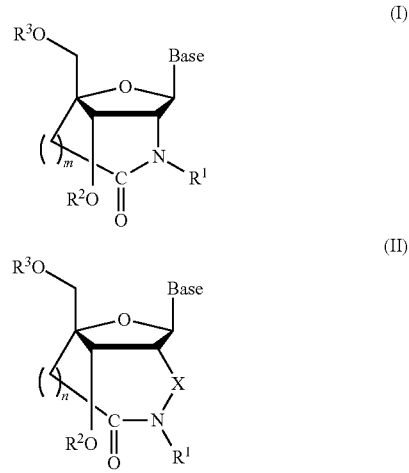

(wherein,

Base represents a purin-9-yl group or a 2-oxo-1,2-dihydropyrimidin-1-yl group that may have any one or more substituents selected from group α, wherein the group a consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, or a protecting group for an amino group on nucleic acid synthesis;

$R^2$ and $R^3$ represents, each independently, a hydrogen atom, a protecting group for a hydroxyl group on nucleic acid synthesis, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, an acyl group that may have any one or more substituents selected from the group α, a silyl group that may have any one or more substituents selected from the group α, a phosphate group that may have any one or more substituents selected from the group α, a phosphate group protected with a protecting group for nucleic acid synthesis, —P($R^4$)$R^5$ (wherein $R^4$ and $R^5$ represent, each independently, a hydroxyl group, a hydroxyl group protected with a protecting group for nucleic acid synthesis, a mercapto group, a mercapto group protected with a protecting group for nucleic acid synthesis, an amino group, an alkoxy group having 1 to 5 carbon atoms, an alkylthio group having 1 to 5 carbon atoms, an cyanoalkoxy group having 1 to 6 carbon atoms or an amino group substituted with an alkyl group having 1 to 6 carbon atoms.);

X represents an oxygen atom, a sulfur atom, an amino group or a methylene group;

m is an integer from 0 to 2; and n is an integer from 0 to 1).

In one embodiment, the Base in the formula I or formula II is a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group (uracilyl group), a 2-oxo-4-hydroxy-5-methyl-1,2-dihydropyrimidin-1-yl group (thyminyl group) or a 4-amino-5-methyl-2-oxo-1,2-dihydropyrimidin-1-yl group.

In one embodiment, the $R^1$ in the formula I or formula II is a hydrogen atom, a methyl group, an ethyl group, an n-propyl group, an isopropyl group, a phenyl group or a benzyl group.

In one embodiment, the m in the formula I is 0.

In one embodiment, the n in the formula II is 0.

In one embodiment, the Base in the formula I or formula II is a 2-oxo-4-hydroxy-5-methyl-1,2-dihydropyrimidin-1-yl group (thyminyl group).

The present invention also provides oligonucleotides containing at least one nucleoside structure represented by the following formula III or formula IV or pharmacologically acceptable salts thereof.

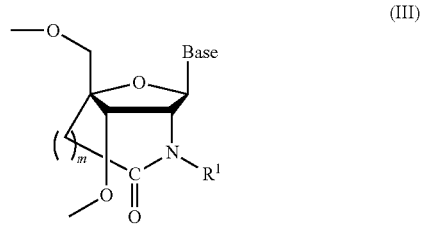

(III)

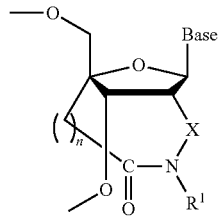

(IV)

(wherein

Base represents a purin-9-yl group or a 2-oxo-1,2-dihydropyrimidin-1-yl group that may have any one or more substituents selected from group α, wherein the group α consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, or a protecting group for an amino group on nucleic acid synthesis;

X represents an oxygen atom, a sulfur atom, an amino group or a methylene group;

m is an integer from 0 to 2; and n is an integer from 0 to 1.).

Effects of Invention

According to the present invention, novel 2',4'-bridged artificial nucleosides and nucleotides are provided. The oligonucleotide containing the 2',4'-bridged artificial nucleotide has a binding affinity for a single-stranded RNA comparable to known 2',4'-BNA/LNA and has an increased nuclease resistance over LNA. Particularly, it is expected to be applied to nucleic acid drugs because of its much stronger binding affinity for single-stranded RNAs than S-oligo's affinity.

BRIEF DESCRIPTION OF DRAWINGS

FIG. 1 is a graph illustrating a time course of remaining ratio of various oligonucleotides when digesting them with exonuclease.

MODE FOR CARRYING OUT THE INVENTION

The following definitions shall apply throughout the specification and the appended claims.

The term "linear alkyl group having 1 to 6 carbon atoms", as used herein, refers to any linear alkyl group having 1 to 6 carbons and specifically a methyl group, an ethyl group, an n-propyl group, an n-butyl group, an n-pentyl group or an n-hexyl group.

The term "linear alkoxy group having 1 to 6 carbon atoms", as used herein, encompasses alkoxy groups having any linear alkyl group having 1 to 6 carbon atoms. The linear alkoxy groups include a methyloxy group, an ethyloxy group, an n-propyloxy group and the like.

The term "linear alkylthio group having 1 to 6 carbon atoms", as used herein, encompasses alkylthio groups with any linear alkyl group having 1 to 6 carbon atoms. The linear alkylthio groups include a methylthio group, an ethylthio group, an n-propylthio group and the like.

The term "linear alkylamino group having 1 to 6 carbon atoms", as used herein, encompasses alkylamino groups containing one or two alkylamino groups with any linear alkyl group having 1 to 6 carbon atoms. The linear alkylamino groups include a methylamino group, a dimethylamino group, an ethylamino group, a methylethylamino group, a diethylamino group and the like.

The term "an alkyl group having 1 to 7 carbon atoms that may be branched or form a cyclic group", as used herein, encompasses any linear alkyl groups having 1 to 7 carbon atoms, any branched alkyl groups having 3 to 7 carbon atoms and any cyclic alkyl groups having 3 to 7 carbon atoms. It may be simply referred to as "lower alkyl group". For example, the linear alkyl groups having 1 to 7 carbon atoms include a methyl group, an ethyl group, an n-propyl group, an n-butyl group, an n-pentyl group, an n-hexyl group and an n-heptyl group; the branched alkyl groups having 3 to 7 carbon atoms include an isopropyl group, an isobutyl group, a tert-butyl group, an isopentyl group and the like; and the cyclic alkyl groups having 3 to 7 carbon atoms include a cyclobutyl group, a cyclopentyl group, a cyclohexyl group and the like.

The term "an alkenyl group having 2 to 7 carbon atoms that may be branched or form a cyclic group", as used herein, encompasses any linear alkenyl groups having 2 to 7 carbon atoms, any branched alkenyl groups having 3 to 7 carbon atoms and any cyclic alkenyl groups having 3 to 7 carbon atoms. It may be simply referred to as "lower alkenyl group". For example, the linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, a 1-hexenyl group and the like; the branched alkenyl groups having 3 to 7 carbon atoms include an isopropenyl group, a 1-methyl-1-propenyl group, a 1-methyl-2-propenyl group, a 2-methyl-1-propenyl group, a 2-methyl-2-propenyl group, a 1-methyl-2-butenyl group and the like; and the cyclic alkenyl groups having 3 to 7 carbon atoms include a cyclobutenyl group, a cyclopentenyl group, a cyclohexenyl group and the like.

The term "aryl group having 3 to 12 carbon atoms that may contain heteroatoms", as used herein, encompasses any aromatic hydrocarbons having 6 to 12 carbon atoms and consisting of only hydrocarbons and any heteroaromatic compounds having 3 to 12 carbon atoms and ring structures containing heteroatoms (a nitrogen atom, an oxygen atom or a sulfur atom). The aromatic hydrocarbons having 6 to 12 carbon atoms and consisting of only hydrocarbons include a phenyl group, a naphthyl group, an indenyl group, an azulenyl group and the like; and the heteroaromatic compounds having 3 to 12 carbon atoms and a ring structure containing heteroatoms include a pyridyl group, a pyrrolyl group, a quinolyl group, an indolyl group, an imidazolyl group, a furyl group, a thienyl group and the like.

The examples of the term "aralkyl group with an aryl moiety having 3 to 12 carbon atoms that may contain heteroatoms", as used herein, include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, a 3-thienylpropyl group and the like.

The examples of the term "acyl group", as used herein, include aliphatic acyl groups and aromatic acyl groups. Specifically, the examples of aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, a 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1-methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group and a heneicosanoyl group; carboxylated alkylcarbonyl groups such as a succinoyl group, a glutaroyl group and an adipoyl group; lower halogeno alkylcarbonyl groups such as a chloroacetyl group, a dichloroacetyl group, a trichloroacetyl group and a trifluoroacetyl group; lower alkoxy lower alkylcarbonyl groups such as a methoxyacetyl group; unsaturated alkylcarbonyl groups such as a (E)-2-methyl-2-butenoyl group. The examples of aromatic acyl groups include arylcarbonyl groups such as a benzoyl group, an α-naphthoyl group and a β-naphthoyl group; halogenoarylcarbonyl groups such as a 2-bromobenzoyl group and a 4-chlorobenzoyl group; lower alkoxylated arylcarbonyl groups such as a 2,4,6-trimethylbenzoyl group and a 4-toluoyl group; lower alkoxylated arylcarbonyl groups such as a 4-anisoyl group; carboxylated arylcarbonyl groups such as a 2-carboxybenzoyl group, 3-carboxybenzoyl group and a 4-carboxybenzoyl group; nitrated arylcarbonyl groups such as a 4-nitrobenzoyl group and a 2-nitrobenzoyl group; lower alkoxycarbonylated arylcarbonyl groups such as a 2-(methoxycarbonyl)benzoyl group; arylated arylcarbonyl groups such as a 4-phenylbenzoyl group. Preferably the acyl group is a formyl group, an acetyl group, a propionyl group, a butyryl group, an isobutyryl group, a pentanoyl group, a pivaloyl group or a benzoyl group.

The examples of the term "silyl group", as used herein, include tri-lower alkylsilyl groups such as a trimethylsilyl group, a triethylsilyl group, an isopropyldimethylsilyl group, a t-butyldimethylsilyl group, a methyldiisopropylsilyl group, a methyl di-t-butylsilyl group and a triisopropylsilyl group; tri-lower alkylsilyl groups substituted with one or two aryl groups such as a diphenylmethylsilyl group, a butyldiphenylbutylsilyl group, a diphenylisopropylsilyl group and a phenyldiisopropylsilyl group. Preferably the silyl group is a trimethylsilyl group, a triethylsilyl group, a triisopropylsilyl group, a t-butyldimethylsilyl group or a t-butyldiphenylsilyl group, more preferably a trimethylsilyl group.

The term "halogen atom", as used herein, includes, for example, a fluorine atom, a chlorine atom, a bromine atom or an iodine atom. Preferably, the halogen atom is a fluorine atom or a chlorine atom.

The term "protecting group" in phrases "a protecting group for an amino group on nucleic acid synthesis", "protecting group for a hydroxyl group on nucleic acid synthesis", "a hydroxyl group protected with a protecting group for nucleic acid synthesis", "a phosphate group protected with a protecting group for nucleic acid synthesis" and "a mercapto group protected with a protecting group for nucleic acid synthesis", as used herein, is not limited to specific groups as far as the groups may stably protect an amino group, a hydroxyl group, a phosphate group or a mercapto group during nucleic acid synthesis. Specifically, the protecting groups refer to those which are stable in acid or neutral condition and may be cleaved by chemical methods such as hydrogenolysis, hydrolysis, electrolysis and photodissociation. Such protecting groups include, for example, lower alkyl groups, lower alkenyl groups, acyl groups, a tetrahydropyranyl or a tetrahydrothiopyranyl group, a tetrahydrofuranyl or a tetrahydrothiofuranyl group, a silyl group, lower alkoxymethyl groups, lower alkoxylated lower alkoxymethyl groups, lower halogenoalkoxymethyl groups, lower alkoxylated ethyl groups, halogenated ethyl groups, methyl groups substituted with one to three aryl groups, "methyl groups substituted with one to three aryl groups with the aryl ring substituted with a lower alkyl group, a lower alkoxy group, a halogen atom or a cyano group", lower alkoxycarbonyl groups, "aryl groups substituted with a halogen atom, a lower alkoxy group or a nitro group", "lower alkoxycarbonyl groups substituted with a halogen atom or a tri-lower alkylsilyl group", alkenyloxycarbonyl groups, "aralkyloxycarbonyl groups with aryl rings that may be substituted with a lower alkoxy or a nitro group" and the like.

More specifically, the tetrahydropyranyl groups or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, a 4-methoxytetrahydrothiopyran-4-yl group and the like. The tetrahydrofuranyl groups or tetrahydrothiofuranyl groups include a tetrahydrofuran-2-yl group and a tetrahydrothiofuran-2-yl group. The lower alkoxymethyl groups include a methoxymethyl group, a 1,1-dimethyl-1-methoxymethyl group, an ethoxymethyl group, a propoxymethyl group, an isopropoxymethyl group, a butoxymethyl group, a t-butoxymethyl group and the like. The lower alkoxylated lower alkoxymethyl groups include a 2-methoxyethoxymethyl group and the like. The lower halogeno alkoxymethyl groups include a 2,2,2-trichloroethoxymethyl group, a bis (2-chloroethoxy)methyl group and the like. The lower alkoxylated ethyl groups include a 1-ethoxyethyl group, a 1-(isopropoxy) ethyl group and the like. The halogenated ethyl groups include a 2,2,2-trichloroethyl group and the like. The methyl groups substituted with one to three aryl groups include a benzyl group, an α-naphthylmethyl group, a β-naphthylmethyl group, a diphenylmethyl group, a triphenylmethyl group, an α-naphthyldiphenylmethyl group, a 9-anthrylmethyl group and the like. The "methyl groups substituted with one to three aryl groups with aryl rings substituted with a lower alkyl group, a lower alkoxy group, a halogen atom or a cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, a 4-cyanobenzyl group and the like. The lower alkoxycarbonyl groups include a methoxycarbonyl group, an ethoxycarbonyl group, a t-butoxycarbonyl group, an isobutoxycarbonyl group and the like. The "aryl groups substituted with a halogen atom, a lower alkoxy group or a nitro group" include a 4-chlorophenyl group, a 2-fluorophenyl group, a 4-methoxyphenyl group, a 4-nitrophenyl group, a 2,4-dinitrophenyl group and the like. The "lower alkoxycarbonyl groups substituted with a halogen atom or a tri-lower alkylsilyl group" include a 2,2,2-trichloroethoxycarbonyl group, a 2-trimethylsilyl ethoxycarbonyl group and the like. The alkenyloxycarbonyl groups include a vinyloxycarbonyl group, an aryloxycarbonyl group and the like. The "aralkyloxycarbonyl groups with an aryl ring that may be substituted with a lower alkoxy or a nitro group" include a benzyloxycarbonyl group, a 4-methoxybenzyloxycarbonyl group, a 3,4-dimethoxybenzyloxycarbonyl group, a 2-nitrobenzyloxycarbonyl group, a 4-nitrobenzyloxycarbonyl group and the like.

The "protecting groups for an hydroxyl group on nucleic acid synthesis" include preferably aliphatic acyl groups, aromatic acyl groups, methyl groups substituted with one to three aryl groups, "methyl groups substituted with one to three aryl groups with aryl rings substituted with a lower alkyl group, a lower alkoxy group, a halogen atom or a cyano group" or a silyl group, and more preferably an acetyl group, a benzoyl group, a benzyl group, a p-methoxybenzoyl group, a dimethoxytrityl group, a monomethoxytrityl group or a tert-butyldiphenylsilyl group. The protecting group in the phrase "a hydroxyl group protected with a protecting group for nucleic acid synthesis" is preferably an aliphatic acyl group, an aromatic acyl group, "a methyl group substituted with one to three aryl groups", "an aryl group substituted with a halogen atom, a lower alkoxy group or a nitro group", a lower alkyl group or a lower alkenyl group, and more preferably a benzoyl group, a benzyl group, a 2-chlorophenyl group, a 4-chlorophenyl group or a 2-propenyl group. The "protecting group for an amino group on nucleic acid synthesis" is preferably an acyl group, and more preferably a benzoyl group. The "protecting group" in the phrase "a phosphate group protected with a protecting group for nucleic acid synthesis" is preferably a lower alkyl group, a lower alkyl group substituted with a cyano group, an aralkyl group, "an aralkyl group with an aryl ring substituted with a nitro group or a halogen atom" or "an aryl group substituted with a lower alkyl group, a halogen atom or a nitro group", and more preferably a 2-cyanoethyl group, a 2,2,2-trichloroethyl group, a benzyl group, a 2-chlorophenyl group or a 4-chlorophenyl group. The "protecting group" in the phrase "a mercapto group protected with a protecting group for nucleic acid synthesis" is preferably an aliphatic acyl group or an aromatic acyl group, and more preferably a benzoyl group.

Herein, among the groups represented with —P(R$^4$)R$^5$ (wherein R$^4$ and R$^5$ each independently represent a hydroxyl group, a hydroxyl group protected with a protecting group for nucleic acid synthesis, a mercapto group, a mercapto group protected with a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms or an amino group substituted with an alkyl group having 1 to 6 carbon atoms), the ones wherein R$^4$ can be represented with OR$^{4a}$ and R$^5$ can be represented with NR$^{5a}$ are referred to as a "phosphoramidite group". The phosphoramidite groups include, preferably, groups represented by the formula —P(OC$_2$H$_4$CN)(N(iPr)$_2$) or the formula —P(OCH$_3$)(N(iPr)$_2$). In these formulas, iPr represents an isopropyl group.

The terms "artificial nucleoside" and "nucleoside analogue", as used herein, refer to an unnatural "nucleoside" in which a purine or a pyrimidine base is bonded to sugar, as well as those in which a heteroaromatic ring and an aromatic hydrocarbon ring other than purine and pyrimidine, serving to substitute for a purine or a pyrimidine base, are bonded with sugars.

The terms "artificial oligonucleotide" and "oligonucleotide analogue", as used herein, refer to unnatural derivatives of "oligonucleotides" in which 2 to 50 of same or different "nucleosides" or "nucleoside analogues" are bonded via phosphodiester bonds. Such analogues include preferably sugar derivatives with sugar moieties modified; thioated derivatives with phosphate diester moiety thioated; esters with terminal phosphate moiety esterificated; amides in which amino groups on a purine base is amidated and preferably sugar derivatives with sugar moiety modified.

The term "salts thereof", as used herein, refers to salts of compounds represented by the formula I or II according to the invention. These salts may include preferably alkaline metal salts such as sodium salts, potassium salts and lithium salts; alkaline earth metal salts such as calcium salts and magnesium salts; metal salts such as aluminum salts, iron salts, zinc salts, cuprous salts, nickel salts and cobalt salts; mineral salts such as ammonium salts; amine salts, for example organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, Tris (hydroxymethyl)aminomethane salts; inorganic acid salts such as halide acid salts (for example hydrofluoride, hydrochloride, hydrobromide and hydriodide), nitrate, perchlorate, sulfate and phosphate; organic acid salts including lower alkanesulfonates such as methanesulfonates, trifluoromethanesulfonates and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates and aspartates.

The term "pharmacologically acceptable salts thereof", as used herein, refers to salts of oligonucleotide analogues containing at least one of nucleoside structures represented by the formula III or the formula IV of the invention. These salts may include preferably alkaline metal salts such as sodium salts, potassium salts and lithium salts; alkaline earth metal salts such as calcium salts and magnesium salts; metal salts such as aluminum salts, iron salts, zinc salts, cuprous salts, nickel salts and cobalt salts; mineral salts such as ammonium salts; amine salts, for example organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, Tris (hydroxymethyl)aminomethane salts; inorganic acid salts such as halide acid salts (for example hydrofluoride, hydrochloride, hydrobromide, hydriodide), nitrates, perchlorates, sulfates, phosphates; organic acid salts including lower alkanesulfonates such as methanesulfonates, trifluoromethanesulfonates and ethanesulfonates, arylsulfonates such as benzenesulfonates and p-toluenesulfonates, acetate, malates, fumarates, succinates, citrates, tartrates, oxalates and maleates; and amino acid salts such as glycine salts, lysine salts, arginine salts, ornithine salts, glutamates and aspartates.

The invention is described in more detail below.

2',4'-bridged artificial nucleoside and nucleotide of the invention or salts thereof have the structures represented by the formula I or formula II as follows:

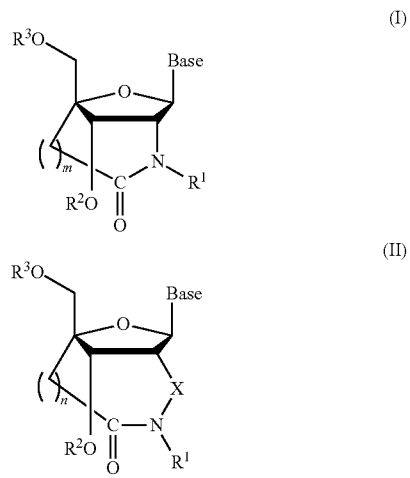

(wherein,

Base represents a purin-9-yl group or a 2-oxo-1,2-dihydropyrimidin-1-yl group that may have any one or more substituents selected from group α, wherein the group a consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, or a protecting group for an amino group on nucleic acid synthesis;

$R^2$ and $R^3$ represents, each independently, a hydrogen atom, a protecting group for a hydroxyl group on nucleic acid synthesis, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, an acyl group that may have any one or more substituents selected from the group α, a silyl group that may have any one or more substituents selected from the group α, a phosphate group that may have any one or more substituents selected from the group α, a phosphate group protected with a protecting group for nucleic acid synthesis, —P($R^4$)$R^5$ (wherein $R^4$ and $R^5$ represent, each independently, a hydroxyl group, a hydroxyl group protected with a protecting group for nucleic acid synthesis, a mercapto group, a mercapto group protected with a protecting group for nucleic acid synthesis, an amino group, an alkoxy group having 1 to 5 carbon atoms, an alkylthio group having 1 to 5 carbon atoms, an cyanoalkoxy group having 1 to 6 carbon atoms or an amino group substituted with an alkyl group having 1 to 6 carbon atoms.);

X represents an oxygen atom, a sulfur atom, an amino group or a methylene group;

m is an integer from 0 to 2; and n is an integer from 0 to 1.).

In formula I or formula II described above, Base is a purine base (i.e., purin-9-yl group) or a pyrimidine base (i.e., 2-oxo-1,2-dihydropyrimidin-1-yl group). These bases may have any one or more substituents selected from group α consisting of a hydroxyl group, linear alkyl groups having 1 to 6 carbon atoms, linear alkoxy groups having 1 to 6 carbon atoms, a mercapto group, linear alkylthio groups having 1 to 6 carbon atoms, an amino group, linear alkylamino groups having 1 to 6 carbon atoms and halogen atoms.

The specific examples of base (Base) described above include a 6-aminopurin-9-yl group (adeninyl group), a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group (guaninyl group), a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group (cytosinyl group), a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group (uracilyl group), a 2-oxo-4-hydroxy-5-methyl-1,2-dihydropyrimidin-1-yl group (thyminyl group) and a 4-amino-5-methyl-2-oxo-1,2-dihydropyrimidin-1-yl group.

Among them, considering the introduction into nucleic acid drugs, Base is preferably one of compounds which have the structural formulas represented as follows:

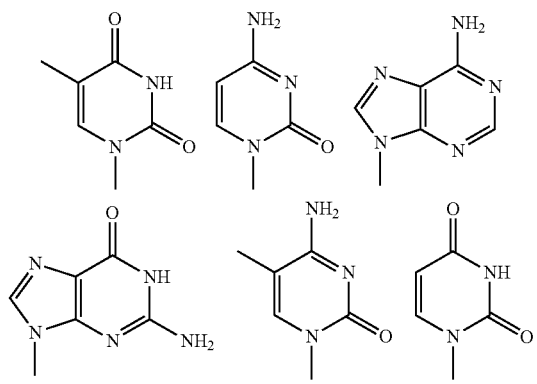

such as a 2-oxo-4-hydroxy-5-methyl-1,2-dihydropyrimidin-1-yl group (thyminyl group), a 2-oxo-4-amino-1,2-dihydropyrimidin-1-yl group (cytosinyl group), a 6-aminopurin-9-yl group (adeninyl group), a 2-amino-6-hydroxypurin-9-yl group (guaninyl group), a 4-amino-5-methyl-2-oxo-1,2-dihydropyrimidin-1-yl group and a 2-oxo-4-hydroxy-1,2-dihydropyrimidin-1-yl group (uracilyl group), and more particularly a 2-oxo-4-hydroxy-5-methyl-1,2-dihydropyrimidin-1-yl group (thyminyl group). During the synthesis of the oligonucleotides, a hydroxyl group is preferably protected by a protecting group.

In formula I or formula II above, $R^1$ is a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms or an aralkyl group with an aryl moiety having 3 to 12 carbon atoms that may have any one or more substituents selected from the group α and may contain heteroatoms. More preferably, $R^1$ is a hydrogen atom, a methyl group, an ethyl group, an n-propyl group, an isopropyl group, a phenyl group or a benzyl group, even more preferably $R^1$ is a hydrogen atom or a methyl group.

In formula I or formula II above, m is an integer from 0 to 2; and n is an integer from 0 to 1. Therefore, the ring containing position 2', position 3', position 4' and a bridge region is a 5 to 7-membered ring.

In formula II described above, X is an oxygen atom, a sulfur atom, an amino group or a methylene group. Preferably, X is an oxygen atom or an amino group. When X is an amino group or a methylene group, it may be substituted with a lower alkyl group.

The novel 2',4'-bridged artificial nucleoside of the invention has an amide bond introduced into a bridge structure of a conventional 2',4'-BNA/LNA. Specifically, an amide bond is formed between an amino group at the position 2' and a carbonyl group stretching from position 4' on the sugar moiety. Thus, the nucleoside has an amide bond which has less structural fluctuation and has a good hydrophilicity, resulting in the structure of the sugar moiety fixed by the bridging.

2',4'-bridged artificial nucleotides may be easily prepared from the 2',4'-bridged artificial nucleosides of the invention. For example, triphosphorylation may be easily carried out according to the method described in Non-patent Document 5.

The oligonucleotides of the invention or pharmacologically acceptable salts thereof contain at least one nucleoside structure represented by formula III or formula IV below:

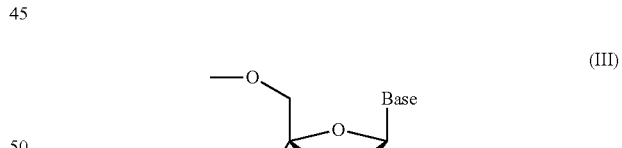

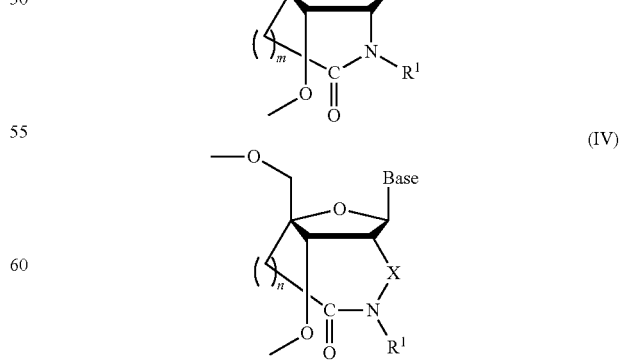

(wherein Base, $R^1$, X, m and n are as defined for formulas I and II above.).

The oligonucleotides of the invention have at least one of nucleoside structures above at any positions in the structures. The position and number of the nucleoside structures, which are not limited to the specific position and number, may be conveniently selected depending on the purposes.

An oligonucleotide analogue (antisense molecule) containing such a nucleoside structure, due to having a structure fixed by an amide bond as described above, is resistant to degradation by various nucleases and thus may remain in vivo for a prolonged time after the administration. For example, the oligonucleotide analogue forms a stable double strand with mRNA to inhibit biosynthesis of a protein contributing to pathogenesis, or alternatively forms a triple strand with a double-stranded DNA in a genome to inhibit its transcription into mRNA. Also the oligonucleotide analogues may be used to inhibit multiplication of infecting virus. Furthermore the oligonucleotide analogues are expected to have a high biocompatibility because they have amide bonds and also to serve as aptamers to recognize biological substances such as proteins.

With all these facts, the oligonucleotide analogues synthesized using the 2',4'-bridged artificial nucleosides of the invention are expected their usefulness as pharmaceutical agents (antisense molecules) inhibiting a function of a specific gene to treat a disease, such as antitumor agents and antiviral drugs.

Particularly, for antisense therapies, both of a binding affinity for complementary sense strand RNAs and a resistance to in vivo DNA are required. Generally, a nucleic acid in the form of a single strand is known to constantly have a structural fluctuation of a sugar moiety between the form close to a sugar moiety in a double-stranded DNA and the form close to a sugar moiety in a double-stranded DNA-RNA or a double-stranded RNA. When a single-stranded nucleic acid forms a double strand with the complementary RNA strand, its structure of the sugar moiety is fixed. Therefore, the 2',4'-bridged artificial nucleosides of the invention form readily double strands with the intended RNA strands, which may be then maintained stably, because the sugar moiety has been already kept to the structure capable of forming double strands. Furthermore, a double-stranded nucleic acid is known to be stabilized with hydrated water with a chain like structure referred to as "network of water molecules". The 2',4'-bridged artificial nucleosides of the invention have amide bonds which provide hydrophilicity to the bridges on their sugar moieties, as a result of which the nucleosides may be more stabilized. Moreover, an amide bond in the bridge of the sugar moiety in the nucleoside is thought to makes the nucleoside less recognizable to in-vivo enzymes, which contributes to its nuclease resistance.

Additives typically used in the art of pharmaceuticals such as excipients, binders, preservatives, oxidation stabilizers, disintegrants, lubricants and flavoring substances can be added to the oligonucleotide analogues of the invention to prepare parental formulations or liposomal formulations. Also, for example, topical formulations such as liquids, creams and ointments may be prepared by adding pharmaceutical carriers typically used in the art.

EXAMPLES

Synthesis of the 2',4'-bridged artificial nucleosides of the invention and analogues thereof is described in detail in reference to the following examples.

Example 1

Synthesis of the Nucleoside Analogue: 2'-amino-3'-O-[2-cyanoethoxy(diisopropylamino) phosphino]-5'O-dimethoxytrityl-2'-N,4'-C-oxomethylene thymidine (Compound 16: Amide NH)

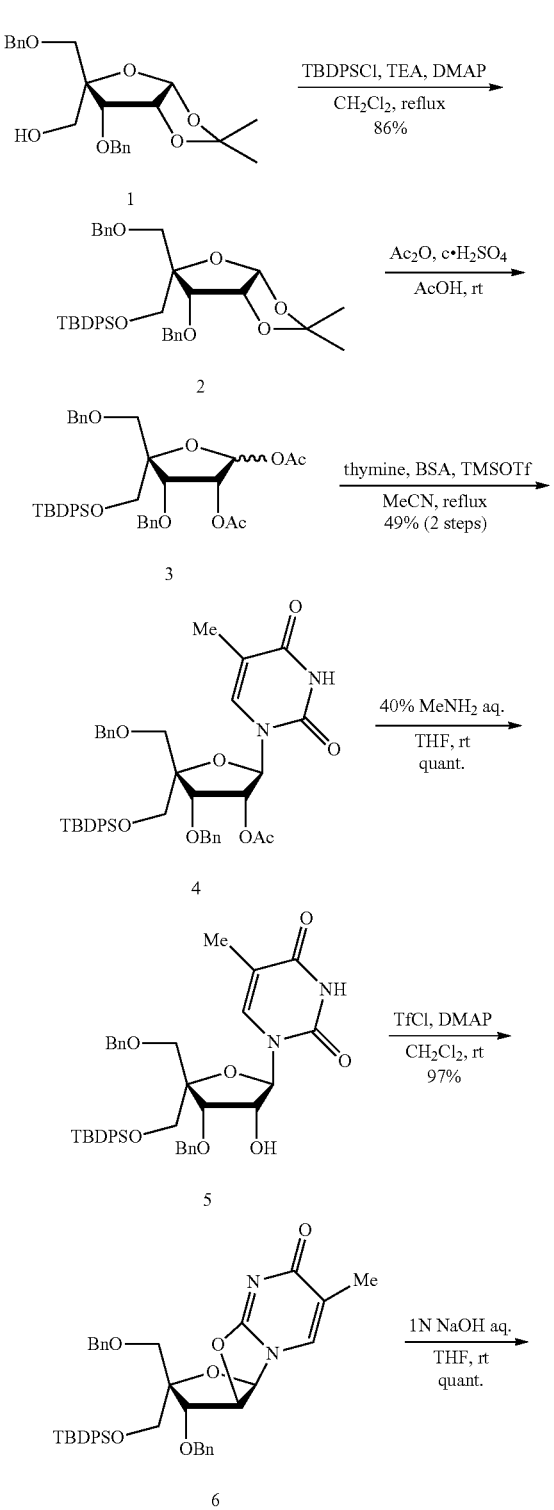

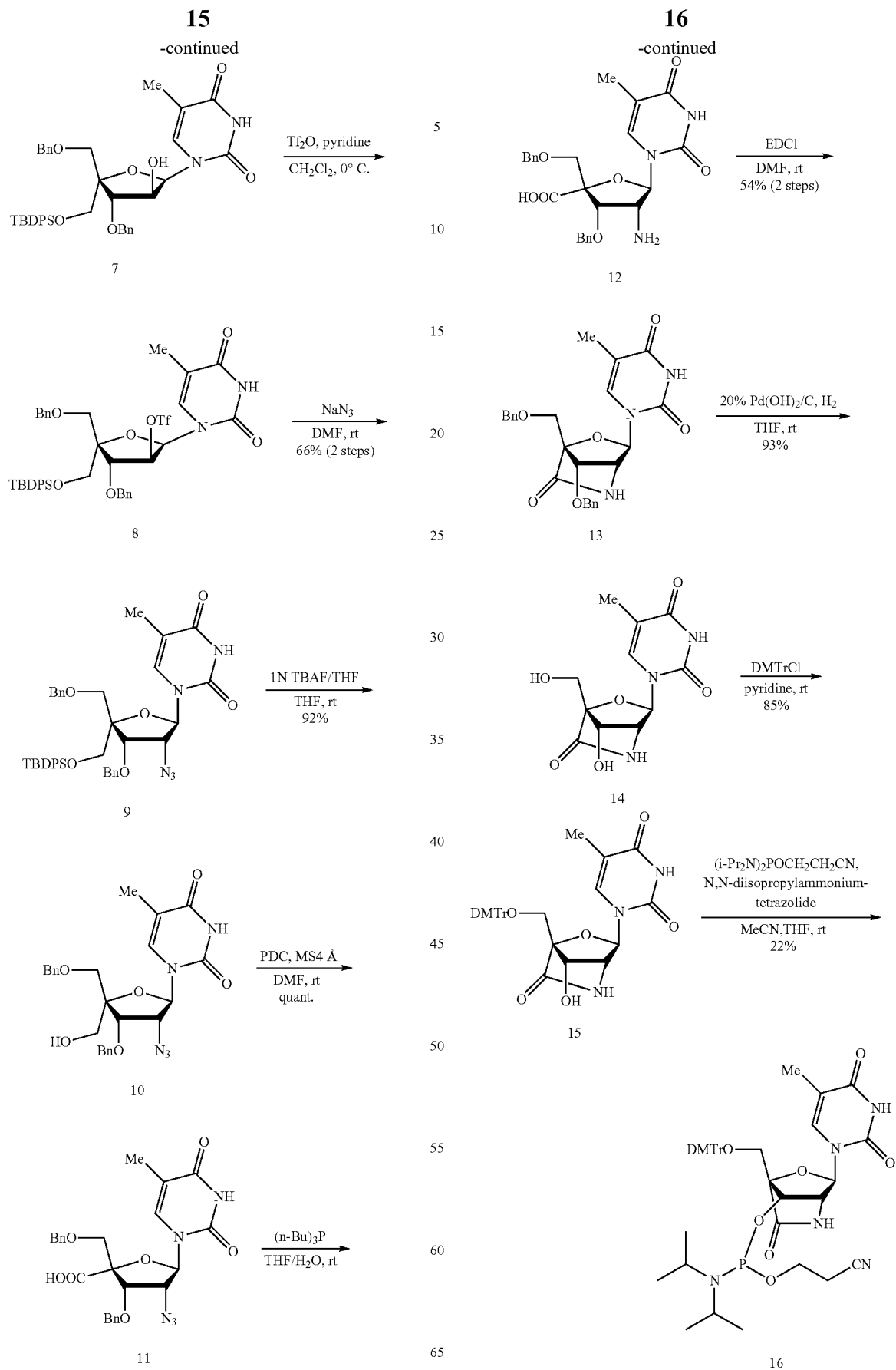

(1) Synthesis of Compound 2

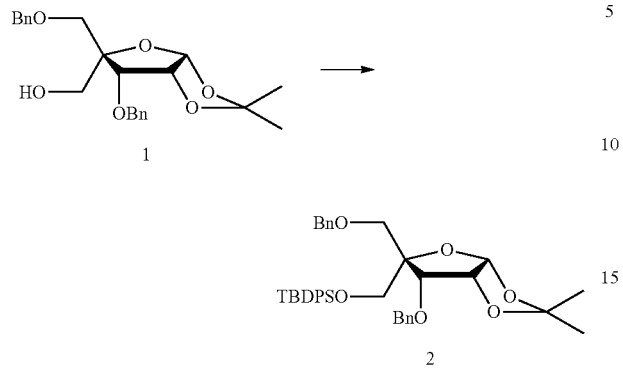

Under nitrogen stream, to a solution of compound 1 (14.7 g, 36.8 mmol) in dichloromethane (80 mL) was added triethylamine (15.1 mL, 110 mmol) followed by, under ice-cooling, dimethylaminopyridine (0.90 g, 7.36 mmol), tert-butyldiphenylsilyl chloride (15.1 mL, 58.9 mmol) and the mixture was then refluxed. Compound 1 may be prepared according to Koshkin, A. A. et al., Tetrahedron, 1998, vol. 54, pp. 3607-3630 and Singh, S. K. et al., Chem. Commun., 1998, pp. 455-456. After 20 hours, water was added to the mixture which was then extracted with methylene chloride, and the organic layer was washed with water and saturated saline and dried over anhydrous sodium sulphate. The resultant crude product was purified by silica-gel chromatography (n-hexane:ethyl acetate=9:1(v/v)) to give compound 2 (20.4 g:yield 85.9%) as an oil.

The physical property data of the resultant compound 2 was as follows: $[\alpha]_D^{25}$ +84.8 (c 1.00, CHCl$_3$); IR (KBr): 1457, 1372, 1105, 1025 cm$^{-1}$; $^1$H-NMR (270 MHz, CDCl$_3$): δ1.03 (9H, s), 1.29 (6H, s), 3.62, 3.73 (2H, AB, J=10.5 Hz), 4.03, 4.08 (2H, AB, J=11.3 Hz), 4.20 (1H, d, J=5.1 Hz), 4.45, 4.55 (2H, AB, J=11.9 Hz), 4.49, 4.66 (2H, AB, J=12.2 Hz), 4.58 (1H, dd, J=5.1 Hz, 4.1 Hz), 5.76 (1H, d, J=4.1 Hz), 7.21-7.70 (20H, m); $^{13}$C-NMR (75.45 MHz, CDCl$_3$): δ19.9, 26.9, 27.2, 27.5, 65.3, 72.6, 73.0, 74.2, 78.8, 80.2, 88.2, 104.8, 113.8, 128.2, 128.2, 128.3, 128.3, 128.8, 128.9, 130.1, 133.9, 134.1, 135.4, 136.3, 136.4, 138.5, 138.7; MS (FAB): m/z 661 (MNa$^+$): Calculated C$_{39}$H$_{46}$O$_6$Si: C, 73.32; H, 7.26, Found C, 73.44; H, 7.32.

(2) Synthesis of Compound 4

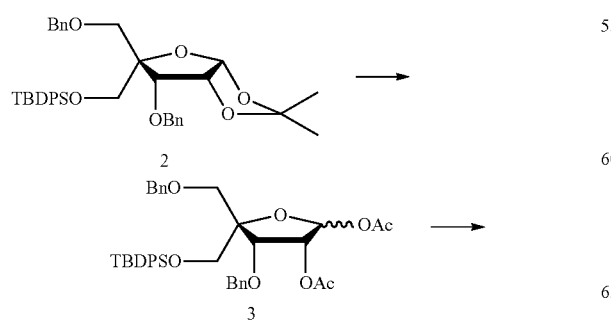

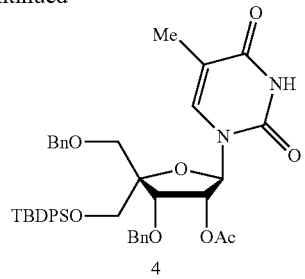

To 0.1% (v/v) solution of compound 2 from (1) above (1.00 g, 1.57 mmol) in concentrated sulfuric acid and acetic acid (1.11 mL) was added sulfuric anhydride (1.78 mL, 18.8 mmol) and the mixture was stirred. After 3.5 hours, the reactant was added to saturated sodium bicarbonate solution, which was then extracted with ethyl acetate, and next the organic layer was washed with water and saturated saline and dried over anhydrous sodium sulphate. After the solvent was distilled away, the crude product of compound 3 (1.07 g) was given as an oil, which was used for the following introduction of thymine.

Under nitrogen stream, to a solution of crude product of compound 3 in acetonitrile (5 mL) was added thymine (297 mg, 2.36 mmol), which was then dissolved using an oil bath at 40° C., followed by addition of N,O-bis trimethylsilyl acetamide (1.34 mL, 5.50 mmol), trimethylsilyl trifluoromethanesulfonate (0.28 mL, 1.57 mmol) at room temperature, and stirring at reflux for 1 hour. After saturated sodium bicarbonate solution was added to the mixture which was then extracted with ethyl acetate, and the organic layer was washed with water and saturated saline and then dried over anhydrous sodium sulphate. After the solvent was distilled away, the resultant crude product was purified by silica-gel chromatography (n-hexane:ethyl acetate=10:1→1:1 (v/v)) to give compound 4 (367 mg:yield 49% (2 steps)) as a white amorphous.

The physical property data of the resultant compound 4 was as follows: melting point: 55-59° C.; $[\alpha]_D^{24}$ -11.7 (c 0.800, CHCl$_3$); IR (KBr):1747, 1693, 1232, 1113 cm$^{-1}$; $^1$H-NMR (300 MHz, CDCl$_3$): δ1.04 (9H, s), 1.52 (3H, s), 1.96 (3H, s), 3.71, 3.76 (2H, AB, J=10.5 Hz), 3.69, 3.94, (2H, AB, J=10.8 Hz), 4.41 (1H, d, J=6.0 Hz), 4.54, 4.58 (2H, AB, J=12.6 Hz), 4.54, 4.58 (2H, AB, J=12.6 Hz), 5.38 (1H, t, J=6.0 Hz), 6.16 (1H, d, J=6.0 Hz), 7.18-7.63 (20H, m), 7.87 (1H, s); $^{13}$C-NMR (75.45 MHz, CDCl$_3$): δ12.0, 19.2, 20.6, 26.9, 63.8, 72.2, 73.7, 74.6, 74.9, 77.7, 85.5, 87.9, 111.3, 127.6, 127.7, 127.7, 127.8, 128.1, 128.3, 128.6, 129.7, 129.9, 132.6, 132.9, 135.5, 135.7, 135.7, 137.2, 137.5, 150.4, 163.6, 170.2; MS (FAB): m/z 749 (MH$^+$), Calculated C$_{43}$H$_{48}$N$_2$O$_8$Si: C, 68.96; H, 6.46; N, 3.74. Found C, 68.92; H, 6.45; N, 3.74.

(3) Synthesis of Compound 5

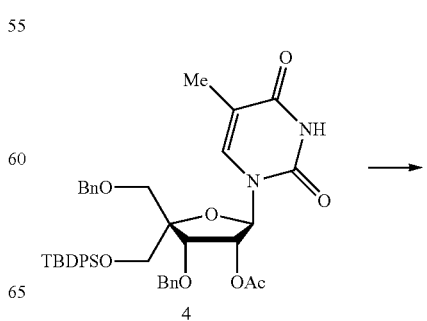

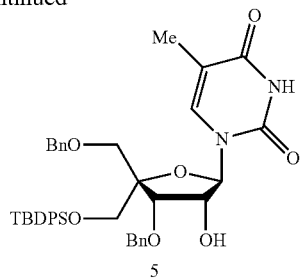

5

To a solution of compound 4 from (2) above (326 mg, 0.435 mmol) in tetrahydrofuran (2.4 mL) was added 40% (v/v) methylamine solution (1.1 mL, 13 mmol) and the mixture was stirred for 30 minutes at room temperature. After the solvent was distilled away, the mixture was extracted with ethyl acetate and dried over anhydrous sodium sulphate. After the solvent was distilled away, the resultant crude product was purified by flash column chromatography (n-hexane:ethyl acetate=1:1 (v/v)) to give compound 5 (312 mg:yield 100%) as a white amorphous.

The physical property data of the resultant compound 5 was as follows: melting point: 61-63° C.; $[\alpha]_D^{25}$ −12.2 (c 0.750, CHCl$_3$); IR (KBr): 3403, 3175, 1688, 1468, 1272, 1113 cm$^{-1}$; $^1$H-NMR (270 MHz, CDCl$_3$): δ1.06 (9H, s), 1.60 (3H, s), 3.54, 3.63 (2H, AB, J=10.5 Hz), 3.64 (1H, d, J=10.8 Hz), 3.73, 3.83 (2H, AB, J=10.5 Hz), 4.31 (1H, d, J=4.9 Hz,) 4.41 (1H, ddd, J=4.9 Hz, 4.9 Hz, 10.8 Hz), 4.50 (2H, s), 4.67, 4.73 (2H, AB, J=11.1 Hz), 5.95 (1H, d, J=4.9 Hz), 7.21-7.66 (20H, m), 8.12 (1H, s); $^{13}$C-NMR (67.80 MHz, CDCl$_3$): δ12.1, 19.1, 26.8, 64.2, 72.2, 73.8, 74.2, 74.5, 77.2, 78.5, 88.1, 90.9, 110.9, 127.7, 127.8, 127.9, 128.0, 128.1, 128.2, 128.6, 130.0, 132.2, 132.2, 135.6, 135.7, 136.5, 137.2, 150.3, 163.4; MS (FAB): m/z 707 (MH$^+$). Calculated C$_{41}$H$_{46}$N$_2$O$_7$Si: C, 69.66; H, 6.56; N, 3.96. Found C, 69.59; H, 6.59; N, 3.93.

(4) Synthesis of Compound 6

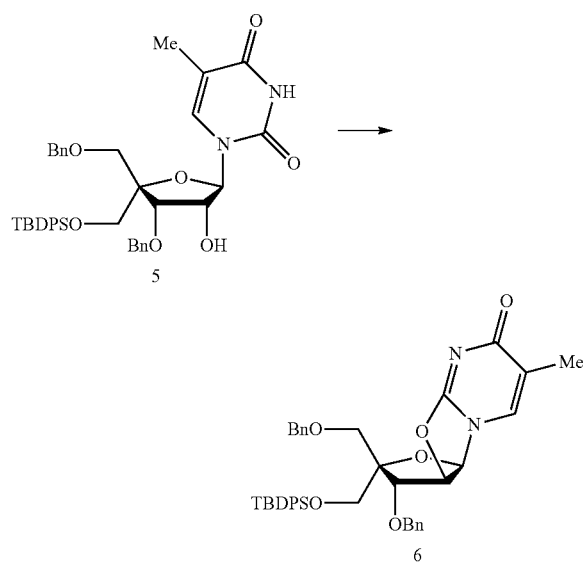

Under nitrogen stream, to a solution of compound 5 from (3) above (262 mg, 0.37 mmol) in dichloromethane (7 mL) was added dimethylaminopyridine (181 mg, 1.48 mmol). Trifluoromethanesulfonyl chloride (0.12 mL, 1.11 mmol) was then added to the mixture on ice cooling, which was then warmed gently to room temperature and stirred for 1 hour. Saturated sodium bicarbonate solution was added to the mixture which was then extracted with dichloromethane, and the organic layer was then washed with saturated saline and dried over anhydrous sodium sulphate. After the solvent was distilled away, compound 6 (248 mg:yield 97%) was give as a white amorphous.

The physical property data of the resultant compound 6 was as follows: melting point: 51-54° C.; $[\alpha]_D^{26}$ −33.5 (c 1.000, CHCl$_3$); IR (KBr): 1667, 1650, 1563, 1482, 1112 cm$^{-1}$; $^1$H-NMR (300 MHz, CDCl$_3$): δ1.03 (9H, s), 1.99 (3H, s), 3.29, 3.34 (2H, AB, J=10.8 Hz), 3.68, 3.82 (2H, AB, J=10.5 Hz), 4.31 (1H, d, J=3.9 Hz), 4.32, 4.38 (2H, AB, J=12 Hz), 4.60, 4.81 (2H, AB, J=11.4 Hz), 5.50 (1H, dd, J=6.3, 3.9 Hz), 6.23 (1H, d, J=6.3 Hz), 7.08-7.66 (21H, m); $^{13}$C-NMR (75.45 MHz, CDCl$_3$): δ14.0, 18.9, 26.7, 64.0, 69.4, 73.4, 84.0, 87.1, 88.7, 89.9, 119.0, 127.4, 127.6, 127.7, 127.8, 128.1, 128.3, 128.4, 128.5, 129.8, 129.8, 130.1, 131.9, 132.3, 135.3, 135.5, 136.4, 137.0, 159.2, 172.3; MS (FAB): m/z 689 (MH$^+$), Calculated C$_{41}$H$_{44}$N$_2$O$_6$Si: C, 71.48; H, 6.44; N, 4.07. Found C, 71.38; H, 6.49; N, 4.08.

(5) Synthesis of Compound 7

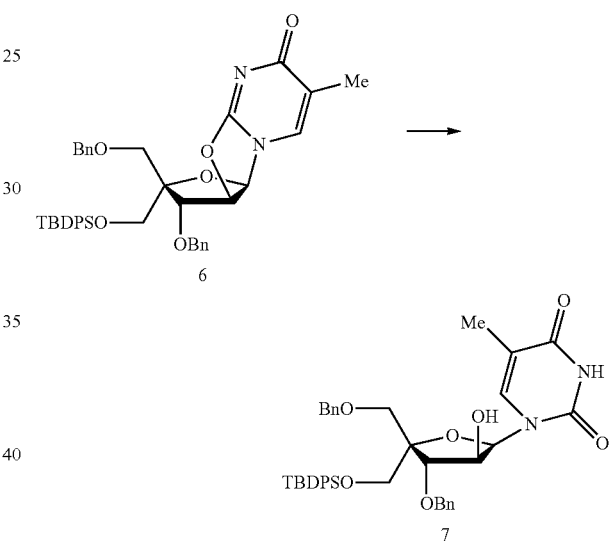

To a solution of compound 6 from (4) above (510 mg, 0.74 mmol) in tetrahydrofuran (11 mL) was added 1N aqueous sodium hydroxide (1.90 mL) and the mixture was stirred for 11.5 hours at room temperature. After neutralization with aqueous ammonium chloride solution, the mixture was concentrated, extracted with dichloromethane, washed with saturated sodium bicarbonate solution and then dried over anhydrous sodium sulphate. After the solvent was distilled away, the resultant crude product was purified by flash column chromatography (n-hexane:ethyl acetate=1:1(v/v)) to give compound 7 (524 mg:yield 100%) as a white amorphous.

The physical property data of the resultant compound 7 was as follows: melting point: 67-70° C.; $[\alpha]_D^{26}$+24.5 (c 0.840, CHCl$_3$); IR (KBr): 3347, 3184, 1690, 1471 cm$^{-1}$; $^1$H-NMR (270 MHz, CDCl$_3$): δ1.02 (9H, s), 1.65 (3H, s), 3.48, 3.70 (2H, AB, J=10.3 Hz), 3.50 (1H, d, J=7.0 Hz), 3.62, 3.76 (2H, AB, J=10.8 Hz), 4.22 (1H, d, J=7.0 Hz,) 4.51, 4.78 (2H, AB, J=7.6 Hz), 4.54 (1H, d, J=11.6 Hz), 4.69 (1H, ddd, J=5.1, 7.0, 7.6 Hz), 6.15 (1H, d, J=5.1 Hz), 7.29-7.64 (20H, m), 8.10 (1H, s); $^{13}$C-NMR (67.80 MHz, CDCl$_3$): δ12.0, 18.8, 26.5, 63.9, 69.7, 72.6, 73.6, 75.3, 81.9, 85.3, 85.5, 109.5, 127.5, 127.6, 127.8, 128.0, 128.2, 128.5, 129.5, 129.6, 132.4, 135.4, 135.5, 136.8, 137.2, 137.9, 151.1, 164.3; MS (FAB):

m/z 707 (MH+), Calculated C$_{41}$H$_{46}$N$_2$O$_7$Si: C, 69.66; H, 6.56; N, 3.96. Found C, 69.42; H, 6.54; N, 3.97.

(6) Synthesis of Compound 9

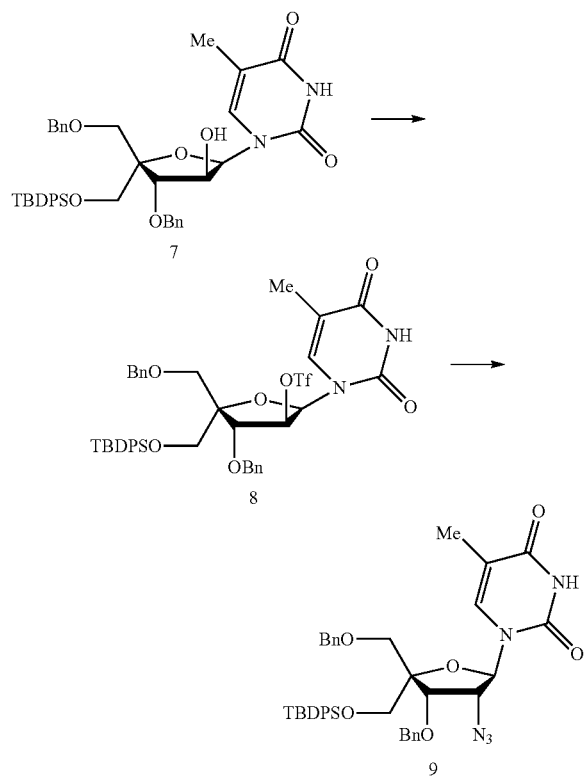

Under nitrogen stream, to a solution of compound 7 from (5) above (2.86 g, 4.10 mmol) in dichloromethane (40 mL) was added pyridine (1.65 mL, 20.5 mmol), trifluoromethanesulfonic anhydride (1.37 mL, 8.20 mmol) on ice cooling and the mixture was stirred for 1 hour in ice-cooling condition. After decomposition of the acid anhydride by addition of water, the mixture was extracted with dichloromethane and the organic layer was then dried over anhydrous sodium sulphate. After the solvent was distilled away, the resultant crude product was given as a yellow oil, which was then simply purified by flash chromatography (n-hexane:ethyl acetate=3:1→2:1(v/v)) to give the crude product of compound 8 as a yellow amorphous.

Then, under nitrogen stream, to a solution of compound 8 (1.96 g, 2.34 mmol) in dimethylformamide (80 mL) was added sodium azide (0.23 g, 3.60 mmol) and the mixture was stirred. After 48 hours, the solvent was distilled away from the mixture to which water was then added, followed by extraction with dichloromethane to obtain the organic layer, which was washed with saturated saline and then dried over anhydrous sodium sulphate. After the solvent was distilled away, the resultant crude product was purified by flash column chromatography (n-hexane:ethyl acetate=3:1) to give compound 9 (1.71 g:yield 66% (2 steps)) as a white amorphous.

The physical property data of the resultant compound 9 was as follows: melting point: 53-56° C.; $[\alpha]_D^{27}$ −32.7 (c 0.840, CHCl$_3$); IR (KBr): 3175, 2109, 1686, 1268, 1111 cm$^{-1}$; $^1$H-NMR (300 MHz, CDCl$_3$): δ0.99 (9H, s), 1.58 (3H, s), 3.63, 3.69 (2H, AB, J=10.5 Hz), 3.69, 3.91 (2H, AB, J=10.5 Hz), 3.91 (1H, dd, J=7.2 Hz, 5.4 Hz), 4.23 (1H, d, J=5.4 Hz), 4.47, 4.53 (2H, AB, J=11.4 Hz), 4.57, 4.75 (2H, AB, J=11.4 Hz), 6.03 (1H, d, J=7.2 Hz), 7.23-7.60 (20H, m), 8.70 (1H, s); $^{13}$C-NMR (75.45 MHz, CDCl$_3$): δ12.1, 19.1, 26.9, 64.0, 64.6, 72.4, 73.8, 74.6, 79.5, 85.2, 87.9, 111.3, 127.7, 127.7, 127.8, 128.0, 128.2, 128.4, 128.7, 129.7, 129.9, 132.5, 132.8, 135.1, 135.5, 135.7, 136.8, 136.9, 150.2, 163.4; MS (FAB): m/z 732 (MH+), Calculated C$_{41}$H$_{45}$N$_5$O$_6$Si: C, 67.28; H, 6.20; N, 9.57. Found C, 67.25; H, 6.27; N, 9.45.

(7) Synthesis of Compound 10

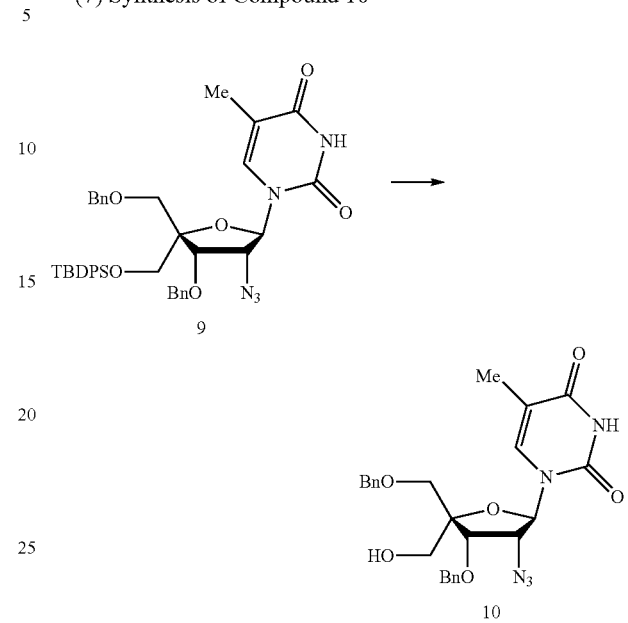

Under nitrogen stream, to a solution of compound 9 of (6) above (1.10 g, 1.50 mmol) in tetrahydrofuran (30 mL) was added 1N solution of tetrabutylammonium fluoride in tetrahydrofuran (2.20 mL, 2.20 mmol) and the mixture was stirred for 12.5 hours. After the solvent was distilled away, water and ethyl acetate were sequentially added and the organic layer was dried over anhydrous sodium sulphate. After the solvent was distilled away, the crude product was purified by flash column chromatography (hexane:ethyl acetate=10:1 (v/v)→100% ethyl acetate) to give compound 10 (682.2 mg:yield 92%) as a white amorphous.

The physical property data of the resultant compound 10 was as follows: melting point: 41-45° C.; $[\alpha]_D^{25}$+13.3 (c 0.950, CHCl$_3$); IR (KBr): 3435, 2113, 1694, 1459, 1268, 1097 cm$^{-1}$; $^1$H-NMR (300 MHz, CDCl$_3$): δ1.63 (3H, s), 2.09 (1H, br), 3.73 (1H, s), 4.04 (1H, t, J=6.3 Hz), 4.39 (1H, d, J=6.3 Hz), 4.51, 4.55 (2H, AB, J=10.2 Hz), 4.56, 4.91 (2H, AB, J=11.4 Hz), 6.18 (1H, d, J=6.3 Hz), 7.26-7.44 (10H, m), 8.50 (1H, s); $^{13}$C-NMR (75.45 Hz, CDCl$_3$): δ12.2, 63.4, 64.9, 71.8, 73.8, 74.8, 79.4, 86.4, 87.5, 111.5, 127.7, 128.2, 128.2, 128.6, 128.7, 128.8, 135.2, 136.5, 137.0, 150.3, 163.5; MS (FAB): m/z 494 (MH+), high-resolution MS (FAB): Calculated C$_{25}$H$_{28}$N$_5$O$_6$ (MH+): 494.2040. Found 494.2045.

(8) Synthesis of Compound 11

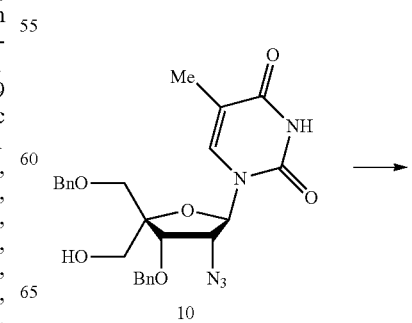

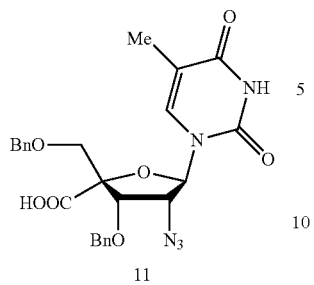

11

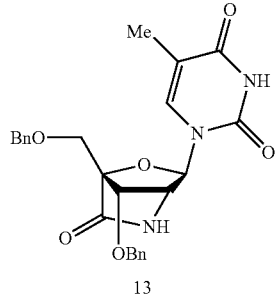

13

Under nitrogen stream, to a solution of compound 10 from (7) above (0.20 g, 0.40 mmol) in dimethylformamide (3.1 mL) was sequentially added molecular sieve powder 4Å (0.31 g) and pyridinium dichromate (1.50 g, 4.00 mmol) and the mixture was stirred at room temperature. After 4.5 hours, water was added to the mixture and stirred for a few minutes, followed by adding acetic acid (2 mL) and further stirring for 1 hour. After diluting with ethyl acetate, the mixture was filtered through Celite and the filtrate was extracted with ethyl acetate. The organic layer was washed with 0.4 M aqueous oxalic acid solution (30 mL) and 0.3 M aqueous ammonium oxalate solution (30 mL) and then dried over anhydrous sodium sulphate. The solvent was distilled away to give compound 11 (0.20 g:yield 100%) as a light yellow solid.

The physical property data of the resultant compound 11 was as follows: $^1$H-NMR (300 MHz, CDCl$_3$): δ1.64 (3H, s), 3.83 (1H, dd, J=8.4, 5.4 Hz), 3.84, 4.12 (2H, AB, J=10.5 Hz), 4.45 (1H, d, J=5.4 Hz), 4.59, 4.65 (2H, AB, J=11.4 Hz), 4.75, 4.82 (2H, AB, J=10.5 Hz), 5.89 (1H, br), 6.54 (1H, d, J=8.4 Hz), 7.28-7.44 (10H, m), 7.99 (1H, s), 9.31 (1H, br); MS (FAB): m/z 508 (MH$^+$), high-resolution MS (FAB): Calculated C$_{25}$H$_{25}$N$_5$O$_7$ (MH$^+$): 508.1832. Found 508.1825.

(9) Synthesis of Compound 13

Compound 11 from (8) above (389.7 mg, 0.77 mmol) was dissolved in a mixed solution of water:tetrahydrofuran=1:3 (5 mL), to which tributylphosphine (0.96 mL, 3.85 mmol) was added and the mixture was stirred at room temperature. After 3.5 hours, the solvent was distilled away from the mixture, which was then dissolved in methanol and washed with hexane. After the solvent was distilled away, the crude product of compound 12 (380 mg) was given as an oil, which was used for the following ring-closing reaction.

Under nitrogen stream, to a solution of compound 12 in DMF (11 mL) was added 1-ethyl-3-(3-dimethylaminopropyl) carbodiimide hydrochloride (221 mg, 1.16 mmol) on ice cooling and the mixture was stirred for 21.5 hours at room temperature. After the solvent was distilled away, the residue was extracted with ethyl acetate and dried over anhydrous sodium sulphate. After the solvent was distilled away, the crude product was purified by column chromatography (hexane:ethyl acetate=5:1 (v/v)→100% ethyl acetate) to give compound 13 (191.3 mg:yield 54% (2 steps)) as an oil.

The physical property data of the resultant compound 13 was as follows: [α]$_D^{25}$ +62.1 (c 0.400, CHCl$_3$); IR (KBr): 3186, 1692, 1469, 1455, 1272, 1112 cm$^{-1}$; $^1$H-NMR (300 MHz, CDCl$_3$): δ1.61 (3H, s), 3.96, 4.11 (2H, AB, J=11.4 Hz), 4.13 (1H, s), 4.22 (1H, s), 4.56 (2H, s), 4.60, 4.67 (2H, AB, J=11.4 Hz), 5.45 (1H, s), 6.58 (1H, br), 7.21-7.56 (10H, m), 7.57 (1H, s), 9.24 (1H, br); $^{13}$C-NMR (67.80 Hz, CDCl$_3$): 12.3, 58.4, 63.0, 72.4, 74.0, 78.3, 86.2, 86.6, 110.9, 127.8, 127.8, 128.1, 128.3, 128.5, 128.6, 135.1, 136.2, 137.4, 142.0, 150.5, 163.8, 174.3; MS (FAB): m/z 464 (MM$^+$).

(10) Synthesis of Compound 14

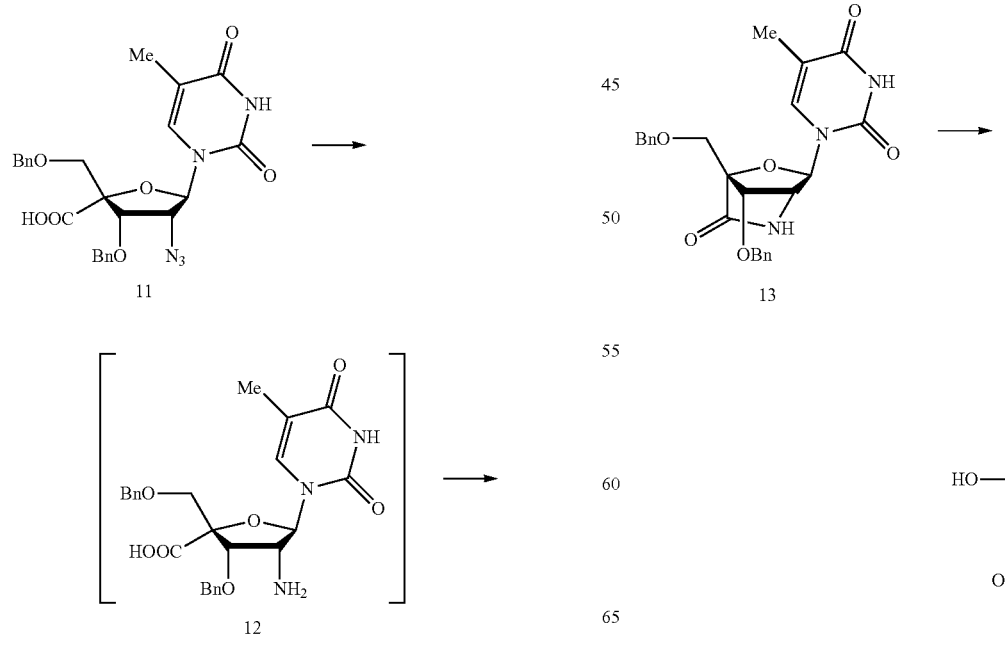

Under nitrogen stream, to a solution of compound 13 from (9) above (101 mg, 0.22 mmol) in tetrahydrofuran (2.2 mL) was added 20% (v/v) palladium hydroxide on carbon (100 mg) and the mixture was stirred for 3 hours under hydrogen stream. After hot filtration and washing with warm methanol (150 mL), solvent was distilled away to give the crude product. The crude product was recrystallized using methanol to give compound 14 (57.2 mg:yield 93%) as a white solid.

The physical property data of the resultant compound 14 was as follows: $[\alpha]_D^{25}$ +31.6 (c 0.700, $CH_3OH$); IR (KBr): 3255, 2925, 2852, 1692, 1466, 1231, 1065 $cm^{-1}$; $^1$H-NMR (300 MHz, $CD_3OD$): δ1.89 (3H, s), 3.88, 4.04 (2H, AB, J=12.9 Hz), 4.12 (1H, s), 4.30 (1H, s), 5.38 (1H, s), 7.86 (1H, s).

(11) Synthesis of Compound 15

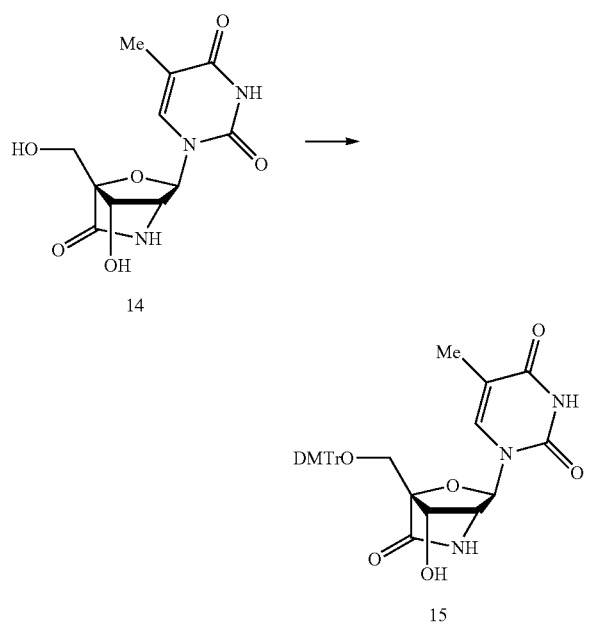

Under nitrogen stream, to a solution of compound 14 from (10) above (27.3 mg, 0.10 mmol) in anhydrous pyridine (0.8 mL) was added 4,4'-dimethoxytrityl chloride (48.8 mg, 0.14 mmol) and the mixture was stirred for 3 hours. After adding sodium bicarbonate solution, stirring for a few minutes and distilling away the solvent, the residue was extracted with saturated sodium bicarbonate solution/ethyl acetate to recover the organic layer which was then dried over anhydrous sodium sulphate. After the solvent was distilled away, the crude product was purified by flash column chromatography (n-hexane:ethyl acetate=10:1 (v/v)→400% ethyl acetate) to give compound 15 (47.6 mg:yield 85%) as a white foam.

The physical property data of the resultant compound 15 was as follows: melting point: 79-81° C.; IR (KBr): 3342, 3063, 2928, 1690, 1509, 1270, 1253, 1177, 1035 $cm^{-1}$; $^1$H-NMR (300 MHz, $CDCl_3$): δ1.66 (3H, s), 3.61, 3.92 (2H, AB, J=12.8 Hz), 3.78 (6H, s), 4.26 (1H, s), 4.46 (1H, s), 5.42 (1H, s), 6.86-7.45 (13H, m), 7.78 (1H, s); MS (FAB): ink 586 ($MH^+$).

(12) Synthesis of Compound 16

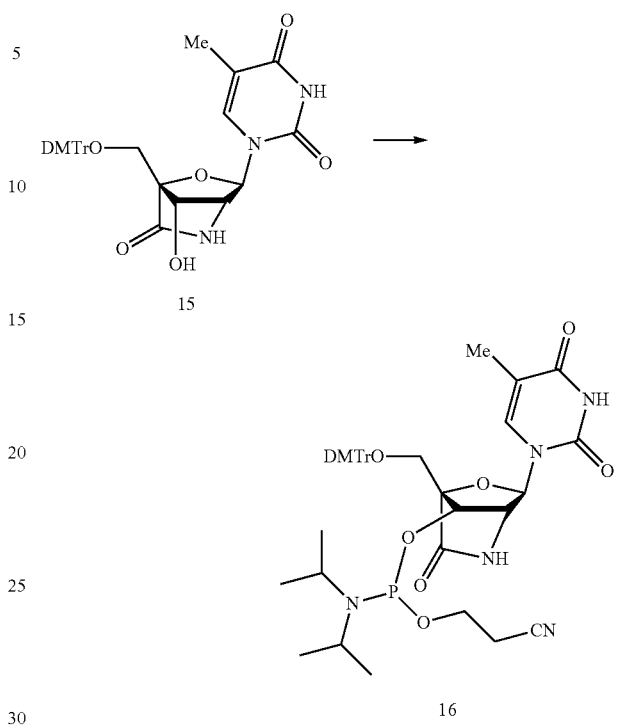

Under nitrogen stream, to a solution of compound 15 from (11) above (100 mg, 0.17 mmol) in anhydrous acetonitrile-tetrahydrofuran (3:1 (v/v)) (2.0 mL) was added N, N-diisopropyl ammonium tetrazolide (22.2 mg, 0.13 mmol) and 2-cyanoethyl N,N,N',N'-tetraisopropyl phosphordiamidite (54.0 μL, 0.17 mmol) and the mixture was stirred. After 1.5 hours, saturated sodium bicarbonate solution was added to the mixture, which was stirred for a few minutes and then extracted with water/ethyl acetate to recover the organic layer which was then dried over anhydrous sodium sulphate. After the solvent was distilled away, the residue was purified by flash column chromatography (dichloromethane:methanol:triethylamine=50:1:1 (v/v/v)) to give the crude product. The resultant crude product was dissolved in dichloromethane and added to n-hexane for reprecipitation to give compound 16 (29.4 mg, 22%) as a white powder.

The physical property data of the resultant compound 16 was as follows: melting point: 110-112° C. ($CH_2Cl_2$); $^{31}$P-NMR (202.35 MHz, $CDCl_3$): δ149.74, 150.12; MS (FAB): m/z 786 ($MH^+$), high-resolution MS (FAB): Calculated $C_{41}H_{49}N_5O_9$ ($MH^+$): 786.3268. Found 786.3266.

Example 2

Synthesis and Purification of Oligonucleotide Analogues

10mer of the oligonucleotide analogues containing compound 16 from Example 1 above (compounds 17-20: showed in Table 1 below) were synthesized using Expedite™ 8909 (from ABI) in the scale of 0.2 μmol. In this synthesis, the capping step in the standard phosphoramidite protocol was skipped. The compound 16 (amidite unit) was dissolved in tetrahydrofuran to use in the synthesis. In Table 1, the compound 16 is indicated by X. Duration of the coupling reaction between an amidite unit (compound 16) and a hydroxyl group at 5'-terminus was extended from 1.5 minutes (standard condition) to 20 minutes. The oligonucleotide analogues with 5'-terminus protected with a DMTr group supported on a solid phase were treated with 0.05 M solution of potassium carbonate in methanol and then neutralized with 5% (w/v) hydrochloric acid, after which the solvent was distilled away. The resultant crude product was partially purified by the gel filtration column NAP™ 10 Column (GE Health Care) and then purified by reversed-phase HPLC(SHIMADZU LC-10AT$_{VP}$, SHIMADZU SPD-10A$_{VP}$, SHIMADZU CTO-10$_{VP}$, using Waters X Terra® (10 mm×50 mm) as a preparative column).

The purities of the synthesized oligonucleotide analogues (compounds 17-20) were determined by reversed-phase HPLC (Waters X Terra® MS $C_{18}$ 2.5 μm, 4.6 mm×50 mm)) (condition: gradient 7→13% (v/v) acetonitrile in 0.1 M triethyl ammonium acetate buffer (pH 7.0), 1 mL/min for 30 minutes). The molecular weights were determined by MALDI-TOF-MASS. The results are shown in Table 1.

TABLE 1

| Oligonucleotide | | MALDI-TOF-MASS | |
|---|---|---|---|
| | | Calculated (M − H$^-$) | Found (M − H$^-$) |
| 5'-TTTTTXTTTT-3' | (Compound 17) | 3019.97 | 3020.35 |
| 5'-TTTXTXTTTT-3' | (Compound 18) | 3059.98 | 3058.99 |
| 5'-TTTXTXTXTT-3' | (Compound 19) | 3099.99 | 3098.99 |
| 5'-TTTTTTTTXT-3' | (Compound 20) | 3019.97 | 3019.32 |

Example 3

Determination of the Melting Temperature (Tm)

After compounds 17-19 and 21-24 (antisense strands), which were the oligonucleotide strands synthesized in Example 2 above, and sense strands (3'-AAAAAAAAAA-5') were subjected to an annealing treatment, their Tm values were measured to determine the hybridization ability of the antisense strands. The Tm value means the temperature at which 50% of the double-stranded nucleic acids dissociate into single strands and the higher Tm value means the stronger binding force between the strands constituting the double-stranded nucleic acid.

The sample solution (130 μL) containing 100 mM NaCl, 10 mM sodium phosphate buffer (pH 7.2), 4 μM antisense strands and 4 μM sense strands was heated in a boiled water bath and then cooled to room temperature over 10 hours. Nitrogen stream was passed into a cell chamber of a spectrophotometer (Shimadzu, UV-1650PC) for dew condensation prevention and the sample solution was gradually cooled to 5° C. and kept at 10° C. for 20 minutes before starting the measurements. The temperature was raised to 85° C. at the rate of 0.5° C./min while ultraviolet absorption spectra were measured at 260 nm at intervals of 0.1° C. Lidded cells were used to prevent concentration change due to rising temperature. The results are shown in Table 2.

TABLE 2

| | | Sense strand | | | |
|---|---|---|---|---|---|
| | | RNA complementary strand | | DNA complementary strand | |
| Antisense strand | | Tm (° C.) | Δ Tm/mod. (° C.) | Tm (° C.) | Δ Tm/mod. (° C.) |
| 5'-TTTTTTTTTT-3' | (Compound 21) | 18.8 | | 22.9 | |
| 5'-TTTTTYTTTT-3' | (Compound 22) | 25.5 | +6.7 | 23.9 | +1.3 |
| 5'-TTTTTXTTTT-3' | (Compound 17) | 24.9 | +6.2 | 22.0 | −0.9 |
| 5'-TTTYTYTTTT-3' | (Compound 23) | 35.1 | +8.2 | 29.7 | +3.4 |
| 5'-TTTXTXTTTT-3' | (Compound 18) | 33.7 | +7.5 | 24.4 | +0.8 |
| 5'-TTTYTYTYTT-3' | (Compound 24) | 41.5 | +7.6 | 36.6 | +4.6 |
| 5'-TTTXTXTXTT-3' | (Compound 19) | 41.7 | +7.7 | 32.2 | +3.1 |

Δ Tm/mod. = Δ Tm/modified base

The oligonucleotides containing natural forms of oligonucleotides (compound 21) (shown in Table 2 below), and the oligonucleotide analogues containing known 2',4'-BNA/LNA (5-methyl-2'-O, 4'-C-methyleneuridine (synthesized according to Non-patent Document 6) (compounds 22-24: shown in Table 2 below) were also synthesized according to the standard phosphoramidite protocol and purified as described above for comparison. In Table 2, 2',4'-BNA/LNA is indicated by Y.

As shown in Table 2, the oligonucleotide analogues of the invention have higher affinities to single-stranded RNAs than to single-stranded DNAs and their affinities were comparable to known 2',4'-BNA/LNA. Also, the more artificial nucleic acids introduced into an oligonucleotide, the higher Tm value it has. Therefore, the nucleotide analogues of the invention are believed to be as useful for the synthesis of oligonucleotides suitable for antisense therapies as 2',4'-BNA/LNA.

Example 4
Synthesis of Nucleoside Analogue: 2'-amino-2'-deoxy-2'-N,4'-C-oxomethyleneadenosine (Compound 34)
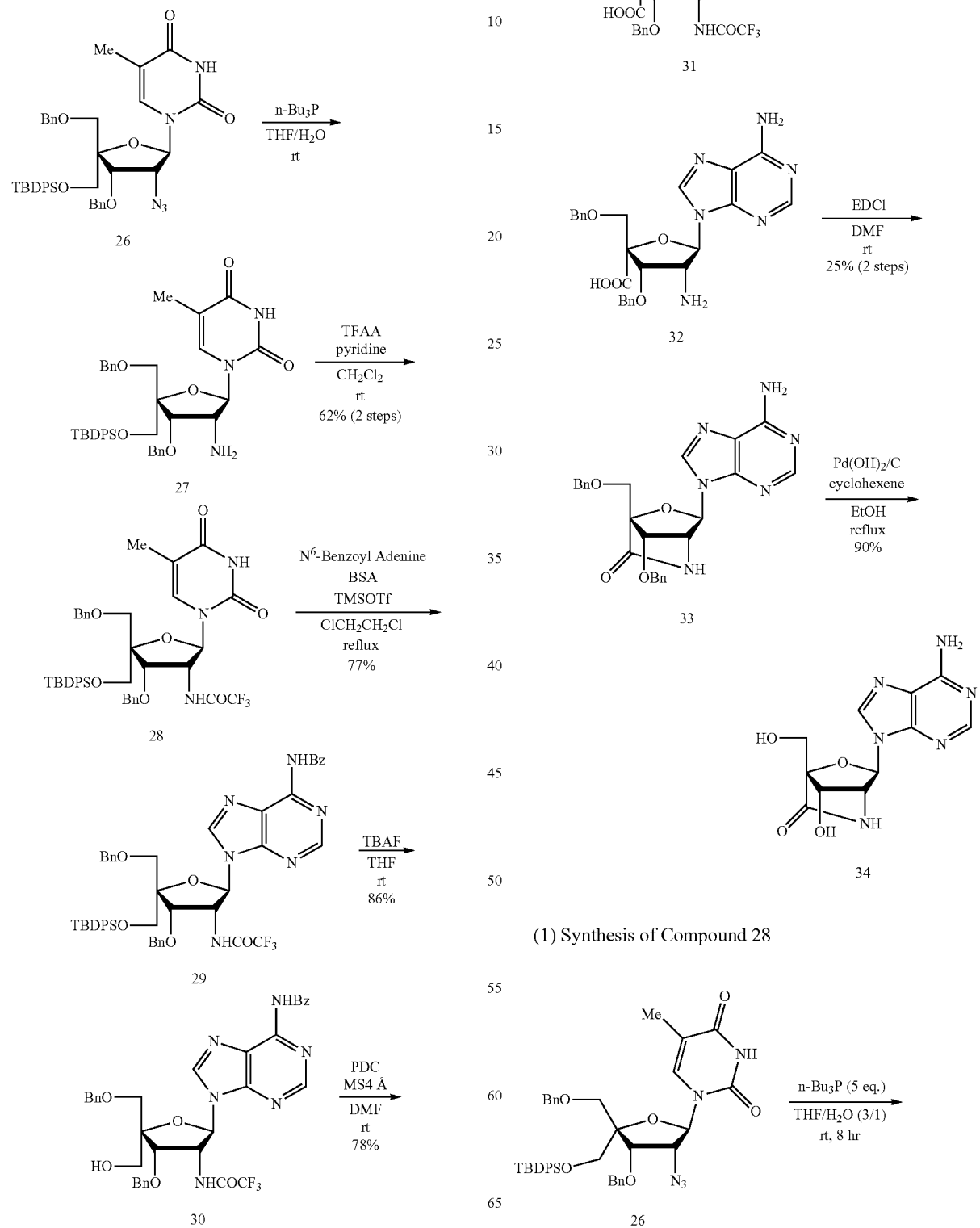
(1) Synthesis of Compound 28

(2) Synthesis of Compound 29

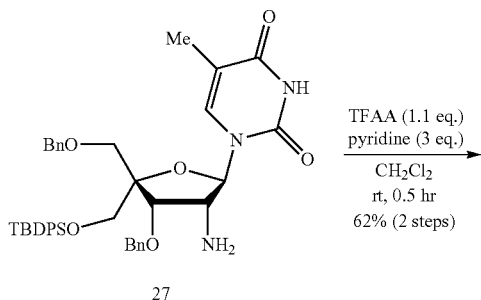
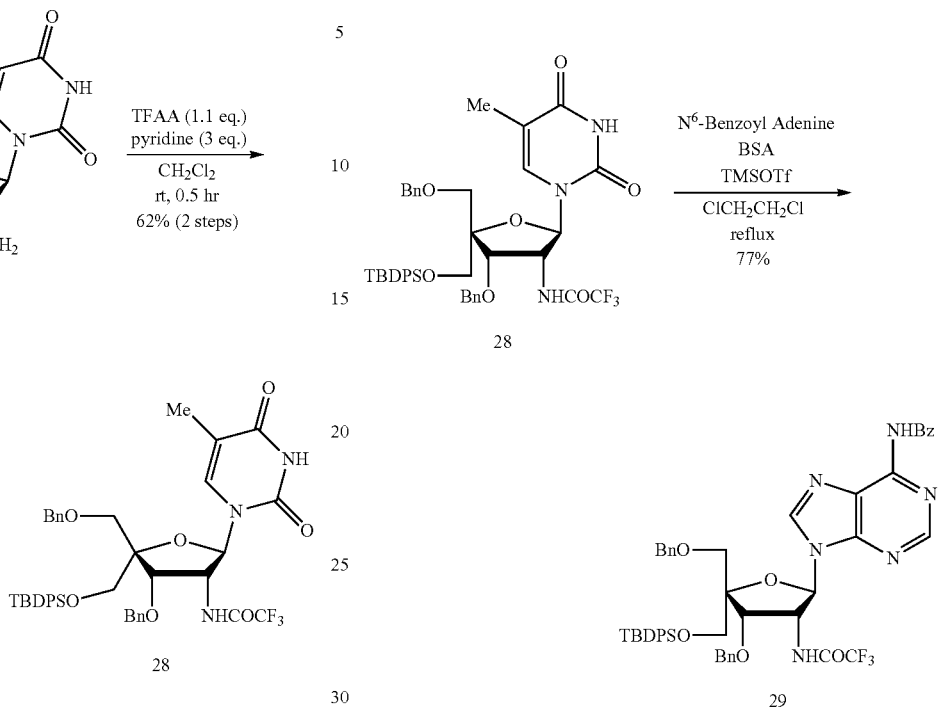

Under nitrogen stream, compound 26 (500 mg, 0.68 mmol) was dissolved in the solution of water:tetrahydrofuran=1:3 (v/v) (4.5 mL), to which tributylphosphine (0.85 mL, 3.42 mmol) was added and stirred for 8 hours at room temperature. After the solvent was distilled away, the residue was dissolved in methanol and washed with hexane. After the solvent was distilled away, the crude product 27 was given as an oil, which was then simply purified by column chromatography (hexane:ethyl acetate=5:1→2:1(v/v)) before application for the next reaction.

Under nitrogen stream, to a solution of crude product 27 in dichloromethane (6 mL) was added pyridine (0.16 mL, 2.05 mmol). After ice-cooling, trifluoroacetic anhydride (0.10 mL, 0.75 mL) was added to the mixture and stirred for 0.5 hours. Water was then added to the mixture, which was then extracted with dichloromethane, and the extract was washed with aqueous sodium hydrogen carbonate solution and dried over anhydrous sodium sulphate. After the solvent was distilled away, the resultant crude product was purified by column chromatography (hexane:ethyl acetate=5:1→2:1(v/v)) to give compound 28 (341.4 mg:yield 62% (2 steps)) as a white foam.

The physical property data of the resultant compound 28 was as follows: IR (KBr): 3185, 2961, 1713, 1211, 1158, 1094 cm$^{-1}$; $^1$H-NMR (300 MHz, CDCl$_3$): δ1.04 (9H, s), 1.59 (3H, s), 3.54, 3.78 (2H, AB, J=10 Hz), 3.65, 4.02 (2H, AB, J=10.5 Hz), 4.28 (1H, d, J=5.5 Hz), 4.55, 4.71 (2H, AB, J=11 Hz), 4.58, 4.63 (2H, AB, J=12 Hz), 4.94 (1H, dd, J=5.5 Hz, 8 Hz), 6.22 (1H, d, J=8 Hz), 7.19-7.84 (20H, m), 8.68 (1H, s); $^{13}$C-NMR (100.53 MHz, CDCl$_3$): δ12.1, 19.1, 27.0, 55.9, 63.7, 73.0, 75.4, 79.6, 85.0, 88.2, 112.1, 115.4, 127.7, 127.8, 128.1, 128.1, 128.2, 128.5, 128.7, 129.8, 151.1, 157.8, 163.9; MS (FAB): m/z 802 (MH$^+$), high-resolution MS (FAB): Calculated C$_{43}$H$_{47}$F$_3$N$_3$O$_7$Si (MH): 802.3135. Found 802.3143.

Under nitrogen stream, to a solution of compound 28 from (1) above (103 mg, 0.13 mmol) in dichloroethane (2.5 mL) was added N$^6$— benzoyladenine (80.4 mg, 0.34 mmol) and N,O— bis trimethylsilyl acetamide (246 μL, 1.01 mmol) and heated and stirred until clear. After the reactant was cooled to ambient temperature, trimethylsilyl trifluoromethane-sulfonate (16.3 μL, 0.09 mmol) was added to the reactant and stirred at reflux for 3.5 hours. Then saturated sodium bicarbonate solution was added to the reactant which was then extracted with dichloromethane, and the organic layer was washed with water and then sodium bicarbonate water and then dried over anhydrous sodium sulphate. After the solvent was distilled away, the resultant crude product was purified by column chromatography (hexane:ethyl acetate=5:1→3:1(v/v)) to give compound 29 (90.3 mg:yield 77%) as a white foam.

The physical property data of the resultant compound 29 was as follows: IR (KBr): 3402, 3246, 3068, 2931, 2858, 1722, 1638, 1218, 1105 cm$^{-1}$; $^1$H-NMR (300 MHz, CDCl$_3$): δ1.06 (9H, s), 3.54, 3.83 (2H, AB, J=10 Hz), 3.78, 4.10 (2H, AB, J=11 Hz), 4.44 (1H, d, J=6 Hz), 4.51, 4.66 (2H, AB, J=11.5 Hz), 4.54, 4.76 (2H, AB, J=11 Hz), 5.29 (1H, dd, J=6 Hz, 7.5 Hz), 6.11 (1H, d, J=7.5 Hz), 7.16-8.02 (25H, m), 8.26 (1H, s), 8.70 (1H, s); $^{13}$C-NMR (100.53 MHz, CDCl$_3$): δ19.1, 26.9, 56.4, 63.4, 72.0, 73.8, 75.5, 79.7, 86.1, 89.1, 122.9, 127.8, 128.0, 128.2, 128.3, 128.6, 128.7, 128.8, 129.9, 130.0, 132.3, 132.6, 132.6, 133.6, 135.5, 135.7, 136.3, 136.9, 141.1, 149.5, 151.7, 152.6, 157.1, 164.6; MS (FAB): m/z 915 (MH$^+$), high-resolution MS (FAB): Calculated C$_{50}$H$_{50}$F$_3$N$_6$O$_6$Si (MH): 915.3513. Found 915.3537.

(3) Synthesis of Compound 30

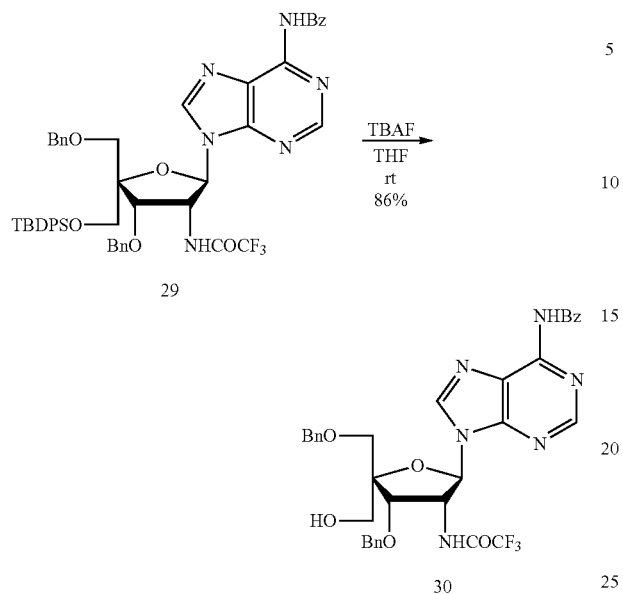

Under nitrogen stream, to a solution of compound 29 from (2) above (40 mg, 0.044 mmol) in tetrahydrofuran (1.0 mL) was added tetra-n-butylammonium fluoride (1 M tetrahydrofuran solution, 49 μL, 0.049 mmol) and the mixture was stirred for 15 minutes at room temperature. After the solvent was distilled away, water was added to the residue which was then extracted three times with ethyl acetate, and the organic layer was washed with saturated saline and then dried over sodium sulfate. After the solvent was distilled away under reduced pressure, the resultant crude product was purified by column chromatography (2 g, n-hexane:ethyl acetate=2:1→2:3) to give compound 30 (25.5 mg:yield 86%) as a white foam.

The physical property data of the resultant compound 30 was as follows: $[\alpha]_D^{26}$ −15.9 (c 1.00, CHCl$_3$); IR (KBr): 3395, 2928, 3271, 1722, 1613, 1216, 1184 cm$^{-1}$; $^1$H-NMR (300 MHz, CDCl$_3$): δ1.60 (1H, s), 3.24 (1H, s), 3.40, 3.47 (2H, AB, J=10 Hz), 3.78, 3.91 (2H, AB, J=11.5 Hz), 4.33 (2H, s), 4.52, 4.62 (2H, AB, J=11.5 Hz), 4.89 (1H, d, J=6.0 Hz), 5.41 (1H, d, J=6.0 Hz), 6.33 (1H, s), 7.12-7.71 (13H, m), 8.02 (2H, d, J=7.5 Hz), 8.25 (1H, s), 8.68 (1H, s), 9.44 (1H, s); MS (FAB): m/z 677 (MH$^+$), high-resolution MS (FAB): Calculated C$_{34}$H$_{32}$F$_3$N$_6$O$_6$ (MH): 677.2335. Found 677.2349.

(4) Synthesis of Compound 31

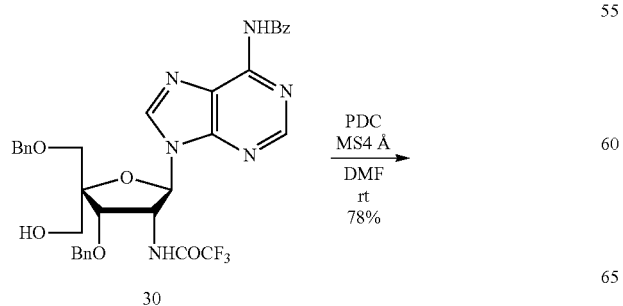

Under nitrogen stream, compound 30 from (3) above (213 mg, 0.315 mmol) was dissolved in dimethylformamide (1.5 mL), to which pyridinium dichromate (872 mg, 3.15 mmol) and 300 mg of molecular sieves 4Å were added, and the mixture was stirred for 17 hours at room temperature. Water and then acetic acid (1.5 mL) was added to the mixture which was then stirred, diluted with ethyl acetate and then filtered through Celite. The filtrate was extracted with ethyl acetate and the organic layer was washed with oxalate buffer and then dried over sodium sulfate. After the solvent was distilled away, the crude product 31 was given as a white solid (169 mg:yield 78%).

The physical property data of the resultant compound 31 was as follows: $[\alpha]_D^{25}$ −43.8 (c 1.000, CHCl$_3$); IR (KBr): 3256, 3061, 2923, 2871, 1725, 1613, 1584, 1218, 1173 cm$^{-1}$; $^1$H-NMR (400 MHz, CDCl$_3$): δ3.76, 3.97 (2H, AB, J=10.6 Hz), 4.41, 4.60 (2H, AB, J=11.4 Hz), 4.44, 4.54 (2H, AB, J=12.0 Hz), 4.63 (1H, d, J=6.5 Hz), 5.19 (1H, dd, J=6.5 Hz, 8.7 Hz), 6.40 (1H, d, J=6.5 Hz), 7.17-7.58 (13H, m), 7.99 (2H, d, J=7.8 Hz), 8.37 (1H, s), 8.56 (1H, s), 9.57 (1H, s); $^{13}$C-NMR (100.53 MHz, CDCl$_3$): δ55.8, 70.4, 73.8, 75.3, 78.7, 87.7, 90.4, 116.7, 122.6, 127.9, 128.2, 128.4, 128.6, 128.7, 133.0, 135.8, 136.6, 141.9, 149.5, 151.8, 157.4, 165.2.

(5) Synthesis of Compound 33

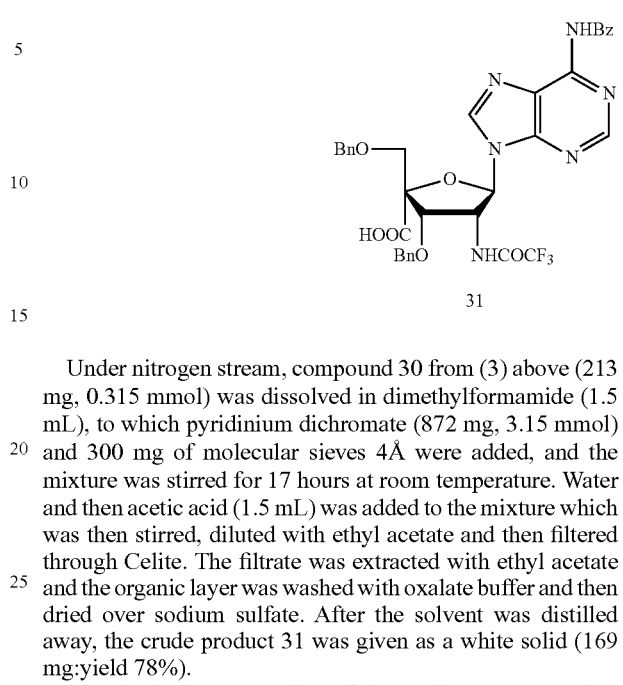

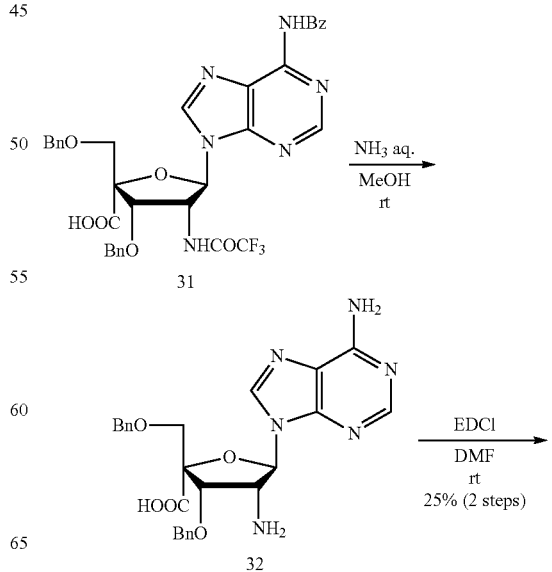

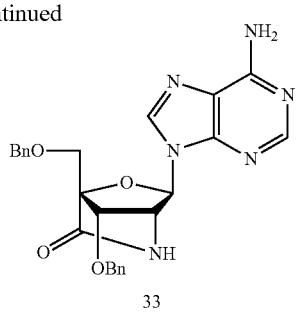

33

Under nitrogen stream, compound 31 from (4) above (1.09 g, 1.58 mmol) was dissolved in methanol (15 mL), to which 28% (v/v) aqueous ammonia (10 mL) was added at room temperature, and then stirred for 19 hours. After the solvent was distilled away, the residue was extracted with ethyl acetate/water to recover the aqueous layer from which the solvent was then distilled away. The resultant powdery crude product 32 was azeotroped with acetonitrile before applying to the next reaction.

The crude product 32 (766 mg, 1.56 mmol) was dissolved in dimethylformamide (20 mL), to which 1-ethyl-3-(3-dimethylaminopropyl) carbodiimide hydrochloride (299 mg, 1.87 mmol) was added, and then stirred at room temperature for 16 hours. After the solvent was distilled away, the residue was extracted with ethyl acetate and dried over anhydrous sodium sulphate. After the solvent was distilled away, the resultant crude product was purified by column chromatography (chloroform:methanol=20:1 (v/v)) to give the white solid 33 (185 mg:yield 25% (2 steps)).

The physical property data of the resultant compound 33 was as follows: $^1$H-NMR (400 MHz, CDCl$_3$): δ3.94, 4.07 (2H, AB, J=12 Hz), 4.31 (1H, s), 4.43, 4.54 (2H, AB, J=12 Hz), 4.48 (1H, s), 4.63, 4.72 (2H, AB, J=12 Hz), 5.61 (2H, s), 5.85 (1H, s), 6.01 (1H, s), 7.00-7.52 (10H, m), 8.15 (1H, s), 8.32 (1H, s).

(6) Synthesis of Compound 34

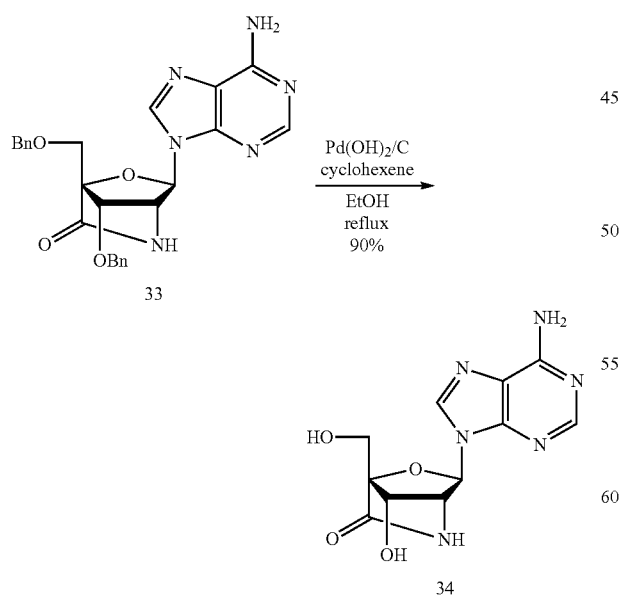

Under nitrogen stream, compound 33 from (5) above (33.6 mg, 0.071 mmol) was dissolved in ethanol (1 mL), to which 20% palladium hydroxide on carbon (33 mg) and cyclohexene (1 mL) was added, and then heated at reflux for 4 hours under nitrogen stream. After the reactant was spontaneously filtered and washed with warm methanol, the solvent was distilled away. The resultant crude product was purified by column chromatography (chloroform:methanol=10:1) to give a white solid 34 (18.7 mg:yield 90%).

The physical property data of the resultant compound 34 was as follows: $^1$H-NMR (400 MHz, CD$_3$OD): δ3.82, 3.98 (2H, AB, J=12 Hz), 4.34 (1H, s), 4.40 (1H, s), 5.76 (1H, s), 8.12 (1H, s), 8.26 (1H, s).

Example 5

Synthesis of the Nucleoside Analogue: 2'-amino-3'-O-[2-cyanoethoxy(diisopropylamino) phosphino]-5'-O-dimethoxytrityl-2'-N,4'-C-oxoethylenethymidine (Compound 51: Amide 6NH)

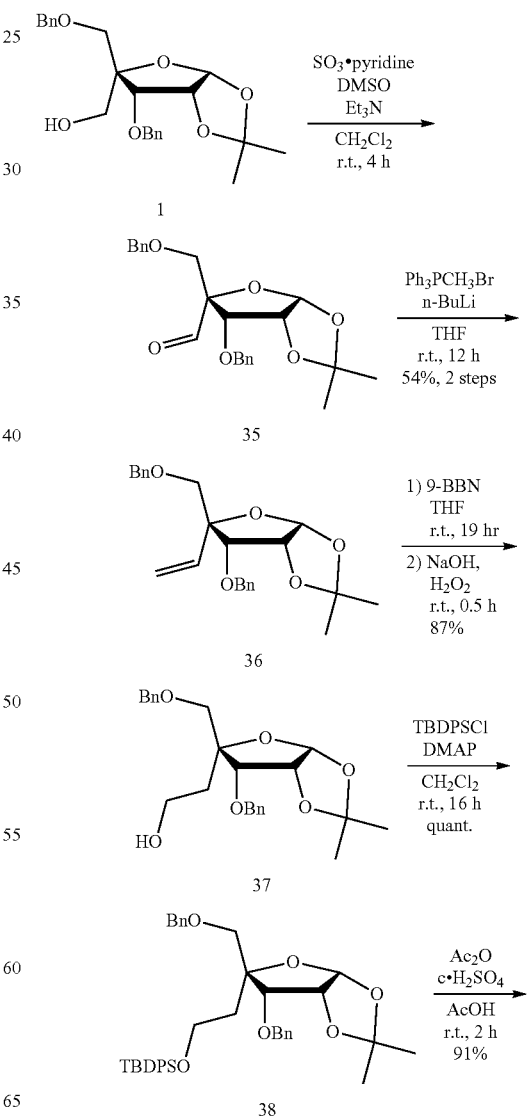

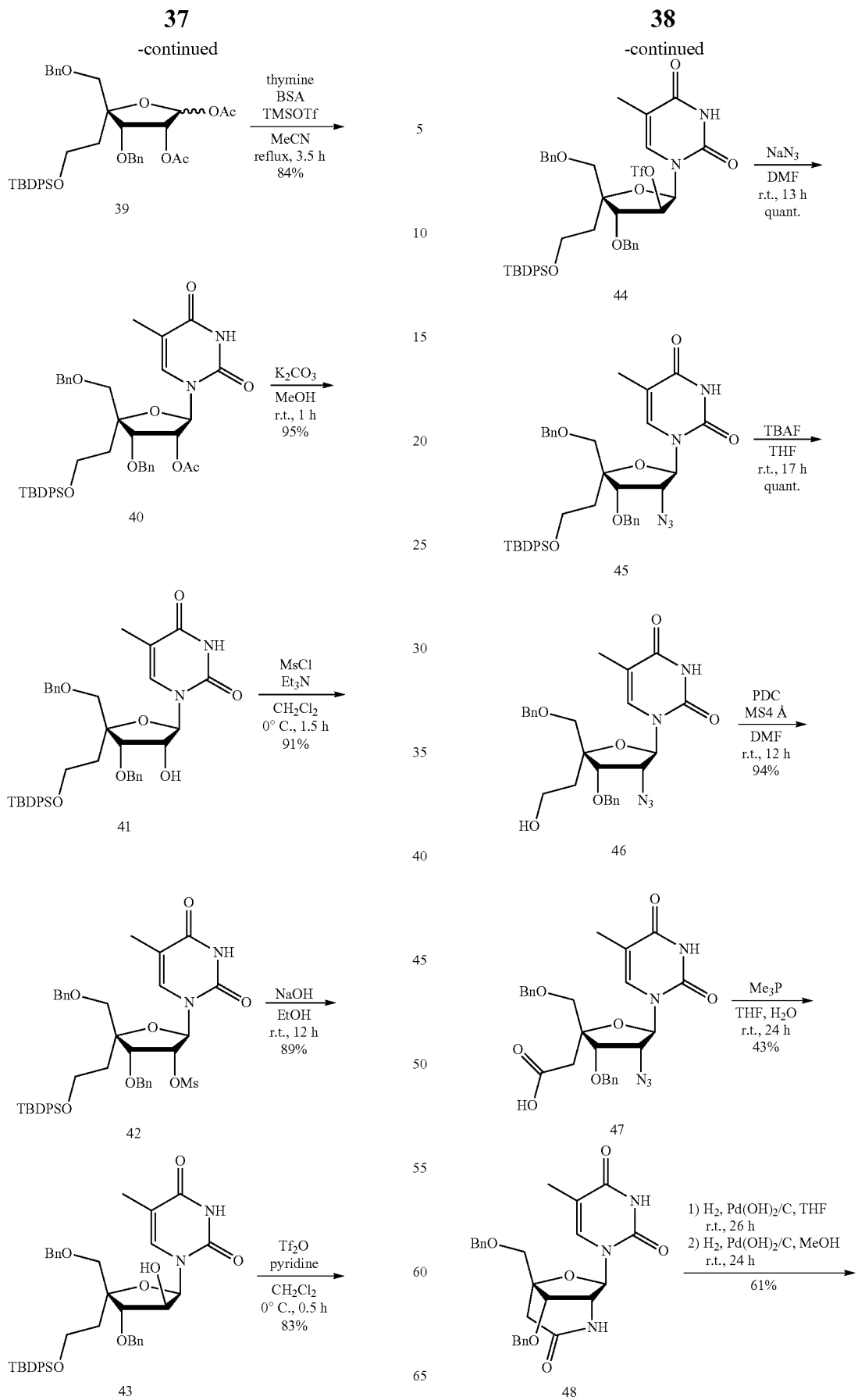

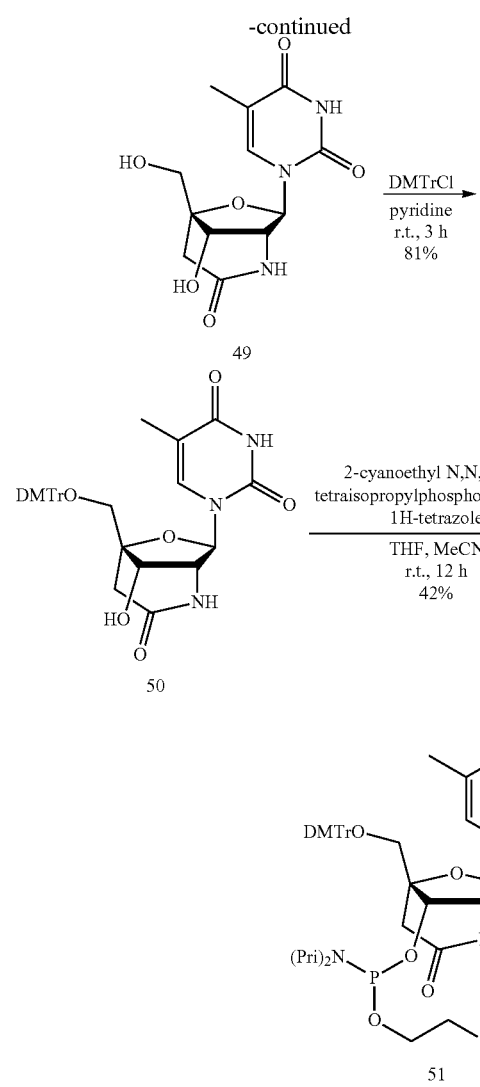

(1) Synthesis of Compound 35

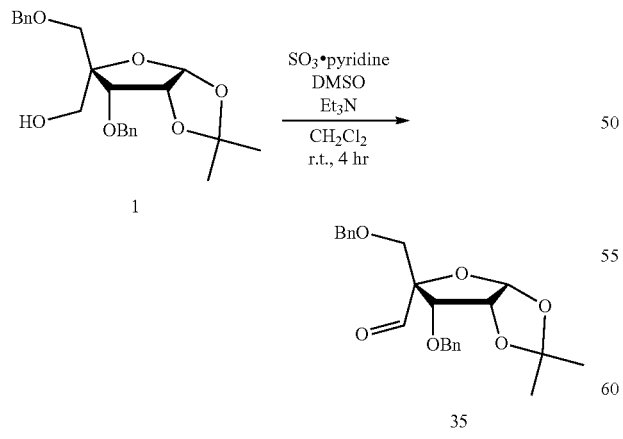

Under nitrogen stream, to a solution of compound 1 (6.03 g, 15.1 mmol) in anhydrous dichloromethane (150 mL) was added dimethyl sulfoxide (13.0 mL, 181 mmol), triethylamine (8.50 mL, 60.2 mmol) and sulfur trioxide pyridine complex (9.60 g, 60.2 mmol) and the mixture was stirred for 4 hours at room temperature. The reaction was quenched by adding water to the reactant which was then diluted with diethyl ether and extracted three times. The organic layer was recovered and washed three times with water and once with saturated saline and then dried over sodium sulfate. The solvent was distilled away under reduced pressure to give the crude product of compound 35 (4.29 g).

(2) Synthesis of Compound 36

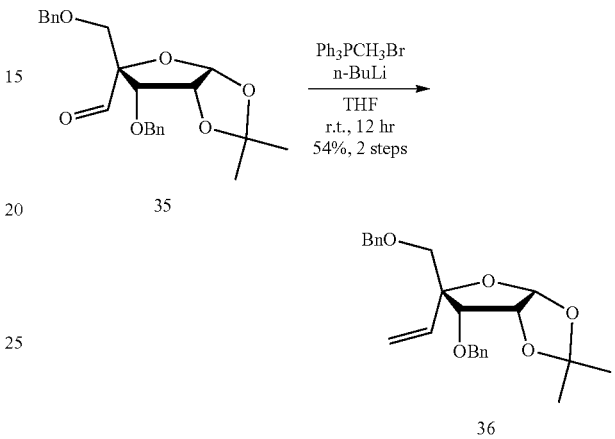

Under nitrogen stream, to the suspension of methyltriphenyl phosphonium bromide (11.5 g, 32.3 mmol) in anhydrous tetrahydrofuran (30 mL) was added dropwise n-butyllithium (1.6 M n-hexane solution, 27.0 mL, 43.1 mmol) at 0° C. and the mixture was stirred for 1 hour at room temperature. The solution of crude product of compound 35 from (1) above in anhydrous tetrahydrofuran (100 mL) was added dropwise to the reactant which was then stirred at room temperature for 12 hours. The reaction was quenched by adding aqueous ammonium chloride solution to the reactant which was then extracted three times with diethyl ether and dried over sodium sulfate. After the solvent was distilled away under reduced pressure, the resultant crude product (8.91 g) was purified by silica-gel column chromatography (150 g, n-hexane:ethyl acetate=5:1 (v/v)) to give compound 36 (3.22 g:yield 54% (2 steps)) as a colorless oil.

The physical property data of the resultant compound 36 was as follows: $^1$H-NMR (400 MHz, CDCl$_3$): δ1.27 (s, 3H), 1.51 (s, 3H), 3.30, 3.32 (AB, J=12.5 Hz, 2H), 4.24 (d, J=5.0 Hz, 1H), 4.50, 4.39 (AB, J=12.5 Hz, 2H), 4.55-4.59 (m, 2H), 4.75 (AB, J=12.5 Hz, 1H), 5.23 (d, J=11.0 Hz, 1H), 5.51 (d, J=17.5 Hz, 1H), 5.75 (d, J=4.0 Hz, 1H), 6.18 (dd, J=11.0, 17.5 Hz, 1H), 7.20-7.38 (m, 10H).

(3) Synthesis of Compound 37

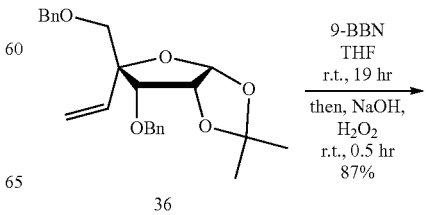

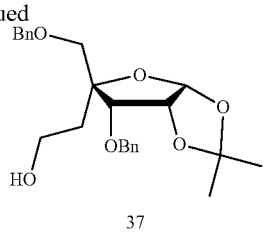

Under nitrogen stream, to a solution of compound 36 from (2) above (4.36 g, 11.0 mmol) in anhydrous tetrahydrofuran (150 mL) was added dropwise borabicyclononane (0.5 M tetrahydrofuran solution, 66 mL, 33.0 mmol) and the mixture was stirred for 19 hours at room temperature. The reaction was quenched by adding water to the reactant, to which aqueous sodium hydroxide (3 M, 23.0 mL, 70.4 mmol) and 35% (v/v) hydrogen peroxide solution (6.0 mL, 70.4 mmol) were added, and stirred for 0.5 hours at room temperature. After completion of the reaction, the reaction mixture was extracted three times with ethyl acetate to recover the organic layer which was then dried over sodium sulfate. After the solvent was distilled away under reduced pressure, the resultant crude product (7.43 g) was purified by silica-gel column chromatography (100 g, n-hexane:ethyl acetate=3:1 (v/v)) to give compound 37 (3.96 g:yield 87%) as a colorless oil.

The physical property data of the resultant compound 37 was as follows: $^1$H-NMR (400 MHz, CDCl$_3$): δ1.32 (s, 3H), 1.64 (s, 3H), 1.77 (ddd, J=4.0, 6.5, 15.5 Hz, 1H), 2.50 (ddd, J=4.0, 8.5, 15.5 Hz, 1H), 2.85 (s, 1H), 3.29, 3.53 (AB, J=10.0 Hz, 2H), 3.72-3.85 (m, 2H), 4.11 (d, J=5.5 Hz, 1H), 4.42, 4.50 (AB, J=12.5 Hz, 2H), 4.53, 4.76 (AB, J=12.0 Hz, 2H), 4.64 (dd, J=4.0, 5.5 Hz, 1H), 5.76 (d, J=4.0 Hz, 1H), 7.23-7.33 (m, 10H).

(4) Synthesis of Compound 38

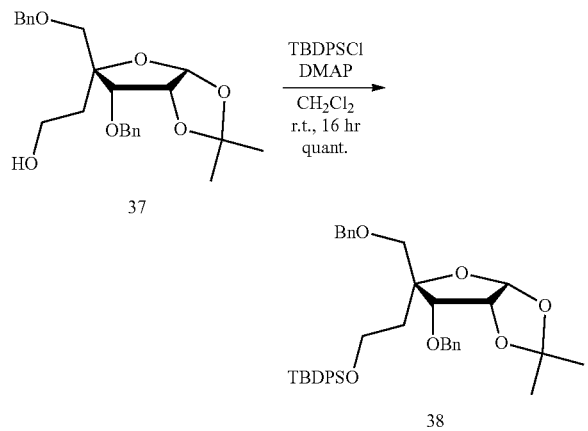

Under nitrogen stream, to a solution of compound 37 from (3) above (3.96 g, 9.56 mmol) in dichloromethane (100 mL) was added N,N-dimethyl-4-aminopyridine (350 mg, 2.87 mmol) and triethylamine (4.0 mL, 28.7 mmol) and then added dropwise tert-butyldiphenylchlorosilane (4.0 mL, 15.3 mmol) at 0° C., and the reactant was stirred for 16 hours at room temperature. The reaction was quenched by adding water to the reactant which was then extracted three times with dichloromethane and dried over sodium sulfate. After the solvent was distilled away under reduced pressure, the resultant crude product (8.82 g) was purified by silica-gel column chromatography (200 g, n-hexane:ethyl acetate=10:1 (v/v)) to give compound 38 (6.28 g: quantitative) as a colorless oil.

The physical property data of the resultant compound 38 was as follows: $[α]_D^{25}$ +16.3 (c 1.00, CHCl$_3$); IR (KBr): 3068, 3031, 2932, 2857, 1454, 1428, 1382, 1209 cm$^{-1}$; $^1$H-NMR (400 MHz, CDCl$_3$): δ0.99 (s, 9H), 1.28 (s, 3H), 1.53 (s, 3H), 1.85 (ddd, J=7.0, 8.0, 14.5 Hz, 1H), 2.43 (ddd, J=5.0, 6.5, 14.5 Hz, 1H), 3.28, 3.69 (AB, J=10.5 Hz, 2H), 3.83-3.94 (AB, m, 2H), 4.20 (d, J=5.5 Hz, 2H), 4.33, 4.46 (AB, J=12.5 Hz, 2H), 4.58 (dd, J=3.5, 5.5 Hz, 1H), 4.52, 4.73 (AB, J=12.5 Hz, 2H), 5.74 (d, J=3.5 Hz, 1H), 7.17-7.68 (m, 20H); $^{13}$C-NMR (100 MHz, CDCl$_3$): δ19.2, 26.3, 26.7, 26.9, 35.0, 59.9, 68.1, 72.5, 73.5, 78.0, 79.4, 86.8, 104.3, 113.1, 127.7, 127.7, 127.7, 127.9, 127.9, 128.4, 128.4, 129.6, 134.0, 134.0, 135.7, 138.2, 138.3; MS (FAB): m/z 675 (M+Na$^+$), high-resolution MS (FAB) Calculated C$_{40}$H$_{48}$O$_6$SiNa (M+Na$^+$): 675.3118. Found: 675.3115.

(5) Synthesis of Compound 39

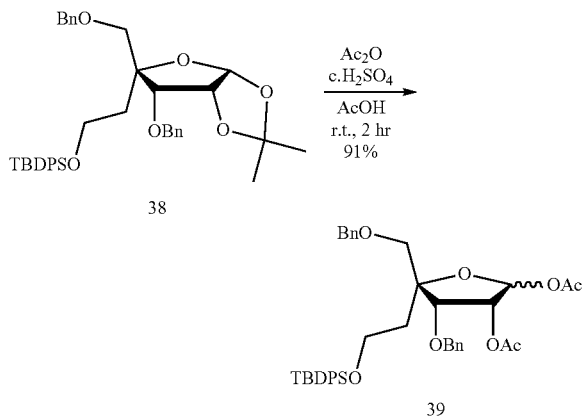

Under nitrogen stream, to a solution of compound 38 from (4) above (5.86 g, 8.98 mmol) in acetic acid (30 mL) was added dropwise acetic anhydride (10 mL, 108 mmol) and 0.1% (w/v) sulfuric acid (4.0 mL, acetic acid solution) and the mixture was stirred for 2 hours at room temperature. The reaction was quenched by adding saturated sodium bicarbonate solution to the reactant at 0° C., which was then extracted three times with ethyl acetate. The organic layer was washed once with saturated sodium bicarbonate solution, once with water and once with saturated saline, and then dried over sodium sulfate. After the solvent was distilled away under reduced pressure, the resultant crude product (6.18 g) was purified by silica-gel column chromatography (200 g, n-hexane:ethyl acetate=5:1 (v/v)) to give compound 39 (5.67 g:yield 91%) as a colorless oil.

The physical property data of the resultant compound 39 was as follows: $[α]_D^{24}$ -16.3 (c 1.00, CHCl$_3$); IR (KBr): 3069, 3031, 2931, 2857, 1748, 1428, 1369, 1219 cm$^{-1}$; $^1$H-NMR (400 MHz, CDCl$_3$): δ1.01 (s, 9H), 1.82 (s, 3H), 1.92 (s, 3H), 1.96-2.13 (m, 2H), 3.37, 3.49 (AB, J=10.0 Hz, 2H), 3.79-3.92 (m, 2H), 4.34-4.42 (m, 3H), 4.45, 4.56 (AB, J=12.0 Hz, 2H), 5.27 (d, J=5.5 Hz, 1H), 6.01 (s, 1H), 7.20-7.67 (m, 20H); $^{13}$C-NMR (100 MHz, CDCl$_3$): δ19.2, 20.7, 21.1, 26.9, 35.9, 59.9, 73.3, 73.6, 74.8, 78.2, 86.8, 97.8, 127.5, 127.6, 127.7, 127.8, 127.9, 128.4, 128.5, 129.6, 134.0, 134.0, 135.7, 138.0, 138.3, 169.5, 169.8; MS (FAB): m/z 719 (M+Na$^+$), high-resolution MS (FAB): Calculated C$_{41}$H$_{48}$O$_8$SiNa (M+Na$^+$): 719.3016. Found: 719.2999.

(6) Synthesis of Compound 40

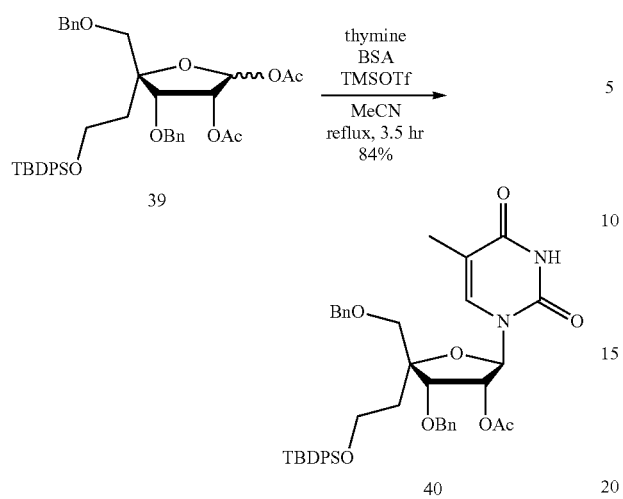

Under nitrogen stream, to a solution of compound 39 from (5) above (5.57 g, 8.00 mmol) in anhydrous acetonitrile (20 mL) was added thymine (1.41 g, 11.2 mmol) and then added dropwise N,O-bis trimethylsilyl acetamide (6.8 mL, 28.0 mmol), which was then heated at reflux for 1.5 hours. The reactant was cooled to room temperature, to which trimethylsilyl trifluoromethane sulfonate (1.9 mL, 10.4 mmol) was added dropwise at 0° C., and heated at reflux for 3.5 hours. The reaction was quenched by adding saturated sodium bicarbonate solution to the reactant at 0° C., which was then diluted with ethyl acetate and extracted three times. The organic layer was washed once with water and once with saturated saline, and then dried over sodium sulfate. After the solvent was distilled away under reduced pressure, the resultant crude product (5.71 g) was purified by silica-gel column chromatography (150 g, n-hexane:ethyl acetate=3:2(v/v)) to give compound 40 (5.14 g:yield 84%) as a white foam.

The physical property data of the resultant compound 40 was as follows: melting point 45-48° C.; $[\alpha]_D^{25}$ +10.2 (c 1.00, CHCl$_3$); IR (KBr): 3172, 3068, 2930, 2857, 1747, 1693, 1470, 1372, 1234 cm$^{-1}$; $^1$H-NMR (400 MHz, CDCl$_3$): δ1.01 (s, 9H), 1.48 (s, 3H), 1.76-1.83 (m, 1H), 2.04 (s, 3H), 2.03-2.11 (m, 1H), 3.41, 3.89 (AB, J=10.5 Hz, 2H), 3.71-3.83 (m, 2H), 4.35 (d, J=6.5 Hz, 1H), 4.39, 4.44 (AB, J=9.5 Hz, 2H), 4.38, 4.57 (AB, J=11.5 Hz, 2H), 5.35 (dd, J=5.0, 6.5 Hz, 1H), 6.08 (d, J=5.0 Hz, 1H), 7.20-7.41 (m, 16H), 7.49 (s, 1H), 7.60-7.65 (m, 4H), 7.83 (s, 1H); $^{13}$C-NMR (100 MHz, CDCl$_3$): δ12.1, 19.2, 20.9, 27.0, 35.2, 59.4, 73.2, 73.5, 74.4, 75.4, 77.6, 86.2, 87.5, 111.3, 127.7, 127.8, 128.0, 128.1, 128.6, 128.7, 129.8, 133.6, 133.6, 135.6, 135.8, 137.5, 137.6, 150.4, 163.7, 170.2.

(7) Synthesis of Compound 41

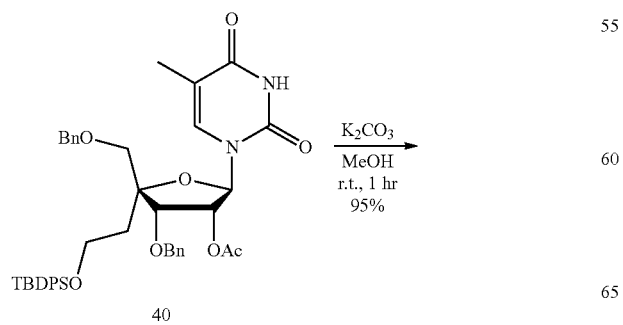

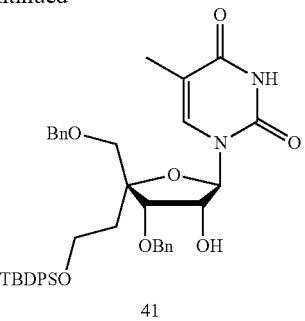

To a solution of compound 40 from (6) above (5.04 g, 6.61 mmol) in methanol (10 mL) was added potassium carbonate (450 mg, 3.30 mmol) and the mixture was stirred at room temperature for 1 hour. After the solvent was distilled away under reduced pressure, water was added to the residue, which was then extracted three times with ethyl acetate. The organic layer was washed once with saturated saline and then dried over sodium sulfate. After the solvent was distilled away under reduced pressure, the resultant crude product (4.76 g) was purified by silica-gel column chromatography (100 g, n-hexane:ethyl acetate=4:3 (v/v)) to give compound 41 (4.54 g:yield 95%) as a white foam.

The physical property data of the resultant compound 41 was as follows: melting point 62-64° C.; $[\alpha]_D^{26}$ −10.3 (c 1.00, CHCl$_3$); IR (KBr): 3423, 3179, 3066, 2928, 2856, 1695, 1471, 1428, 1270 cm$^{-1}$; $^1$H-NMR (400 MHz, CDCl$_3$): δ1.06 (s, 9H), 1.56 (s, 3H), 1.77 (ddd, J=6.5, 8.0, 14.5 Hz, 1H), 2.14 (dt, J=5.0, 14.5 Hz, 1H), 2.83 (d, J=8.0 Hz, 1H), 3.45, 3.85 (AB, J=10.5 Hz, 2H), 3.73-3.88 (AB, m, 2H), 3.85 (d, J=10.5 Hz, 1H), 4.14 (d, J=6.0 Hz, 1H), 4.30 (m, 1H), 4.46, 4.49 (AB, J=12.0 Hz, 2H), 4.56, 4.63 (AB, J=11.0 Hz, 2H), 5.82 (d, J=6.0 Hz, 1H), 7.22-7.65 (m, 21H), 8.12 (s, 1H); $^{13}$C-NMR (100 MHz, CDCl$_3$): δ12.2, 19.2, 27.0, 35.5, 59.5, 73.6, 74.2, 74.7, 75.2, 79.5, 87.2, 88.6, 111.1, 127.6, 127.8, 127.8, 128.1, 128.2, 128.4, 128.7, 128.7, 129.8, 133.6, 135.6, 136.0, 137.2, 137.5, 150.9, 163.8.

(8) Synthesis of Compound 42

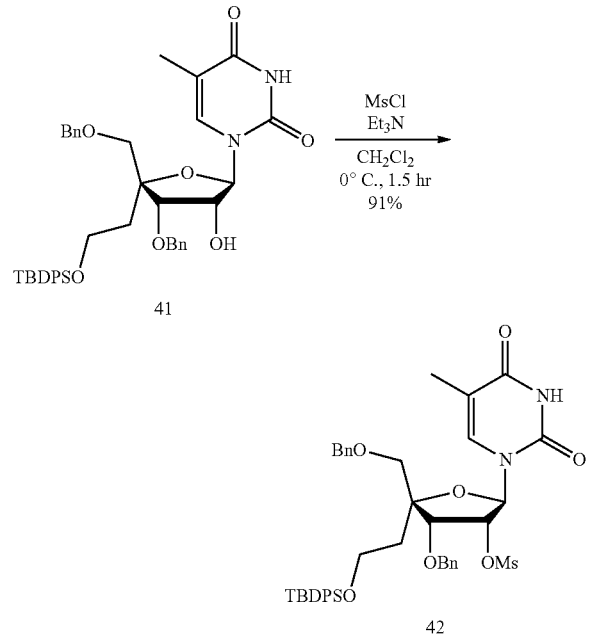

Under nitrogen stream, to a solution of compound 41 from (7) above (3.26 g, 4.52 mmol) in anhydrous dichloromethane (40 mL) was added triethylamine (6.3 mL, 45.2 mmol) and methanesulfonyl chloride (0.70 mL, 9.04 mmol) and the mixture was stirred at 0° C. for 1.5 hours. The reaction was quenched by adding saturated sodium bicarbonate solution to the reactant at 0° C., which was then extracted three times with dichloromethane. The organic layer was washed once with water followed by once with saturated saline and then dried over sodium sulfate. After the solvent was distilled away under reduced pressure, the resultant crude product (3.80 g) was purified by silica-gel column chromatography (100 g, n-hexane:ethyl acetate=4:3 (v/v)) to give compound 42 (3.29 g:yield 91%) as a white foam.

The physical property data of the resultant compound 42 was as follows: melting point 57-62° C.; $[\alpha]_D^{22}$ +214.8 (c 1.00, CHCl$_3$); IR (KBr): 3168, 3068, 3031, 2932, 2857, 1694, 1471, 1361, 1178 cm$^{-1}$; $^1$H-NMR (400 MHz, CDCl$_3$): δ1.02 (s, 9H), 1.44 (s, 3H), 1.85 (ddd, J=6.5, 8.0, 14.5 Hz, 1H), 2.10 (dt, J=5.0, 14.5 Hz, 1H), 3.07 (s, 3H), 3.44, 3.95 (AB, J=6.5 Hz, 2H), 3.70-3.86 (m, 2H), 4.33 (d, J=5.0 Hz, 2H), 4.37, 4.42 (AB, J=12.0 Hz, 2H), 4.45, 4.83 (AB, J=12.0 Hz, 2H), 5.26 (dd, J=3.0, 5.0 Hz, 1H), 6.01 (d, J=3.0 Hz, 1H), 7.18-7.63 (m, 21H), 8.29 (s, 1H); $^{13}$C-NMR (75.5 MHz, CDCl$_3$): δ11.9, 19.1, 26.8, 35.1, 38.8, 59.1, 72.6, 73.4, 73.8, 75.7, 80.3, 86.7, 87.8, 111.2, 127.6, 127.6, 127.7, 128.1, 128.3, 128.4, 128.6, 129.7, 129.7, 133.3, 133.4, 135.3, 135.5, 137.1, 137.2, 150.5, 163.5.

(9) Synthesis of Compound 43

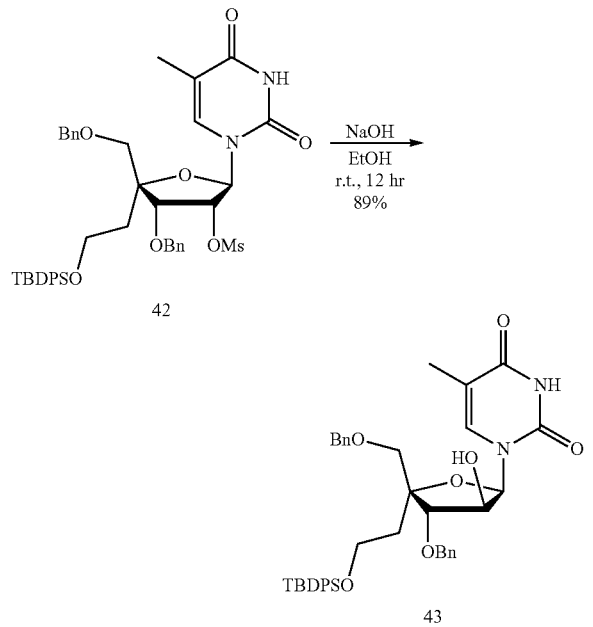

To a solution of compound 42 from (8) above (3.16 g, 3.95 mmol) in ethanol (40 mL) was added dropwise aqueous sodium hydroxide (1 M, 12 mL, 12.0 mmol) and the mixture was stirred at room temperature for 12 hours. The reaction was quenched by adding aqueous ammonium chloride solution to the reactant which was then extracted three times with ethyl acetate. The extract was washed once with water followed by once with saturated saline and then dried over sodium sulfate. After the solvent was distilled away under reduced pressure, the resultant crude product (2.72 g) was purified by silica-gel column chromatography (100 g, n-hexane:ethyl acetate=1:1 (v/v)) to give compound 43 (2.55 g:yield 89%) as a white foam.

The physical property data of the resultant compound 43 was as follows: melting point 56-58° C.; $[\alpha]_D^{26}$ +43.5 (c 1.00, CHCl$_3$); IR (KBr): 3357, 3181, 3068, 3031, 2929, 2856, 1695, 1472, 1428, 1281 cm$^{-1}$; $^1$H-NMR (400 MHz, CDCl$_3$): δ1.02 (s, 9H), 1.71 (d, J=1.5 Hz, 3H), 1.83-1.98 (m, 2H), 3.55, 3.94 (AB, J=10.5 Hz, 2H), 3.70-3.86 (m, 2H), 3.96 (d, J=9.0 Hz, 1H), 4.06 (d, J=3.0 Hz, 1H), 4.28 (ddd, J=3.0, 4.0, 9.0 Hz, 1H), 4.45, 4.70 (AB, J=12.0 Hz, 2H), 4.49, 4.53 (AB, J=11.5 Hz, 2H), 5.93 (d, J=4.0 Hz, 1H), 7.22-7.63 (m, 20H), 7.48 (d, J=1.5 Hz, 1H), 8.02 (s, 1H); $^{13}$C-NMR (100 MHz, CDCl$_3$): δ12.4, 19.2, 27.0, 35.3, 59.7, 72.8, 73.1, 73.8, 74.8, 83.9, 84.8, 85.2, 109.4, 127.8, 128.0, 128.1, 128.5, 128.8, 129.9, 133.6, 135.6, 136.8, 137.5, 137.7, 150.8, 164.1.

(10) Synthesis of Compound 44

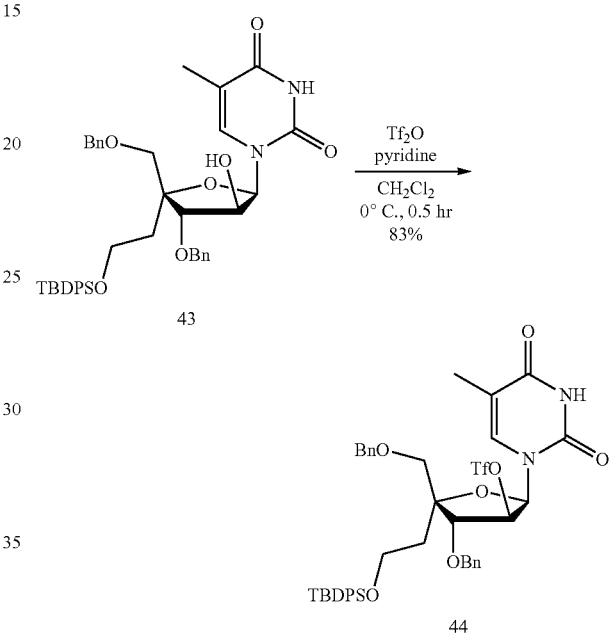

Under nitrogen stream, to a solution of compound 43 from (9) above (2.07 g, 2.87 mmol) in anhydrous dichloromethane (30 mL) was added anhydrous pyridine (1.9 mL, 17.2 mmol) and then added dropwise trifluoromethanesulfonic anhydride (1.4 mL, 8.60 mmol) at 0° C. and the mixture was stirred for 0.5 hours. The reaction was quenched by adding saturated sodium bicarbonate solution to the reactant at 0° C., which was then extracted three times with dichloromethane. The organic layer was washed once with water followed by once with saturated saline and then dried over sodium sulfate. After the solvent was distilled away under reduced pressure, the resultant crude product (2.56 g) was purified by silica-gel column chromatography (100 g, n-hexane:ethyl acetate=2:1) to give compound 44 (2.03 g:yield 83%) as a white foam.

The physical property data of the resultant compound 44 was as follows: melting point 37-40° C.; $[\alpha]_D^{25}$ +37.1 (c 1.00, CHCl$_3$); IR (KBr): 3190, 3069, 2930, 2858, 1695, 1455, 1426, 1245, 1215, 1143 cm$^{-1}$; $^1$H-NMR (400 MHz, CDCl$_3$): δ1.02 (s, 9H), 1.68 (s, 3H), 1.81-1.94 (m, 2H), 3.36, 3.69 (AB, J=10.5 Hz, 2H), 3.72-3.86 (m, 2H), 4.38, 4.43 (AB, J=12.0 Hz, 2H), 4.48, 4.72 (AB, J=11.5 Hz, 2H), 4.57 (d, J=4.5 Hz, 1H), 5.35 (t, J=4.5 Hz, 1H), 6.20 (d, J=4.5 Hz, 1H), 7.19-7.63 (m, 21H), 8.81 (s, 1H); $^{13}$C-NMR (100 MHz, CDCl$_3$): δ12.4, 19.2, 26.9, 34.2, 59.2, 71.4, 73.5, 73.7, 80.7, 81.7, 84.6, 87.7, 111.1, 127.8, 128.1, 128.2, 128.5, 128.7, 129.9, 133.5, 135.6, 136.7, 137.3, 150.1, 163.4; MS (FAB): m/z 853 (M+H$^+$), high-resolution MS (FAB): Calculated C$_{43}$H$_{48}$N$_2$O$_9$F$_3$SiS (M+H$^+$): 853.2802. Found: 853.2813.

(11) Synthesis of Compound 45

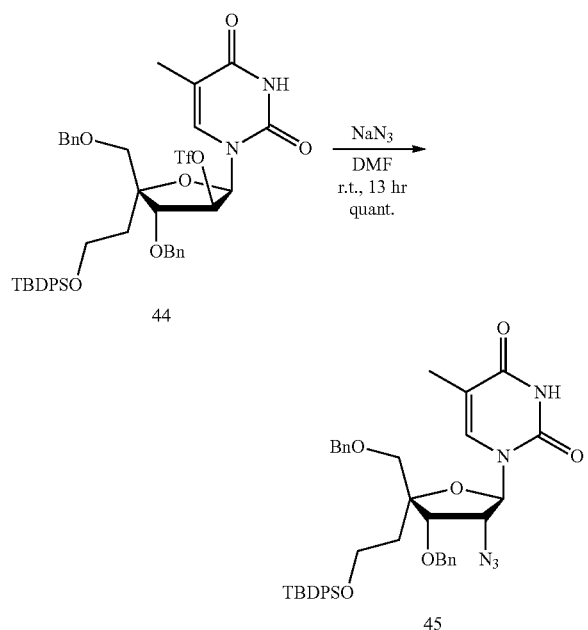

Under nitrogen stream, to a solution of compound 44 from (10) above (2.03 g, 2.38 mmol) in anhydrous N,N-dimethylformamide (20 mL) was added sodium azide (464 mg, 7.14 mmol) and the mixture was stirred for 13 hours at room temperature. Water was added to the reactant which was then extracted three times with diethyl ether, and the extract was washed once with saturated saline and dried over sodium sulfate. After the solvent was distilled away under reduced pressure, the resultant crude product (2.20 g) was purified by silica-gel column chromatography (150 g, n-hexane:ethyl acetate=2:1 (v/v)) to give compound 45 (1.80 g: quantitative) as a white foam.

The physical property data of the resultant compound 45 was as follows: melting point 46-49° C.; $[\alpha]_D^{25}$ −5.1 (c 1.00, CHCl$_3$); IR (KBr): 3179, 3068, 2929, 2857, 2109, 1694, 1470, 1428, 1268 cm$^{-1}$; $^1$H-NMR (400 MHz, CDCl$_3$): δ1.02 (s, 9H), 1.56 (s, 3H), 1.77 (ddd, J=6.5, 8.0, 14.5 Hz, 1H), 2.15 (dt, J=5.0, 14.5 Hz, 1H), 3.44, 3.91 (AB, J=11.0 Hz, 2H), 3.70-3.85 (m, 2H), 3.97 (t, J=6.0 Hz, 1H), 4.28 (d, J=6.0 Hz, 1H), 4.42, 4.48 (AB, J=11.5 Hz, 2H), 4.48, 4.78 (AB, J=11.5 Hz, 2H), 5.99 (d, J=6.0 Hz, 1H), 7.20-7.63 (m, 20H), 7.49 (s, 1H), 8.66 (s, 1H); $^{13}$C-NMR (100 MHz, CDCl$_3$): δ12.2, 19.2, 27.0, 35.4, 59.4, 65.3, 73.6, 73.6, 74.4, 79.2, 86.1, 87.7, 111.2, 127.7, 127.8, 128.2, 128.3, 128.4, 128.6, 128.8, 129.8, 128.9, 133.6, 135.4, 135.7, 137.0, 137.3, 150.3, 163.6; MS (FAB): m/z 746 (M+H$^+$), high-resolution MS (FAB): Calculated C$_{42}$H$_{48}$N$_5$O$_6$Si (M+H$^+$): 746.3374. Found: 746.3404.

(12) Synthesis of Compound 46

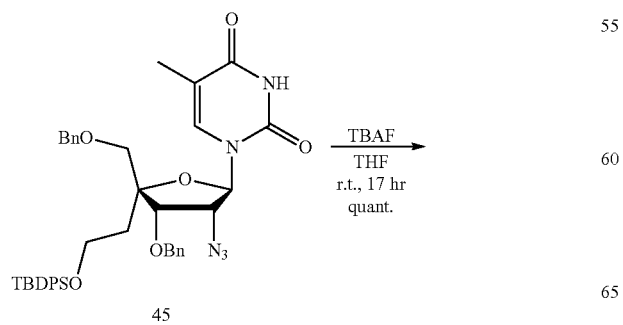

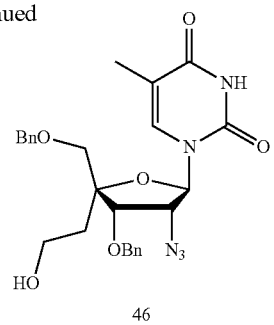

Under nitrogen stream, to a solution of compound 45 from (11) above (1.78 g, 2.39 mmol) in anhydrous tetrahydrofuran (20 mL) was added dropwise tetra-n-butylammonium fluoride (1M tetrahydrofuran solution, 2.6 mL, 2.60 mmol) and the mixture was stirred for 17 hours at room temperature. Water was added to the reactant which was then extracted three times with diethyl ether, and the organic layer was then washed once with saturated saline and dried over sodium sulfate. After the solvent was distilled away under reduced pressure, the resultant crude product (2.20 g) was purified by silica-gel column chromatography (75 g, n-hexane: ethyl acetate=1:1 (v/v)) to give compound 46 (1.22 g: quantitative) as a white foam.

The physical property data of the resultant compound 46 was as follows: melting point 45-50° C.; $[\alpha]_D^{25}$ +10.2 (c 1.00, CHCl$_3$); IR (KBr): 3441, 3181, 3063, 2927, 2108, 1693, 1469, 1455, 1267 cm$^{-1}$; $^1$H-NMR (400 MHz, CDCl$_3$): δ1.56 (s, 3H), 1.66 (br, 1H), 1.76 (dt, J=6.0, 15.0 Hz, 1H), 2.21 (dt, J=6.0, 15.0 Hz, 1H), 3.44, 3.82 (AB, J=10.5 Hz, 2H), 3.75 (t, J=6.0 Hz, 2H), 4.04 (t, J=6.0 Hz, 1H), 4.30 (d, J=6.0 Hz, 1H), 4.47, 4.53 (AB, J=11.5 Hz, 2H), 4.55, 4.83 (AB, J=12.0 Hz, 2H), 6.10 (d, J=6.0 Hz, 1H), 7.22-7.38 (m, 10H), 7.44 (s, 1H), 8.34 (s, 1H); $^{13}$C-NMR (100 MHz, CDCl$_3$): δ12.2, 34.9, 58.3, 65.0, 73.4, 73.8, 74.6, 79.6, 86.4, 87.9, 111.5, 127.8, 128.2, 128.4, 128.5, 128.7, 128.8, 135.4, 136.9, 137.1, 150.5, 163.8; MS (FAB): m/z 508 (M+H$^+$), high-resolution MS (FAB): Calculated C$_{26}$H$_{30}$N$_5$O$_6$ (M+H$^+$): 508.2196. Found: 508.2204.

(13) Synthesis of Compound 47

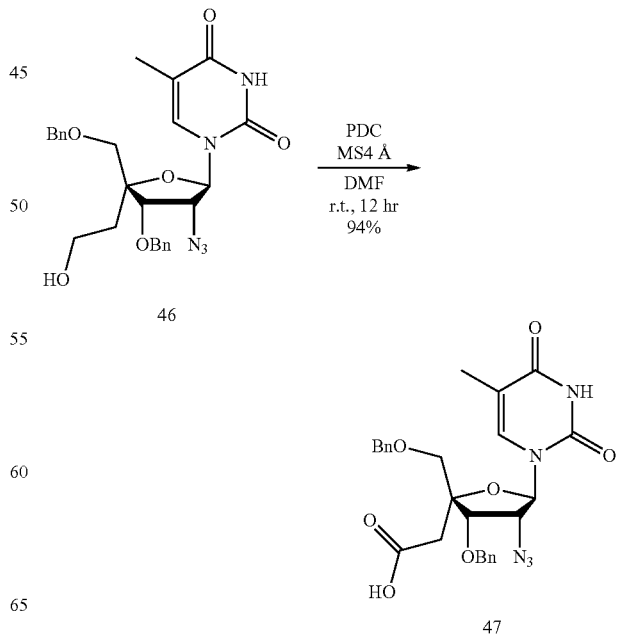

Under nitrogen stream, to a solution of compound 46 from (12) above (1.22 g, 2.40 mmol) in N,N-dimethylformamide (20 mL) was added molecular sieves 4 Å powder (3.0 g) and pyridinium dichromate (10.9 g, 28.8 mmol) and the mixture was stirred for 12 hours at room temperature. Acetic acid (5.0 mL) and water was added to the reactant which was then diluted with ethyl acetate and filtered through Celite. The filtrate was extracted three times with ethyl acetate and the organic layer was washed once with aqueous oxalic acid solution (0.4 M, 200 mL) followed by once with aqueous ammonium oxalate solution (0.2 M, 200 mL) and once with saturated saline, and then dried over sodium sulfate. After the solvent was distilled away under reduced pressure, the resultant crude product (3.20 g) was purified by silica-gel column chromatography (75 g, n-hexane:ethyl acetate:acetic acid=50:50:1 (v/v/v)) to give compound 47 (1.18 g:yield 94%) as a white foam.

The physical property data of the resultant compound 47 was as follows: melting point 78-81° C.; $[\alpha]_D^{25}$ −29.4 (c 1.00, CHCl$_3$); IR (KBr): 3510, 3179, 3033, 2929, 2108, 1705, 1470, 1455, 1269, 1213 cm$^{-1}$; $^1$H-NMR (400 MHz, CDCl$_3$): δ1.56 (s, 3H), 2.71, 2.88 (AB, J=16.5 Hz, 2H), 3.77, 3.94 (AB, J=10.0 Hz, 2H), 3.99 (dd, J=5.5, 7.0 Hz, 2H), 4.37 (d, J=5.5 Hz, 1H), 4.53, 4.61 (AB, J=10.5 Hz, 2H), 4.49, 4.88 (AB, J=11.0 Hz, 2H), 6.22 (d, J=7.0 Hz, 1H), 7.20-7.48 (m, 11H), 9.65 (s, 1H); $^{13}$C-NMR (100 MHz, CDCl$_3$): δ12.1, 38.0, 65.0, 73.8, 74.0, 75.3, 80.3, 85.3, 86.4, 111.7, 127.8, 128.1, 128.2, 128.5, 128.5, 128.9, 135.6, 136.8, 137.0, 150.1, 164.4, 175.1; MS (FAB): m/z 522 (M+H$^+$), high-resolution MS (FAB): Calculated C$_{26}$H$_{28}$N$_5$O$_7$ (M+H$^+$): 522.1989. Found: 522.1979.

(14) Synthesis of Compound 48

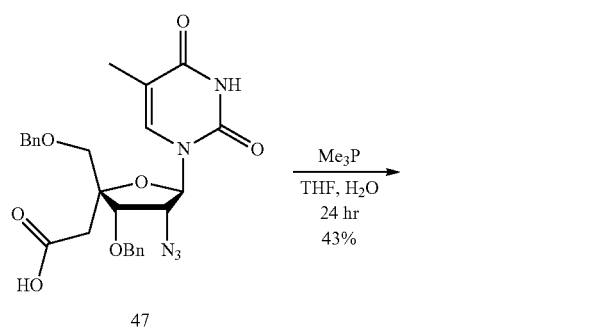

47

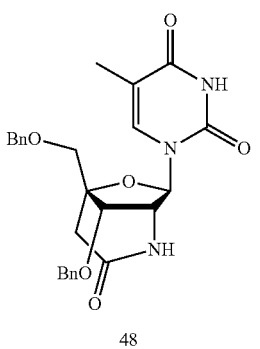

48

To a solution of compound 47 from (13) above (241 mg, 0.462 mmol) in tetrahydrofuran/water (5:1 (v/v)) (241 mg, 0.462 mmol, 6 mL) was added dropwise trimethylphosphine (1M toluene solution, 0.55 mL, 0.550 mmol) and the mixture was stirred for 24 hours at room temperature. After the solvent was distilled away under reduced pressure, the resultant crude product (293 mg) was purified by silica-gel column chromatography (10 g, chloroform:methanol=30:1 (v/v)) to give compound 48 (106 mg:yield 43%) as a white powder.

The physical property data of the resultant compound 48 was as follows: melting point 112-114° C.; $[\alpha]_D^{21}$ +78.9 (c 1.00, CHCl$_3$); IR (KBr): 3500, 3169, 3063, 2927, 1684, 1454, 1367, 1273, 1211 cm$^{-1}$; $^1$H-NMR (400 MHz, CDCl$_3$): δ1.36 (d, J=1.0 Hz, 3H), 2.40, 2.57 (AB, J=18.0 Hz, 2H), 3.58, 3.72 (AB, J=11.0 Hz, 2H), 4.05 (dd, J=3.5, 5.5 Hz, 2H), 4.24 (d, J=3.5 Hz, 1H), 4.54, 4.58 (AB, J=11.5 Hz, 2H), 4.51, 4.65 (AB, J=11.5 Hz, 2H), 5.76 (s, 1H), 6.86 (br, 1H), 7.24-7.35 (m, 10H), 7.92 (d, J=1.0 Hz, 1H), 9.40 (br, 1H); $^{13}$C-NMR (100 MHz, CDCl$_3$): δ11.9, 38.6, 55.7, 68.7, 70.6, 71.9, 73.6, 83.8, 90.1, 109.6, 127.5, 127.9, 128.0, 128.2, 128.4, 128.7, 135.5, 137.0, 137.1, 150.7, 164.2, 169.6; MS (FAB): m/z 478 (M+H$^+$), high-resolution MS (FAB): Calculated C$_{26}$H$_{28}$N$_3$O$_6$ (M+H$^+$): 478.1978. Found: 478.1983.

(15) Synthesis of Compound 49

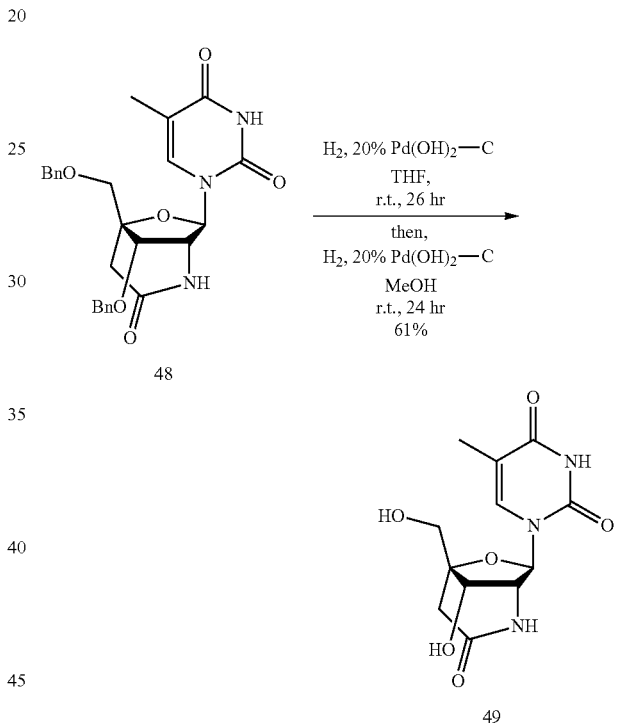

Under nitrogen stream, to a solution of compound 48 from (14) above (50 mg, 0.105 mmol) in tetrahydrofuran (2 mL) was added 20% (v/v) palladium hydroxide on carbon (50 mg) and the mixture was stirred for 26 hours at room temperature under hydrogen stream. After filtration through a pleated filter paper, the filtrate was washed with methanol, from which the solvent was then distilled away. To the residue was added methanol (2 mL) and 20% (v/v) palladium hydroxide on carbon (50 mg) and the mixture was further stirred for 24 hours under hydrogen stream. After filtration through a pleated filter paper, the filtrate was washed with methanol from which the solvent was then distilled away. The residue was recrystallized with methanol to give compound 49 (19.1 mg:yield 61%) as a white solid.

The physical property data of the resultant compound 49 was as follows: $[\alpha]_D^{23}$ +36.5 (c 0.200, CH$_3$OH); IR (KBr): 3449, 3318, 3175, 3060, 2926, 2819, 1707, 1651, 1469, 1386, 1272, 1215 cm$^{-1}$; $^1$H-NMR (300 MHz, CD$_3$OD): δ1.86 (d, J=1.0 Hz, 3H), 2.29, 2.46 (AB, J=18.0 Hz, 2H), 3.69, 3.75

(AB, J=12.5 Hz, 2H), 3.83 (d, J=4.0 Hz, 1H), 4.34 (d, J=4.0 Hz, 1H), 5.69 (s, 1H), 8.36 (d, J=1.0 Hz, 1H); $^{13}$C-NMR (100.53 MHz, CD$_3$OD): δ12.5, 38.8, 60.0, 61.8, 64.4, 86.0, 91.0, 110.1, 137.8, 152.1, 166.6, 173.3; MS (FAB): m/z 298 (M+H$^+$), high-resolution MS (FAB): Calculated C$_{26}$H$_{28}$N$_3$O$_6$ (M+H$^+$): 298.1039. Found: 298.1044.

(16) Synthesis of Compound 50

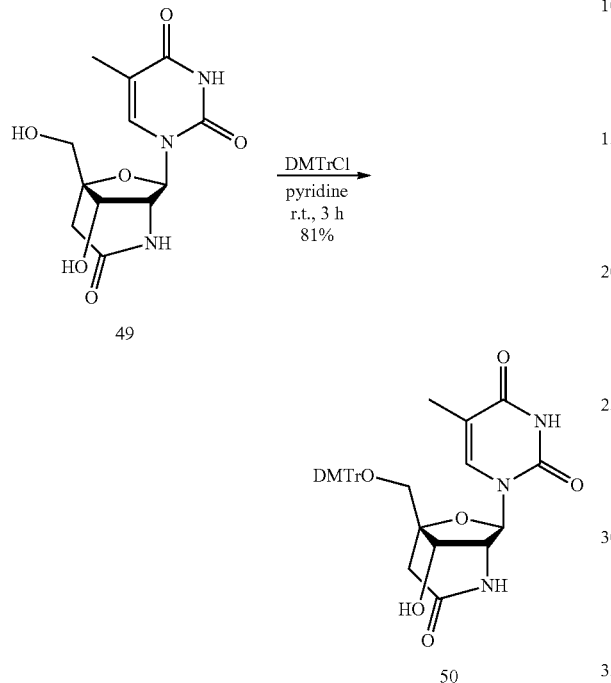

Under nitrogen stream, to a solution of compound 49 from (15) above (28 mg, 0.094 mmol) in anhydrous pyridine (2 mL) was added 4,4'-dimethoxytrityl chloride (95.7 mg, 0.283 mmol) at 0° C. and the mixture was stirred for 3 hours at room temperature. The reaction was quenched by adding saturated sodium bicarbonate solution to the reactant at 0° C., which was then extracted three times with dichloromethane. The organic layer was washed once with saturated saline and then dried over sodium sulfate. After the solvent was distilled away under reduced pressure, the resultant crude product (159 mg) was purified by silica-gel column chromatography (5.0 g, chloroform:methanol=20:1) to give compound 50 (45.9 mg:yield 81%) as a white foamy solid.

The physical property data of the resultant compound 50 was as follows: [α]$_D^{23}$ +80.7 (c 1.00, CHCl$_3$); IR (KBr): 3562, 3341, 3062, 2933, 2838, 1704, 1657, 1608, 1509, 1465, 1253 cm$^{-1}$; $^1$H-NMR (400 MHz, CD$_3$OD): δ1.21 (d, J=1.0 Hz, 3H), 2.42 (s, 2H), 3.36 (s, 2H), 3.77 (s, 6H), 3.93 (d, J=4.0 Hz, 1H), 4.56 (d, J=4.0 Hz, 1H), 5.67 (s, 1H), 6.86-7.48 (m, 13H), 7.90 (d, J=1.0 Hz, 1H); $^{13}$C-NMR (100 MHz, CD$_3$OD) δ: 12.26, 39.34, 55.72, 59.80, 64.27, 65.71, 79.46, 85.55, 88.07, 91.72, 110.64, 114.27, 128.20, 129.02, 129.46, 131.46, 136.40, 136.61, 136.90, 145.76, 152.01, 160.36, 166.56, 173.01; MS (FAB): m/z 600 (M+H$^+$), high-resolution MS (FAB): Calculated C$_{26}$H$_{28}$N$_3$O$_6$ (M+H$^+$): 600.2346. Found: 600.2347.

(17) Synthesis of Compound 51

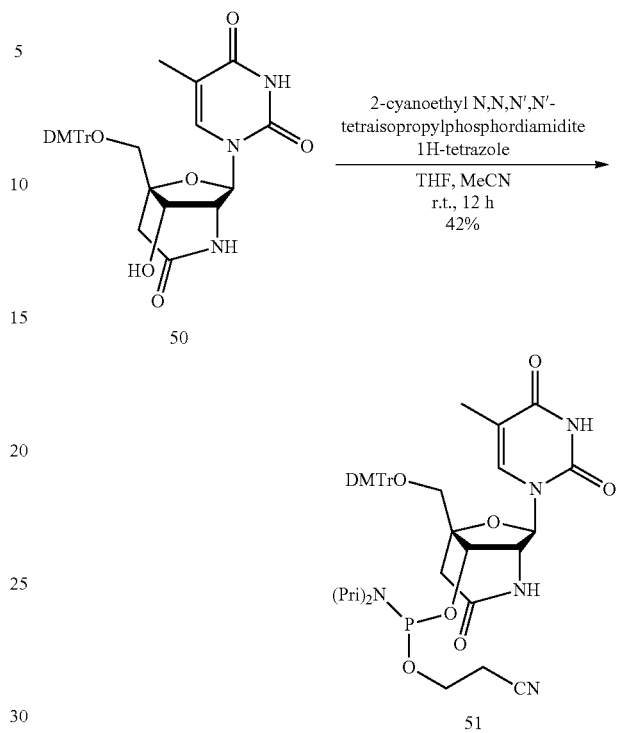

Under nitrogen stream, to a solution of compound 50 from (16) above (72 mg, 0.120 mmol) in anhydrous tetrahydrofuran/acetonitrile (3:1 (v/v)) (2.0 mL) was added 1 H-tetrazole (10.1 mg, 0.144 mmol) and 2-cyanoethyl-N,N,N',N'-tetraisopropyl phosphoramidite (46 μL, 0.14 mmol) and the mixture was stirred for 12 hours at room temperature. The reaction was quenched by adding saturated sodium bicarbonate solution to the reactant at 0° C., which was then extracted three times with dichloromethane. The organic layer was washed once with saturated sodium bicarbonate solution followed by once with saturated saline, and then dried over sodium sulfate. After the solvent was distilled away under reduced pressure, the resultant crude product (99 mg) was purified by silica-gel column chromatography (3.0 g, chloroform:methanol=20:1) to give the crude product (70.2 mg, 73%). The resultant crude product was dissolved in dichloromethane, which was then added to n-hexane for reprecipitation to give compound 51 (40.1 mg, 42%) as a white solid.

The physical property data of the resultant compound 51 was as follows: $^{31}$P-NMR (161.83 MHz, CHCl$_3$): δ149.13, 150.91; MS (FAB): ink 800 (M+H$^+$), high-resolution MS (FAB): Calculated C$_{26}$H$_{28}$N$_3$O$_6$ (M+H$^+$): 800.3424. Found: 800.3406.

Example 6

Synthesis and Purification of the Oligonucleotide Analogues

10mer of the oligonucleotide analogues containing compound 51 from Example 5 above (compounds 52-55: showed in Table 3 below) were synthesized using Expedite™ 8909 (from ABI) in the scale of 0.2 μmol. In this synthesis, the capping step in the standard phosphoramidite protocol was skipped. The compound 51 (amidite unit) was dissolved in tetrahydrofuran to use in the synthesis. In Table 3, the compound 51 is indicated by X. Duration of the coupling reaction between an amidite unit (compound 51) and a hydroxyl group at 5'-terminus was extended from 1.5 minutes (standard condition) to 30 minutes. The oligonucleotide analogues with the 5'-terminus protected with a DMTr group supported on a solid phase were treated with 0.05 M solution of potassium carbonate in methanol and then neutralized with 5% (w/v) hydrochloric acid, after which the solvent was distilled away. The resultant crude product was partially purified by the gel filtration column NAP™ 10 Column (GE Health Care) and then purified by reversed-phase HPLC(SHIMADZU LC-10AT$_{VP}$, SHIMADZU SPD-10A$_{VP}$, SHIMADZU CTO-10$_{VP}$, using WatersXBridge™ OST C$_{18}$ 2.5 µm (10 mm×50 mm) as a preparative column).

The purities of the synthesized oligonucleotide analogues (compounds 52-55) were determined using reversed-phase HPLC (WatersXBridge™ Shield RP18 2.5 µm, 4.6 mm×50 mm)) (condition: gradient 7→13% (v/v) acetonitrile in 0.1 M triethyl ammonium acetate buffer (pH 7.0), 1 mL/min for 30 minutes). The molecular weights were determined by MALDI-TOF-MASS. The results are shown in Table 3.

TABLE 3

| Oligonucleotide | | MALDI-TOF-MASS | |
|---|---|---|---|
| | | Calculated (M − H⁻) | Found (M − H⁻) |
| 5'-TTTTTXTTTT-3' | (Compound 52) | 3034.00 | 3033.71 |
| 5'-TTTXTXTTTT-3' | (Compound 53) | 3089.03 | 3088.89 |
| 5'-TTTXTXTXTT-3' | (Compound 54) | 3144.07 | 3145.94 |
| 5'-TTTTTTTTXT-3' | (Compound 55) | 3034.00 | 3035.17 |

Example 7

Determination of the Melting Temperature (Tm)

After compounds 52-54 (antisense strands), which were the oligonucleotide strands synthesized in Example 5 above, and sense strands (3'-AAAAAAAAAA-5') were subjected to an annealing treatment, their Tm values were measured to determine the hybridization ability of the antisense strands.

The sample solution (130 µL) containing 100 mM NaCl, 10 mM sodium phosphate buffer (pH 7.2), 4 µM antisense strands and 4 µM sense strands was heated in a boiled water bath and then cooled to room temperature over 10 hours. Nitrogen stream was passed into a cell chamber of a spectrophotometer (Shimadzu, UV-1650PC) for dew condensation prevention, and the sample solution was gradually cooled to 5° C. and kept at 10° C. for 20 minutes before starting the measurements. The temperature was raised to 85° C. at the rate of 0.5° C./min while ultraviolet absorption spectra were measured at 260 nm at intervals of 0.1° C. Lidded cells were used to prevent concentration change due to rising temperature. The results are shown in Table 4.

TABLE 4

| | | Sense strand | | | |
|---|---|---|---|---|---|
| | | RNA complementary strand | | DNA complementary strand | |
| Antisense strand | | Tm (° C.) | Δ Tm/mod. (° C.) | Tm (° C.) | Δ Tm/mod. (° C.) |
| 5'-TTTTTTTTTT-3' | (Compound 21) | 19 | | 20.9 | |
| 5'-TTTTTXTTTT-3' | (Compound 52) | 19.2 | +0.2 | 15.7 | −5.2 |
| 5'-TTTXTXTTTT-3' | (Compound 53) | 28.3 | +4.7 | 19.5 | −0.7 |
| 5'-TTTXTXTXTT-3' | (Compound 54) | 33.3 | +4.4 | 26.9 | +2.0 |

Δ Tm/mod. = Δ Tm/modified base

As shown in Table 4, the oligonucleotide analogues of the invention have higher affinities to single-stranded RNAs than to single-stranded DNAs. The more artificial nucleic acids introduced into an oligonucleotide, the higher Tm value it has. Therefore, the nucleotide analogues of the invention are believed to be useful for the synthesis of the oligonucleotides suitable for antisense therapies.

Example 8

Synthesis of the Nucleoside Analogue: N2'-methyl-2'-amino-3'-O-[2-cyanoethoxy(diisopropylamino)phosphino]-5'-O-dimethoxytrityl-2'-N,4'-C-oxoethyl-enethymidine (compound 60: amide 6NMe)

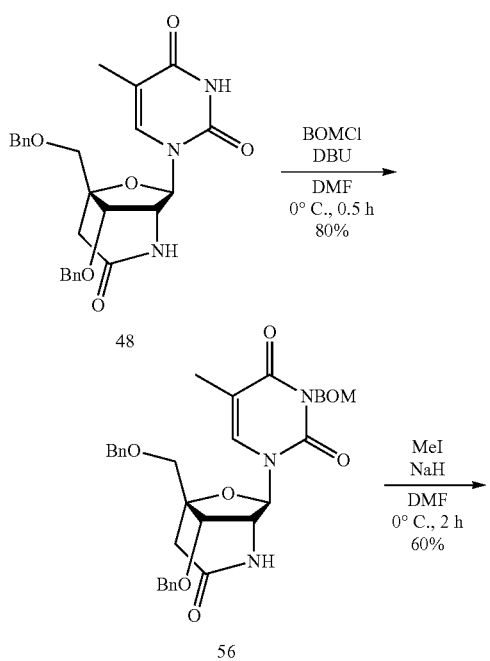

-continued

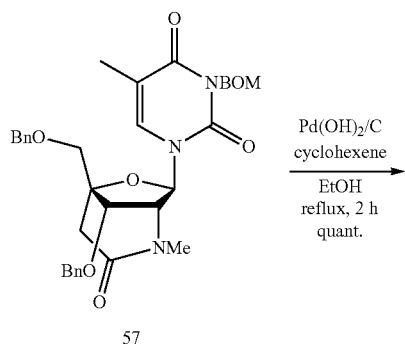
57

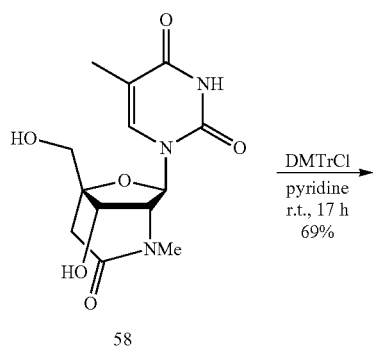
58

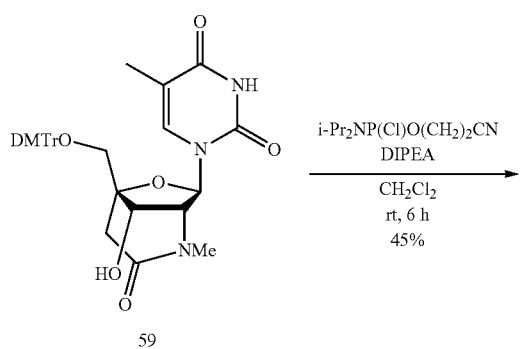
59

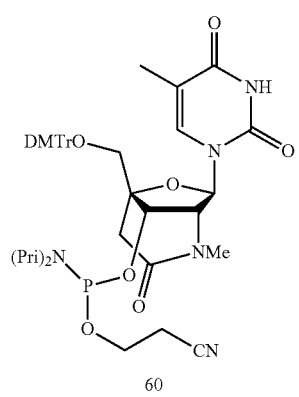
60

(1) Synthesis of Compound 56

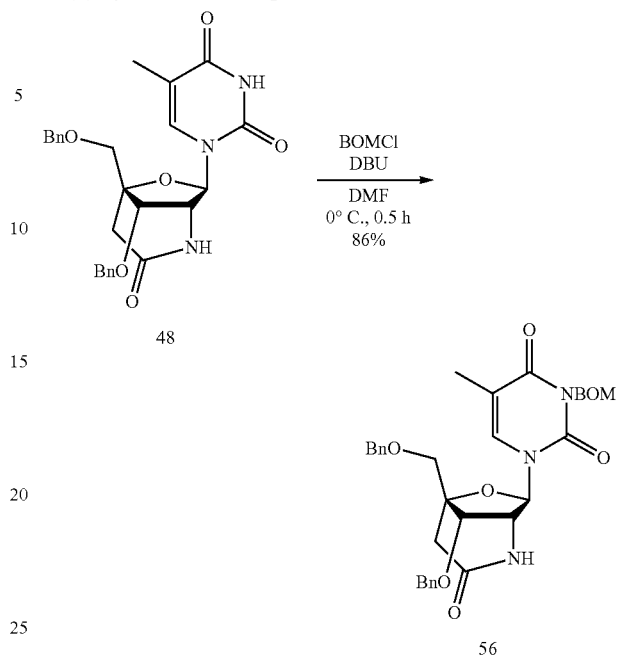

Under nitrogen stream, to a solution of compound 48 (94 mg, 0.197 mmol) in anhydrous N,N-dimethylformamide (2.0 mL) was added 1,8-diazabicyclo[5.4.0]undec-7-ene (0.12 mL, 0.79 mmol) and benzyl chloromethyl ether (55 µL, 0.39 mmol) at 0° C. and the mixture was stirred for 0.5 hours. The reaction was quenched by adding saturated sodium bicarbonate solution to the reactant at 0° C., which was then extracted three times with ethyl acetate. The organic layer was washed once with water and once with saturated saline and then dried over sodium sulfate. After the solvent was distilled away under reduced pressure, the resultant crude product (112 mg) was purified by silica-gel column chromatography (5.0 g, n-hexane:ethyl acetate=1:1) to give compound 56 (101 mg:yield 86%) as a white foamy solid.

The physical property data of the resultant compound 56 was as follows: $^1$H-NMR (400 MHz, CDCl$_3$): δ1.43 (d, J=1.0 Hz, 3H), 2.45, 2.60 (AB, J=17.5 Hz, 2H), 3.59, 3.76 (AB, J=10.5 Hz, 2H), 3.96 (dd, J=4.0, 5.5 Hz, 1H), 4.19 (d, J=4.0 Hz, 1H), 4.51, 4.63 (AB, J=11.0 Hz, 2H), 4.55, 4.60 (AB, J=11.0 Hz, 2H), 4.69 (s, 2H), 5.43, 5.46 (AB, J=9.5 Hz, 2H), 5.74 (s, 1H), 6.15 (d, J=5.5 Hz, 1H), 7.25-7.38 (m, 15H), 7.92 (d, J=1.0 Hz, 1H); $^{13}$C-NMR (100 MHz, CDCl$_3$): δ12.53, 38.68, 56.09, 70.27, 70.57, 72.27, 72.37, 73.69, 83.76, 90.53, 109.48, 127.55, 127.64, 127.71, 127.91, 128.30, 128.34, 128.58, 128.73, 133.97, 136.59, 136.88, 137.82, 150.79, 163.29, 169.26.

(2) Synthesis of Compound 57

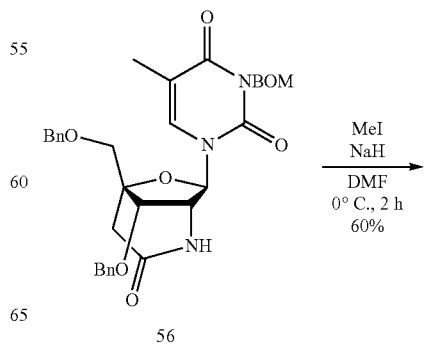
56

57

-continued

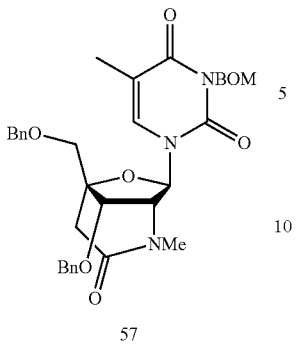

57

Under nitrogen stream, to a solution of compound 56 from (1) above (130 mg, 0.218 mmol) in anhydrous N,N-dimethylformamide (2.0 mL) was added sodium hydride (10.4 mg, 0.260 mmol) at 0° C. and the mixture was stirred for 0.5 hours, to which methyl iodide (68 μL, 1.1 mmol) was then added at 0° C. and the mixture was stirred for 2 hours. The reaction was quenched by adding water to the reactant at 0° C., which was then extracted three times with diethyl ether. The organic layer was washed once with saturated saline and then dried over sodium sulfate. After the solvent was distilled away under reduced pressure, the resultant crude product (139 mg) was purified by silica-gel column chromatography (5.0 g, n-hexane:ethyl acetate=3:2) to give compound 57 (79.6 mg, 60%) as a white foamy solid.

The physical property data of the resultant compound 57 was as follows: $^1$H-NMR (400 MHz, CDCl$_3$): δ1.45 (d, J=1.0 Hz, 3H), 2.42, 2.60 (AB, J=17.0 Hz, 2H), 3.07 (s, 3H), 3.68, 3.74 (AB, J=12.0 Hz, 2H), 3.82 (d, J=4.0 Hz, 1H), 4.16 (d, J=4.0 Hz, 1H), 4.55, 4.60 (AB, J=11.0 Hz, 2H), 4.70 (s, 2H), 5.43, 5.47 (AB, J=9.5 Hz, 2H), 4.56 (s, 2H), 5.66 (s, 1H), 7.23-7.39 (m, 15H), 7.91 (d, J=1.0 Hz, 1H); $^{13}$C-NMR (100 MHz, CDCl$_3$): δ12.55, 34.17, 38.77, 63.11, 68.51, 70.20, 71.19, 72.27, 72.72, 73.64, 84.24, 88.87, 109.38, 127.52, 127.66, 127.70, 127.89, 128.27, 128.30, 128.32, 128.62, 128.69, 133.93, 136.69, 136.92, 137.81, 150.68, 163.35, 167.29.

(3) Synthesis of Compound 58

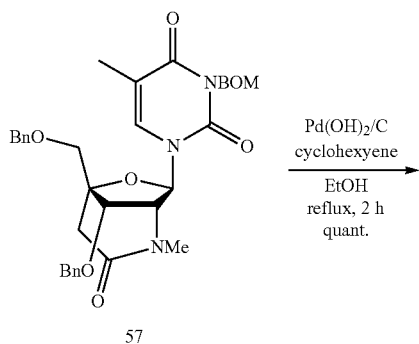

58

-continued

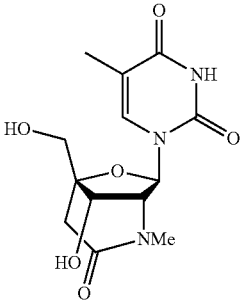

58

To the 20% suspension of palladium hydroxide on carbon (91.0 mg) in ethanol (2.0 mL) was added the solution of compound 57 from (2) above (79.6 mg, 0.130 mmol) in ethanol (8.0 mL) and cyclohexene (1.3 mL, 13 mmol) and the mixture was heated at reflux for 2 hours. After filtrating off palladium hydroxide on carbon through a pleated filter paper, the solvent was distilled away under reduced pressure and the resultant crude product was purified by silica-gel column chromatography (2.0 g, chloroform:methanol=10:1) to give compound 58 (40.8 mg: quant.) as a white powder.

The physical property data of the resultant compound 58 was as follows: $^1$H-NMR (400 MHz, CD$_3$OD): δ1.77 (d, J=1.0 Hz, 3H), 2.21, 2.39 (AB, J=18.0 Hz, 2H), 3.02 (s, 3H), 3.57, 3.64 (AB, J=12.5 Hz, 2H), 3.80 (d, J=4.0 Hz, 1H), 4.23 (d, J=4.0 Hz, 1H), 5.60 (s, 1H), 8.18 (d, J=1.0 Hz, 1H); $^{13}$C-NMR (100 MHz, CD$_3$OD): δ12.54, 34.92, 39.01, 61.62, 64.88, 67.70, 86.54, 89.34, 110.21, 137.46, 152.07, 166.63, 170.82.

(4) Synthesis of Compound 59

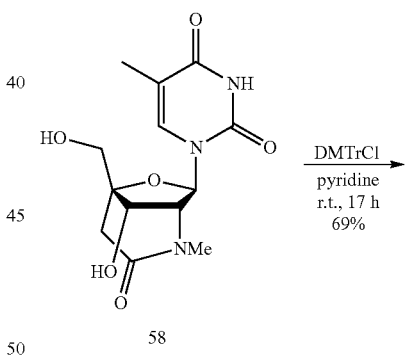

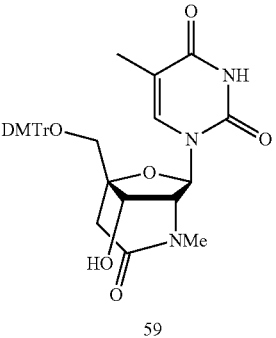

59

Under nitrogen stream, to a solution of compound 58 from (3) above (26.8 mg, 0.0861 mmol) in anhydrous pyridine (2.0 mL) was added 4,4'-dimethoxytrityl chloride (175 mg, 0.567 mmol) at 0° C. and the mixture was stirred for 17 hours at room temperature. The reaction was quenched by adding saturated sodium bicarbonate solution to the reactant at 0° C., which was then extracted three times with dichloromethane. The organic layer was washed once with saturated saline and then dried over sodium sulfate. After the solvent was distilled away under reduced pressure, the resultant crude product (320 mg) was purified by silica-gel column chromatography (5.0 g, chloroform:methanol=25:1) to give compound 59 (36.6 mg:yield 69%) as a white foamy solid.

The physical property data of the resultant compound 59 was as follows: $^1$H-NMR (400 MHz, CDCl$_3$): δ1.29 (s, 3H), 2.44, 2.53 (AB, J=17.5 Hz, 2H), 3.08 (s, 3H), 3.33, 3.37 (AB, J=12.0 Hz, 6H), 3.75 (s, 3H), 3.76 (s, 3H), 3.94 (d, J=3.5 Hz, 1H), 4.49 (d, J=3.5 Hz, 1H), 5.61 (s, 1H), 6.80-7.41 (m, 14H), 7.90 (s, 1H); $^{13}$C-NMR (100 MHz, CDCl$_3$): δ11.91, 34.51, 38.54, 55.20, 62.87, 65.43, 65.98, 84.96, 86.88, 88.60, 110.39, 111.34, 127.20, 128.07, 130.10, 134.92, 135.08, 144.05, 152.35, 158.69, 164.37, 168.32.

(5) Synthesis of Compound 60

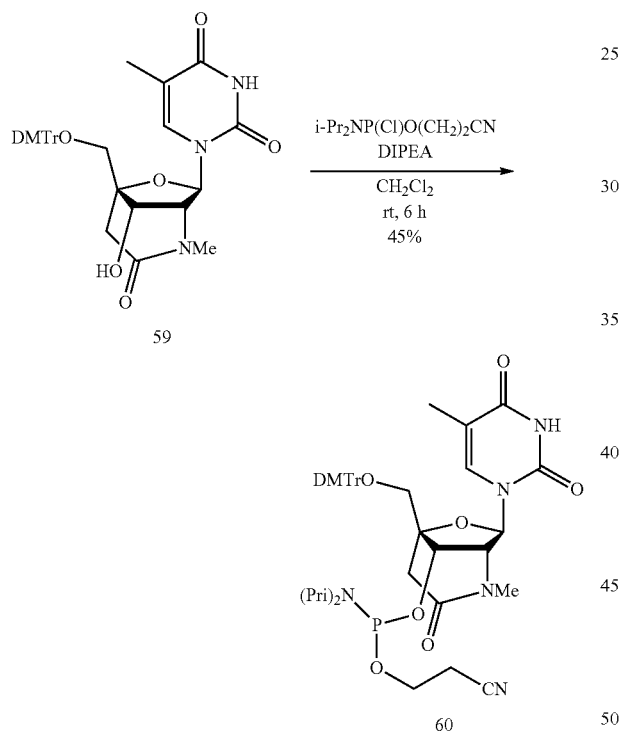

Compound 59 from (4) above (116 mg, 0.189 mmol) was azeotroped with pyridine and toluene and dissolved into anhydrous dichloromethane (1.9 mL) under nitrogen stream, to which N-ethyldiisopropylamine (0.20 mL, 1.13 mmol) was then added. Subsequently 2-cyanoethyl diisopropyl chlorophosphoramidite (85 μL, 0.378 mmol) was added to the mixture at 0° C., which was then stirred for 6 hours at room temperature. After saturated sodium bicarbonate solution was added to the mixture which was then stirred for a while and extracted with ethyl acetate, the organic layer was washed with water and saturated saline and then dried over sodium sulfate. After the solvent was distilled away, the resultant crude product was purified by column chromatography (chloroform:methanol:triethylamine=30:1:0.05) to give a white foamy solid. The resultant white foamy solid was dissolved in dichloromethane, which was then added to n-hexane for reprecipitation to give compound 60 (70 mg:yield 45%) as a white powder.

The physical property data of the resultant compound 60 was as follows: $^{131}$P-NMR (161.83 MHz, CDCl$_3$): δ148.84, 149.97.

Example 9

Synthesis of the Nucleoside Analogue: N2'-methyl-2'-amino-3'-O-[2-cyanoethoxy(diisopropylamino)phosphino]-5'-O-dimethoxytrityl-2'-N,4'-C-oxomethylene thymidine (Compound 65: Amide NMe)

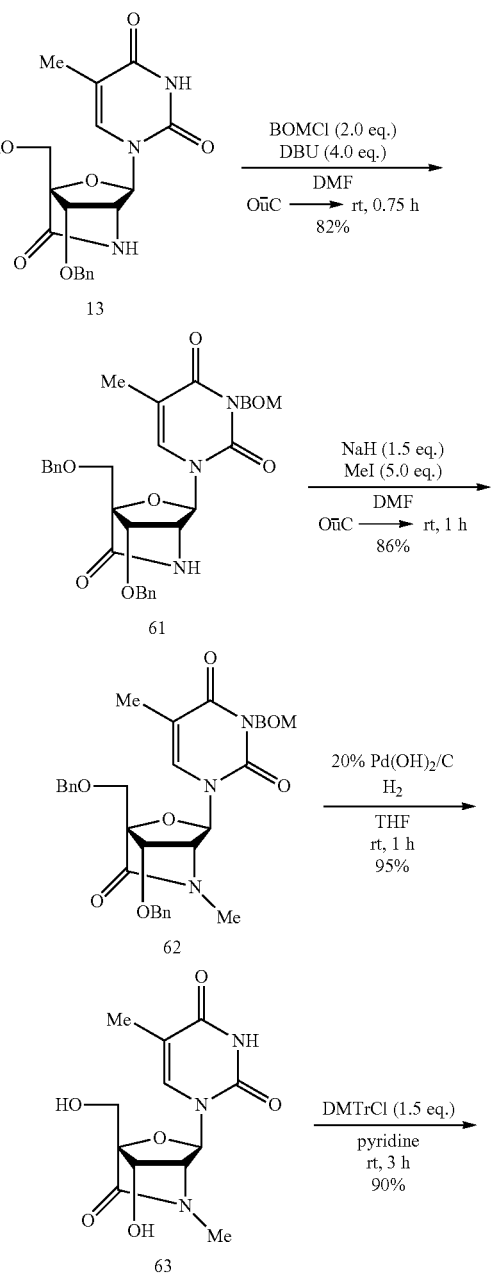

(1) Synthesis of Compound 61

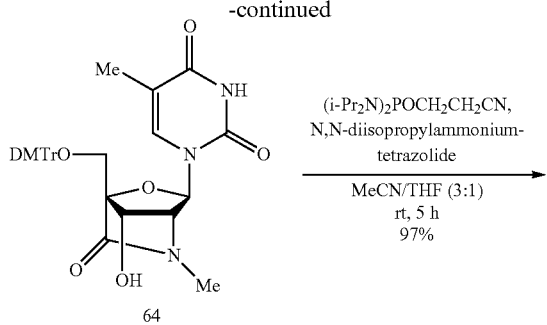

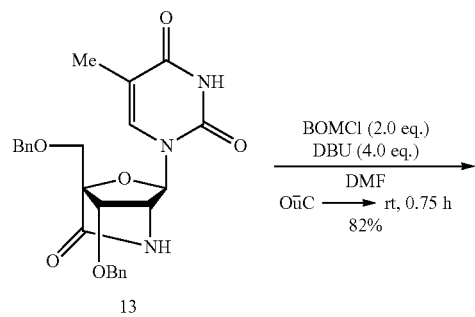

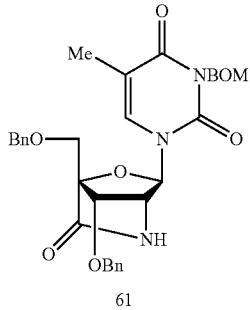

After compound 13 (30 mg, 0.065 mmol) was dissolved in N,N-dimethylformamide (0.7 mL) under nitrogen stream, to which 1,8-diazabicyclo[5.4.0]-7-undecene (38.6 μL, 0.259 mmol) was added on ice cooling, the mixture was stirred for 15 minutes, to which benzyl chloromethyl ether (17.7 μL, 0.129 mmol) was then added, and was stirred for 30 minutes on ice cooling. After adding methanol to the mixture which was then stirred, the solvent was distilled away and the residue was diluted with ethyl acetate. After addition of water and extraction with ethyl acetate, the organic layer was washed with saturated saline and then dried over sodium sulfate. After the solvent was distilled away, the resultant crude product was purified by column chromatography (n-hexane:ethyl acetate=3:1→1:1) to give compound 61 (31 mg:yield 82%) as a white foamy solid.

The physical property data of the resultant compound 61 was as follows: $[\alpha]_D$ +61.6 (c 0.700, CHCl$_3$, 26° C.). $^1$H-NMR (400 MHz, CDCl$_3$): δ1.62 (3H, s), 3.95, 4.10 (2H, AB, J=12 Hz), 4.11 (1H, s), 4.22 (1H, s), 4.52, 4.56 (2H, AB, J=13.5 Hz), 4.59, 4.64 (2H, AB, J=11 Hz), 4.72, 4.69 (2H, AB, J=13 Hz), 5.43 (1H, s), 5.43, 5.48 (2H, AB, J=9.5 Hz), 7.54-7.20 (15H, m), 7.54 (1H, s). $^{13}$C-NMR (100.53 MHz, CDCl$_3$): δ12.92, 58.47, 63.06, 70.26, 72.31, 72.42, 73.98, 78.72, 86.37, 86.58, 109.99, 127.68, 127.72, 127.75, 128.09, 128.29, 128.31, 128.52, 128.54, 133.93, 136.27, 137.40, 137.76, 150.63, 163.15, 172.57.

(2) Synthesis of Compound 62

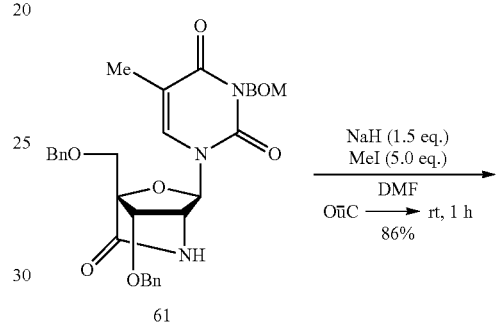

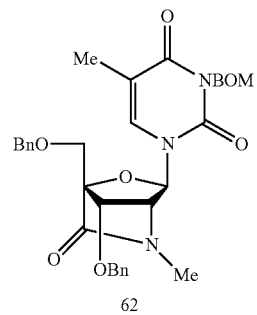

Under nitrogen stream, compound 61 from (1) above (30 mg, 0.051 mmol) was dissolved in N,N-dimethylformamide (0.5 mL), to which sodium hydride was then added on ice cooling, and the mixture was stirred for 30 minutes. Methyl iodide (15.9 μL, 0.255 mmol) was added to the mixture on ice cooling, which was then warmed gently to room temperature with stirring. After 30 minutes, water was added to the mixture which was then stirred for 10 minutes and extracted with ethyl acetate. The organic layer was washed with saturated saline and then dried over sodium sulfate. After the solvent was distilled away, the resultant crude product was purified by column chromatography (n-hexane:ethyl acetate=3:1→1:1) to give compound 62 (26.1 mg:yield 86%) as a white foamy solid.

The physical property data of the resultant compound 62 was as follows: $[\alpha]_D$ +39.0 (c 0.350, CHCl$_3$, 23° C.). $^1$H-NMR (400 MHz, CDCl$_3$): δ1.65 (3H, s), 2.96 (3H, s), 3.95, 4.10 (2H, AB, J=11.5 Hz), 4.01 (1H, s), 4.06 (1H, s), 4.50, 4.59 (2H, AB, J=12 Hz), 4.59, 4.63 (2H, AB, J=11 Hz), 4.70 (2H, s), 5.40 (1H, s), 5.44, 5.48 (2H, AB, J=9.5 Hz), 7.19-7.39 (15H, m), 7.52 (1H, s). $^{13}$C-NMR (100.53 MHz, CDCl$_3$): δ 12.92, 28.39, 63.23, 64.52, 70.24, 72.26, 72.54, 73.84, 78.06, 84.42, 87.09, 109.94, 127.58, 127.62, 127.65, 127.70, 127.99, 128.24, 128.27, 128.48, 128.50, 133.78, 136.39, 137.41, 137.72, 150.52, 163.09, 170.93.

(3) Synthesis of Compound 63

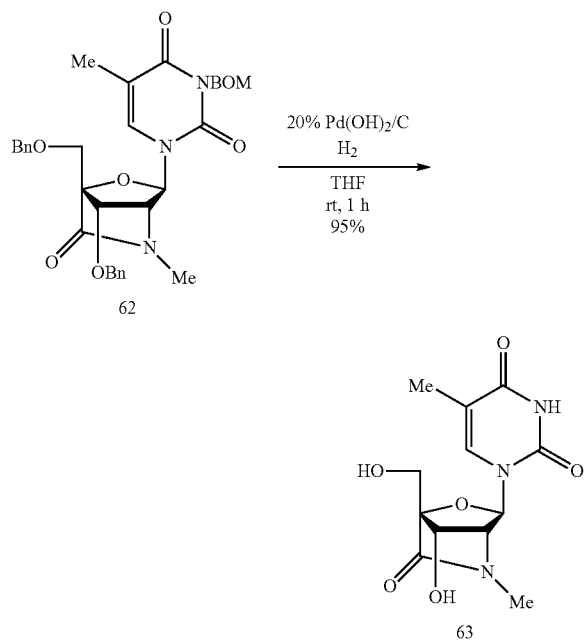

Under nitrogen stream, compound 62 from (2) above (130 mg, 0.218 mmol) was dissolved in tetrahydrofuran (2 mL), to which 20% palladium hydroxide on carbon (130 mg) was then added, and stirred for 1 hour at room temperature under hydrogen stream. After the reactant was naturally filtered and washed with warm methanol, the solvent was distilled away. The resultant crude product was purified by column chromatography (chloroform:methanol=10:1) to give compound 63 (61.7 mg:yield 95%) as a white solid.

The physical property data of the resultant compound 63 was as follows: $[\alpha]_D$+63.7 (c 0.900, CHCl$_3$, 26° C.). $^1$H-NMR (400 MHz, DMSO-D6): δ1.77 (3H, s), 2.88 (3H, s), 3.67, 3.84 (2H, AB, J=12.5 Hz), 4.03 (1H, s), 4.12 (1H, s), 5.28 (1H, s), 5.38 (1H, s), 5.90 (1H, s), 7.73 (1H, s), 11.44 (1H, s). $^{13}$C-NMR (100.53 MHz, CD$_3$OD): δ12.64, 28.65, 55.75, 68.53, 72.85, 85.48, 89.99, 110.93, 137.24, 151.96, 166.45, 174.14.

(4) Synthesis of Compound 64

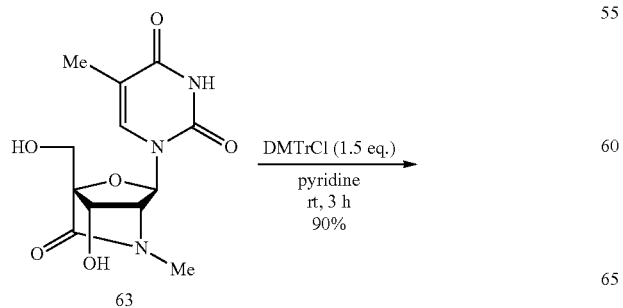

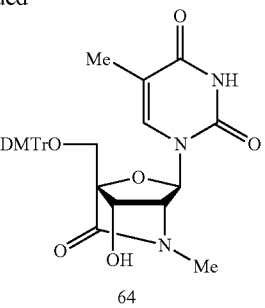

Under nitrogen stream, compound 63 from (3) above (61.7 mg, 0.208 mmol) azeotroped with pyridine was dissolved in anhydrous pyridine (2 mL), to which 4,4'-dimethoxytrityl chloride (106 mg, 0.311 mmol) was added, and then stirred for 3 hours at room temperature. After saturated sodium bicarbonate solution was added to the mixture which was then stirred for a while and extracted with ethyl acetate, the organic layer was washed with water and saturated saline and then dried over sodium sulfate. After the solvent was distilled away, the resultant crude product was purified by column chromatography (chloroform:methanol:triethylamine=20:1:0.05) to give compound 64 (113 mg:yield 90%) as a white foamy solid.

The physical property data of the resultant compound 63 was as follows: $[\alpha]_D$+2.0 (c 0.300, CHCl$_3$, 25° C.). $^1$H-NMR (400 MHz, CDCl$_3$): δ1.66 (3H, s), 2.97 (3H, s), 3.62, 3.90 (2H, AB, J=12.5 Hz), 3.77 (6H, s), 4.13 (1H, s), 4.42 (1H, s), 5.40 (1H, s), 6.82-6.85 (4H, m), 7.21-7.34 (7H, m), 7.43 (2H, d, J=8 Hz), 7.77 (1H, s), 9.45 (1H, s).

(5) Synthesis of Compound 65

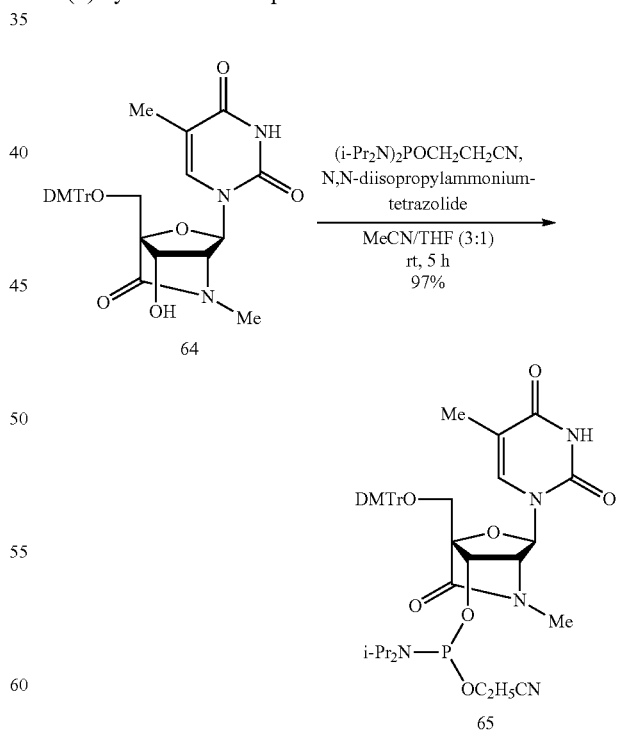

Under nitrogen stream, compound 64 from (4) above (1.18 g, 1.97 mmol) azeotroped with pyridine and toluene was dissolved in anhydrous acetonitrile/tetrahydrofuran (3:1) (23 mL), to which N,N-diisopropyl ammonium tetrazolide (253 mg, 1.48 mmol) and 2-cyanoethyl N,N,N',N'-tetraisopropyl phosphoramidite (752 µL, 2.37 mmol) was added, and stirred for 5 hours at room temperature. After saturated sodium bicarbonate solution was added to the mixture which was then stirred for a while and extracted with ethyl acetate, the organic layer was washed with water and saturated saline and then dried over sodium sulfate. After the solvent was distilled away, the resultant crude product was purified by column chromatography (chloroform:methanol:triethylamine=30:1: 0.05) to give a white foamy solid. The resultant white foamy solid was dissolved in dichloromethane, which was then added to n-hexane for reprecipitation to give compound 65 (1.53 g:yield 97%) as a white powder.

The physical property data of the resultant compound 65 was as follows: $^{31}$P-NMR (161.83 MHz, CDCl$_3$): δ150.43, 150.59.

Example 10

Synthesis and Purification of the Oligonucleotide Analogues

10mer of the oligonucleotide analogues containing compound 65 from Example 9 above (compounds 66-69: showed in Table 5 below) were synthesized using Expedite™ 8909 (from ABI) in the scale of 0.2 µmol. The compound 65 (amidite unit) was dissolved in acetonitrile to use in the synthesis. In Table 5, the compound 65 is indicated by X. Duration of the coupling reaction between an amidite unit (compound 65) and a hydroxyl group at 5'-terminus was extended from 1.5 minutes (standard condition) to 5 minutes. The oligonucleotide analogue with the 5'-terminus protected with a DMTr group supported on a solid phase was treated with saturated aqueous ammonia and then neutralized with 5% (w/v) hydrochloric acid, after which the solvent was distilled away. The resultant crude product was partially purified by the gel filtration column NAP™ 10 Column (GE Health Care) and then purified by reversed-phase HPLC(SHIMADZU LC-10AT$_{VP}$, SHIMADZU SPD-10A$_{VP}$, SHIMADZU CTO-10$_{VP}$, using WatersXBridge™ OST C$_{18}$ 2.5 µm (10 mm×50 mm) as a preparative column).

The purities of the synthesized oligonucleotide analogues (compounds 66-69) were determined using reversed-phase HPLC (WatersXBridge™ Shield RP18 2.5 µm, 4.6 mm×50 mm)) (condition: gradient 7→13% (v/v) acetonitrile in 0.1 M triethyl ammonium acetate buffer (pH 7.0), 1 mL/min for 30 minutes). The molecular weights were determined by MALDI-TOF-MASS. The results are shown in Table 5.

TABLE 5

| Oligonucleotide | | MALDI-TOF-MASS | |
|---|---|---|---|
| | | Calculated (M − H⁻) | Found (M − H⁻) |
| 5'-TTTTTXTTTT-3' | (Compound 66) | 3034.00 | 3034.33 |
| 5'-TTTXTXTTTT-3' | (Compound 67) | 3089.03 | 3089.46 |
| 5'-TTTXTXTXTT-3' | (Compound 68) | 3144.07 | 3144.55 |
| 5'-TTTTTTTTXT-3' | (Compound 69) | 3034.00 | 3034.29 |

Example 11

Determination of the Melting Temperature (Tm)

After compounds 66-68 (antisense strands), which were the oligonucleotide strands synthesized in Example 10 above, and sense strands (3'-AAAAAAAAAA-5') were subjected to an annealing treatment, their Tm values were measured to determine the hybridization ability of the antisense strands.

The sample solution (130 µL) containing 100 mM NaCl, 10 mM sodium phosphate buffer (pH 7.2), 4 µM antisense strands and 4 µM sense strands was heated in a boiled water bath and then cooled to room temperature over 10 hours. Nitrogen stream was passed into a cell chamber of a spectrophotometer (Shimadzu, UV-1650PC) for dew condensation prevention, and the sample solution was gradually cooled to 5° C. and kept at 10° C. for 20 minutes before starting the measurements. The temperature was raised to 85° C. at the rate of 0.5° C./min while ultraviolet absorption spectra were measured at 260 nm at intervals of 0.1° C. Lidded cells were used to prevent concentration change due to rising temperature. The results are shown in Table 6.

TABLE 6

| | | Sense strand | | | |
|---|---|---|---|---|---|
| | | RNA complementary strand | | DNA complementary strand | |
| Antisense strand | | Tm (° C.) | Δ Tm/mod. (° C.) | Tm (° C.) | Δ Tm/mod. (° C.) |
| 5'-TTTTTTTTTT-3' | (Compound 21) | 18.5 | | 21.2 | |
| 5'-TTTTTXTTTT-3' | (Compound 66) | 24.0 | +5.5 | 21.0 | −0.2 |
| 5'-TTTXTXTTTT-3' | (Compound 67) | 33.7 | +7.6 | 21.6 | +0.2 |
| 5'-TTTXTXTXTT-3' | (Compound 68) | 39.7 | +7.1 | 25.7 | +1.5 |

Δ Tm/mod. = Δ Tm/modified base

As shown in Table 6, the oligonucleotide analogues of the invention have higher affinities to single-stranded RNAs than to single-stranded DNAs and their affinities were comparable to known 2',4'-BNA/LNA and the more artificial nucleic acids introduced into an oligonucleotide, the higher Tm value it has. Therefore, the nucleotide analogues of the invention are believed to be as useful for synthesis of the oligonucleotides suitable for antisense therapies as 2',4'-BNA/LNA.

Example 12

Assessment of the Nuclease Resistance

Each oligonucleotide of compound 20 (amide NH) synthesized in Example 2 above, compound 55 (amide 6NH) synthesized in Example 6 and compound 69 (amide NMe) synthesized in Example 10 was subjected to the test for determining the resistance to an exonuclease which degrades an oligonucleotide in the direction from 3' to 5' direction. The conventional 2',4'-BNA/LNA and NC(NH) (2',4'-BNANC (NH): the structure with a bridging structure containing a nitrogen atom but not an amide) were used as a control.

A buffer solution containing 750 µmol of oligonucleotides (65 µL) was kept at 37° C. for 5 minutes and then mixed with a buffer solution (35 µL) containing 0.175 mg/mL of snake venom phosphodiesterase (Crotalus admanteus venom phosphodiesterase (CAVP): Pharmacia Biotech). Degradation of oligonucleotides was determined with HPLC(SHIMADZU LC-20AD, SPD-20A, CTO-20A, SIL-20AC, using WatersX-Bridge™ Shield RP18 2.5 µm (4.6 mm×50 mm) as an analytical column) over time. The employed buffer contains 50 mM Tris HCl (pH 8.0), 10 mM $MgCl_2$ (final concentration) and was sufficiently degassed before measurement. The condition of quantification with HPLC is as follows.

[HPLC Quantification Condition]

Mobile phase: Solution A 0.1 M triethyl ammonium acetate buffer, pH 7.0

Solution B 0.1M triethyl ammonium acetate buffer: acetonitrile=1:1(v/v), pH 7.0

Gradient: 5→11.4% (v/v) solution B (16 minutes)

Employed column: WatersXBridge™ Shield RP18 2.5 µm (4.6 mm×50 mm)

Flow rate: 0.8 mL/minute

Column temperature: 50° C.

Detection: UV (268 nm)

The result was shown in FIG. 1. In FIG. 1, "Remaining oligonucleotides (%)" refers to a remaining ratio of the undegraded oligonucleotides (10mer) at the time of measurement to the undegraded oligonucleotides (10mer) at the time 0.

As shown in FIG. 1, compound 20 (amide NH), compound 55 (amide 6NH) and compound 69 (amide NMe) were found to have a much higher enzyme-resistance than an oligonucleotide containing the conventional 2',4'-BNA/LNA.

Example 13

Assessment of Serum Stability of the Oligonucleotides (FBS)

1 nmol of oligonucleotides (5'-(XTXTXTXTXT)-3', where compound 65 from Example 9 was introduced at the position "X" in the sequence according to the method of Example 10) was mixed with 10 µL of 25% FBS, to which sterile water was added to make the whole volume to 25 µL. After the incubation of the solution for a given time at 37° C., 5 µL of the sample was removed at regular time intervals, which was heated to 90° C. and then cooled to inactivate the nucleolytic enzyme in FBS. These samples were stored at −80° C. until the analysis with HPLC. For the HPLC analysis, sterile water was added to the sample to adjust the whole volume to 200 µL before determining the oligonucleotide degradation over time with HPLC(SHIMADZU LC-20AD, SPD-20A, CTO-20A, SIL-20AC). The employed buffer contains 50 mM Tris HCl (pH 8.0), 10 mM $MgCl_2$ (final concentration) and was sufficiently degassed before measurement. The oligonucleotides where X is the sequence of naturally occurred DNA-T or LNA-T were subjected to the same test as described above for the comparison.

[HPLC Quantification Condition]

Mobile phase: Solution A 0.1M triethyl ammonium acetate buffer, pH7.0

Solution B 0.1M triethyl ammonium acetate buffer:acetonitrile=1:1, pH7.0

Gradient: 10→26% (v/v) Solution B (16 minutes)

Employed Column: WatersXBridge™ Shield RP18 2.5 µm (4.6 mm×50 mm)

Flow rate: 0.8 mL/minute

Column temperature: 50° C.

Detection: UV (268 nm)

The result was shown in Table 7. In Table 7, "Remaining oligonucleotides (%)" refers to a remaining ratio of the undegraded oligonucleotides (10mer) at the time of measurement to the undegraded oligonucleotides (10mer) at the time 0.

TABLE 7

| | Remaining oligonucleotides (%) | | |
|---|---|---|---|
| Time (minutes) | X = DNA-T | X = LNA-T | X = compound 65 |
| 30 | 40 | 3 | 88 |
| 60 | 15 | 2 | 63 |

As shown in Table 7, the oligonucleotide to which compound 65 of the invention has been introduced has a much better serum stability than oligonucleotides consisting of natural DNAs and oligonucleotides modified with LNA and thus may be expected to have beneficial effects in vivo.

Example 14

Synthesis of the Nucleoside Analogue: N2'-methyl-2'-amino-3'-O-[2-cyanoethoxy(diisopropylamino) phosphino]-5'-O-dimethoxytrityl-2'-N,4'-C-oxomethylene-4-(1,2,4,-triazole-1-yl) thymidine (Compound 70: Triazolyl of Thymidine Analogue, 5-methylcytocine Analogue Equivalent)

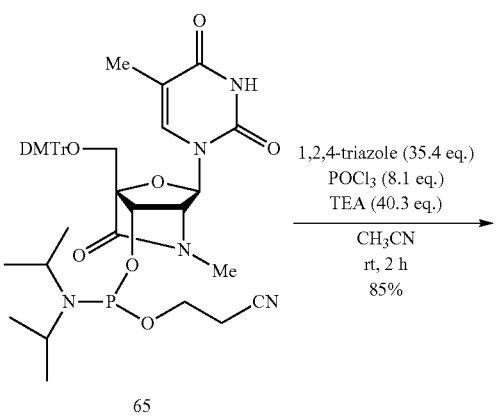

65

69
-continued

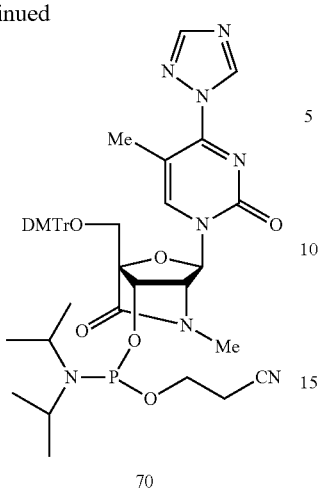
70

Under nitrogen stream, 1,2,4-triazole (306 mg, 4.43 mmol) azeotroped with pyridine and toluene was dissolved in anhydrous acetonitrile (10 mL), to which phosphoryl chloride (94 μL, 1.01 mmol) was then added on ice cooling, and then stirred vigorously for 10 minutes. Next, triethylamine (700 μL, 5.04 mmol) was added to the mixture which was then stirred vigorously for 1 hour. Compound 65 (100 mg, 0.125 mmol) was dissolved in anhydrous acetonitrile (2 mL) on ice cooling, which was then added to the reactant and stirred vigorously for 2 hours at room temperature. After adding saturated sodium bicarbonate solution and stirring, the mixture was extracted with ethyl acetate and the organic layer was washed with water and saturated saline and then dried over sodium sulfate. After the solvent was distilled away, the resultant crude product was purified by column chromatography (n-hexane:ethyl acetate=1:1) to give compound 70 (90.4 mg:yield 85%) as a white foamy solid.

The physical property data of the resultant compound 70 was as follows: $^{31}$P-NMR (161.83 MHz, CDCl$_3$): δ150.9, 149.6.

Example 15
Synthesis of the Nucleoside Analogue: N-methyl-3'-O-[2-cyanoethoxy(diisopropylamino) phosphino]-5'-O-dimethoxytrityl-2'-O,4'-C-aminooxomethylene-5-methyluridine (Compound 81: Amide NC-NMe)

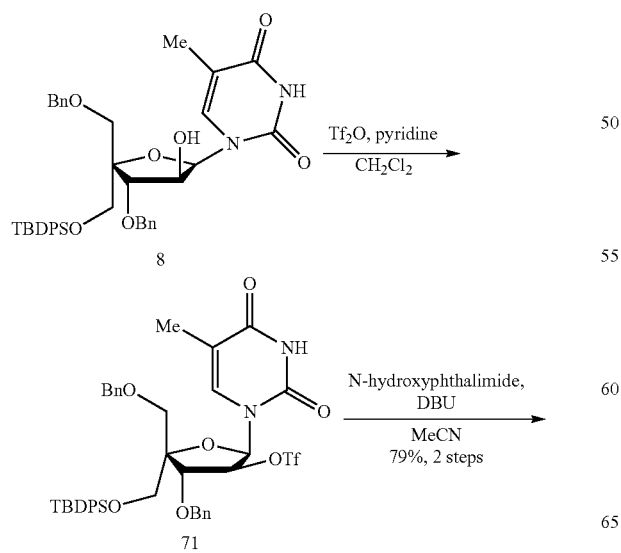

70
-continued

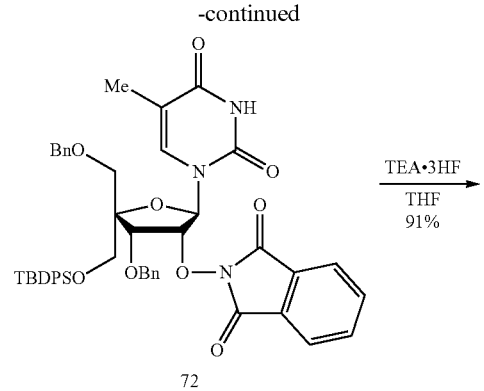

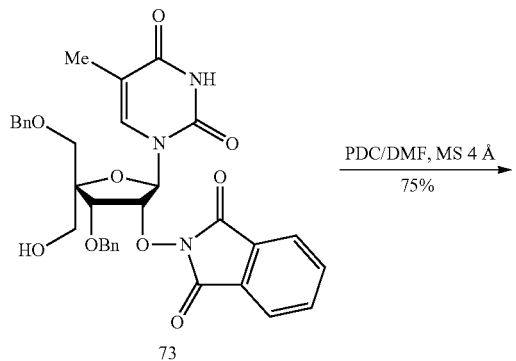

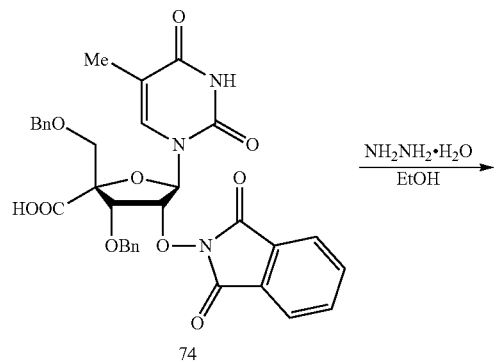

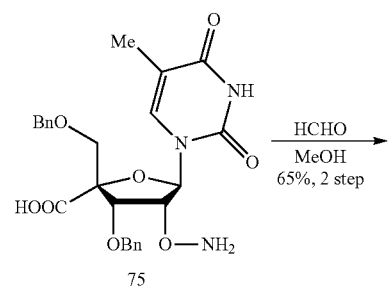

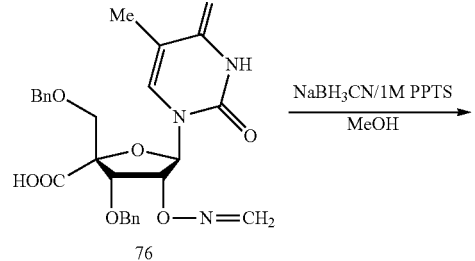

71

-continued

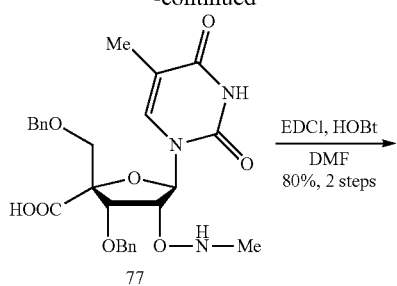
77

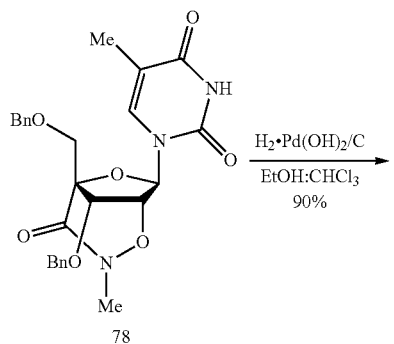
78

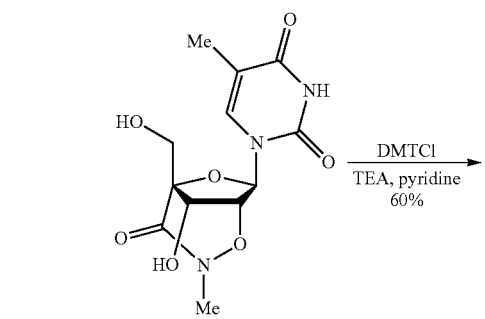
79

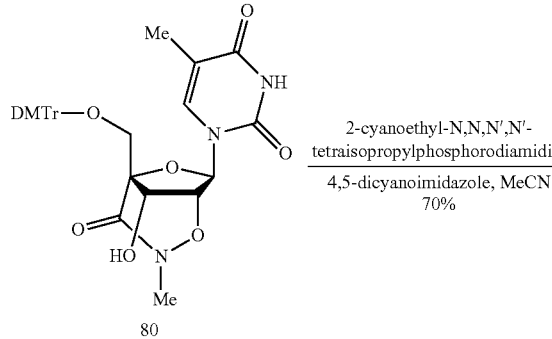
80

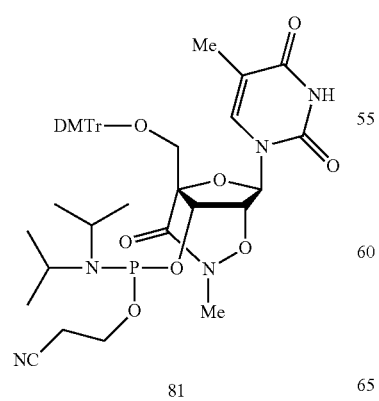
81

72

(1) Synthesis of Compound 71

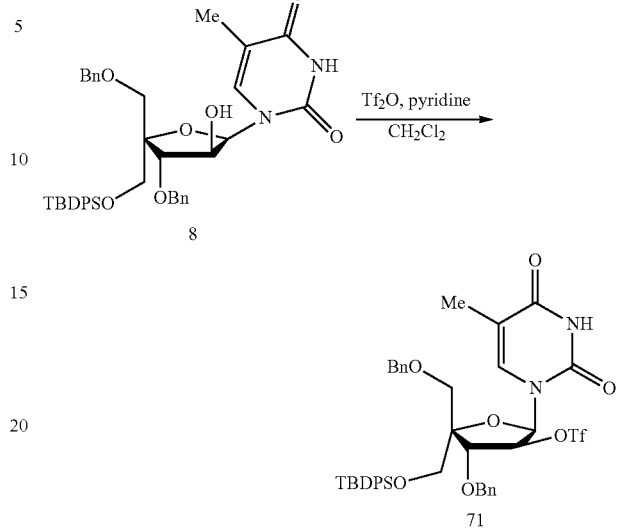

The solution of compound 8 (3 μm, 4.24 mmol) in dichloromethane (15 mL) was mixed with pyridine (1.5 mL, 8.48 mmol) and trifluoromethanesulfonic anhydride (0.7 mL, 2.828 mmol) at 0° C. and stirred for 40 minutes on ice cooling. After ice-cold water was added to the mixture which was then extracted with dichloromethane, the organic layer was washed with water and saturated saline and dried over sodium sulfate. After the solvent was distilled away, the resultant compound 71 (4.64 g) was used for the next reaction.

(2) Synthesis of Compound 72

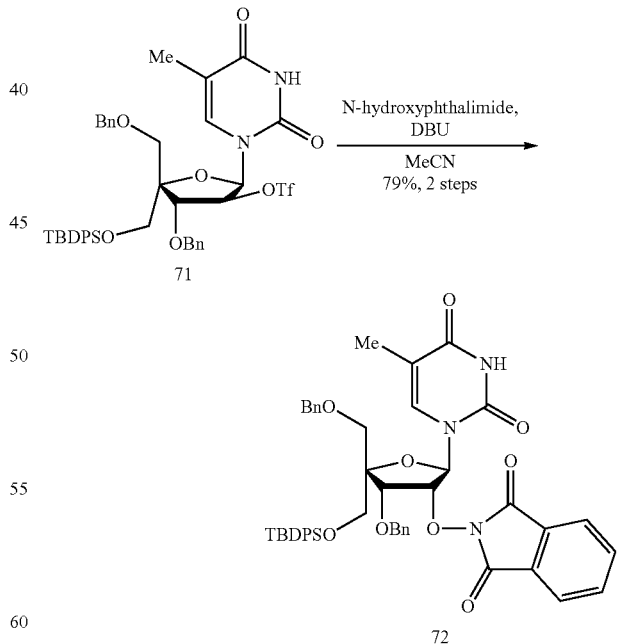

To a solution of compound 71 from (1) above in acetonitrile (20 mL) was added N-hydroxyphthalimide (4.5 mg, 27.66 mmol) and 1,8-diazabicyclo[5.4.0]-7-undecene (4.2 mL, 27.66 mmol) and the mixture was stirred for 24 hours at room temperature. After dilution with dichloromethane and addition of water, the mixture was extracted with dichloromethane. The organic layer was washed with water and saturated saline and then dried over sodium sulfate. After the solvent was distilled away, the resultant crude product was purified by column chromatography (n-hexane:ethyl acetate=2:1) to give compound 72 (2.88 g:yield 79% (2 steps)) as a white foamy solid.

The physical property data of the resultant compound 72 was as follows: $[\alpha]_D^{25}$=+43.0 (c 1.00, CHCl$_3$); IR $v_{max}$ (KBr): 3188, 3067, 2934, 2862, 1791, 1730, 1692, 1465, 1427, 1421, 1366, 1267, 1189, 1106, 973 cm$^{-1}$; $^1$H-NMR (400 MHz, CDCl$_3$): d$_H$ 1.08 (9H, s), 1.38 (3H, s), 3.65 (1H, d, J=10.4 Hz), 4.02 (1H, d, J=11.6 Hz), 4.09 (1H, d, J=10.4 Hz), 4.22 (1H, d, J=11.6 Hz), 4.48 (1H, d, J=11.2 Hz), 4.52 (1H, d, J=5.2 Hz), 4.55 (1H, d, J=11.2 Hz), 4.73 (1H, d, J=11.2 Hz), 4.85 (1H, dd, J=3.2 Hz, 2.8 Hz), 5.13 (1H, d, J=11.2 Hz), 6.40 (1H, d, J=3.2 Hz), 7.16-7.86 (26H, m).

(3) Synthesis of Compound 73

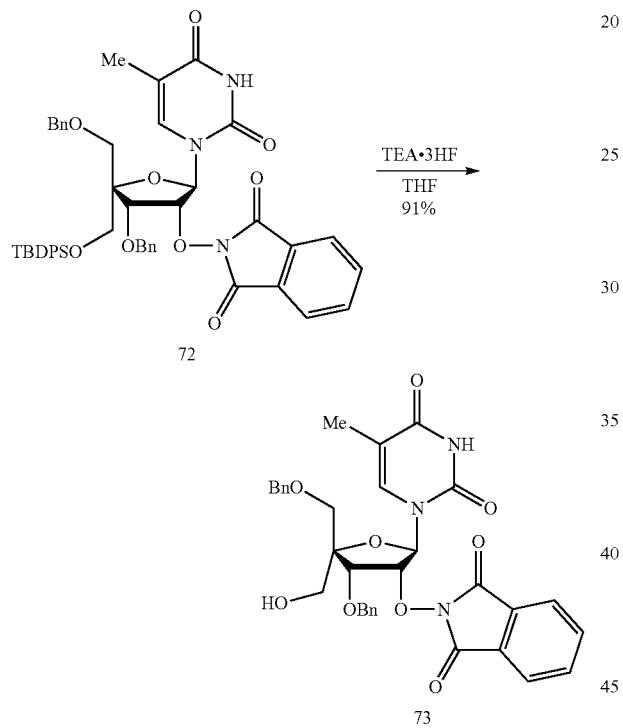

To a solution of compound 72 from (2) above (2.88 g, 3.38 mmol) in tetrahydrofuran (15 mL) was added triethylamine trihydrofluoride (5.6 mL, 33.8 mmol) and the mixture was refluxed for 18 hours at 70° C. Ice-cold water was added to the reactant on ice cooling, which was then extracted with ethyl acetate, followed by the extract washed with saturated sodium bicarbonate solution and saturated saline and then dried over sodium sulfate. After the solvent was distilled away, the resultant crude product was purified by column chromatography (n-hexane:ethyl acetate=1:1) to give compound 73 (1.89 g:yield 91%) as a white foamy solid.

The physical property data of the resultant compound 73 was as follows: $[\alpha]_D^{25}$=+39.1 (c 1.00, CHCl$_3$); IR $v_{max}$ (KBr): 3504, 3181, 3062, 2881, 1789, 1733, 1689, 1466, 1375, 1272, 1187, 1105, 1057, 974 cm$^{-1}$; $^1$H-NMR (400 MHz, CDCl$_3$): d$_H$ 1.36 (3H, s), 3.84 (1H, d, J=10.4 Hz), 3.92 (1H, d, J=7.2 Hz), 3.96 (1H, d, J=10.4 Hz), 4.12 (1H, d, J=7.2 Hz), 4.49 (1H, d, J=11.2 Hz), 4.54 (1H, d, J=11.2 Hz), 4.63 (1H, d, J=6 Hz), 4.74 (1H, d, J=12 Hz), 4.93 (1H, dd, J=6 Hz, 1.6 Hz), 5.16 (1H, d, J=11.6 Hz), 6.35 (1H, d, J=1.2 Hz), 7.15-7.87 (15H, m), 7.92 (1H, br s).

(4) Synthesis of Compound 74

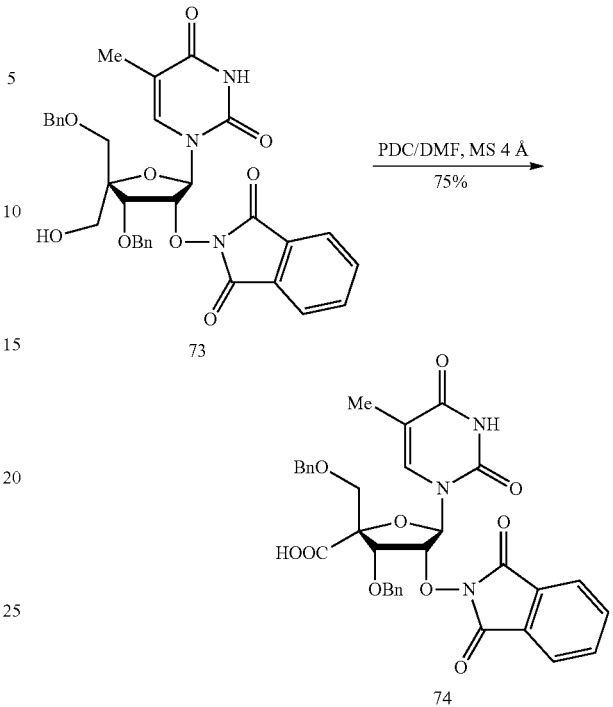

To a solution of compound 73 from (3) above in N,N-dimethylformamide (20 mL) was added molecular sieves 4 Å (2 g) and the mixture was stirred for 10 minutes. Pyridinium dichromate (11.6 g, 30.8 mmol) was added to the reactant which was then stirred for 16 hours at room temperature. Ice-cold water and acetic acid (2 mL) was added to the reactant which was then stirred. The product was extracted with ethyl acetate, which was then purified by column chromatography (n-hexane:ethyl acetate=1:1→ethyl acetate:methanol=10:1) to give compound 74 (1.44 g:yield 75%) as a white foamy solid.

The physical property data of the resultant compound 74 was as follows: $[\alpha]_D^{26}$=+23.9 (c 1.00, CHCl$_3$); IR $v_{max}$ (KBr): 3178, 3066, 3032, 2873, 1790, 1736, 1468, 1376, 1275, 1187, 1125, 967 cm$^{-1}$; $^1$H-NMR (400 MHz, CDCl$_3$): d$_H$ 1.59 (3H, s), 3.90 (1H, d, J=10.4 Hz), 4.11 (1H, d, J=10.4 Hz), 4.59 (1H, d, J=11.6 Hz), 4.63 (1H, d, J=11.6 Hz), 4.68 (1H, d, J=4.4 Hz), 4.91 (1H, d, J=11.2 Hz), 5.05 (1H, t, J=5.6 Hz) 5.27 (1H, d, J=11.2 Hz), 6.70 (1H, d, J=6.4 Hz), 7.32-7.86 (16H, m), 8.75 (1H, br s).

(5) Synthesis of Compound 75

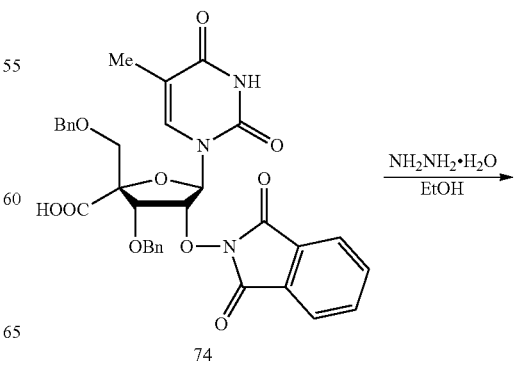

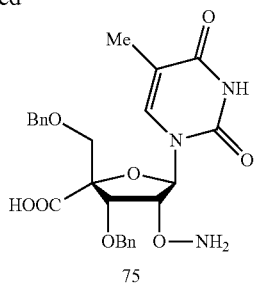

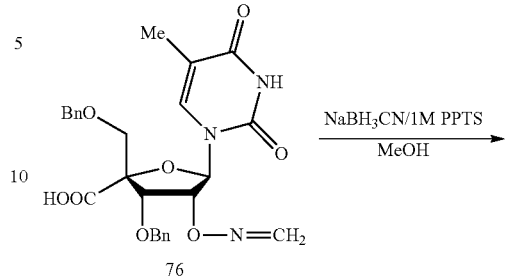

To a solution of compound 74 from (4) above (400 mg, 0.636 mmol) in ethanol (2 mL) was added hydrazine monohydrate (0.04 mL, 1.02 mmol) and the mixture was stirred for 10 minutes at room temperature. The solvent was distilled away from the reactant to which ethyl acetate was then added. After the residue was filtered and the filtrate was extracted with ethyl acetate, followed by the extract washed with water and saturated saline, the solvent was distilled away to give the resultant compound 75 (380 mg) which was then used for the next reaction.

(6) Synthesis of Compound 76

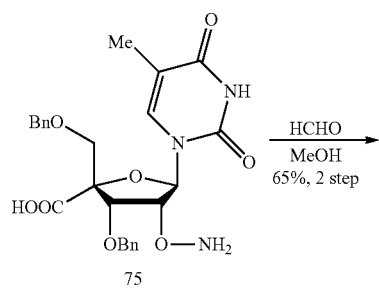

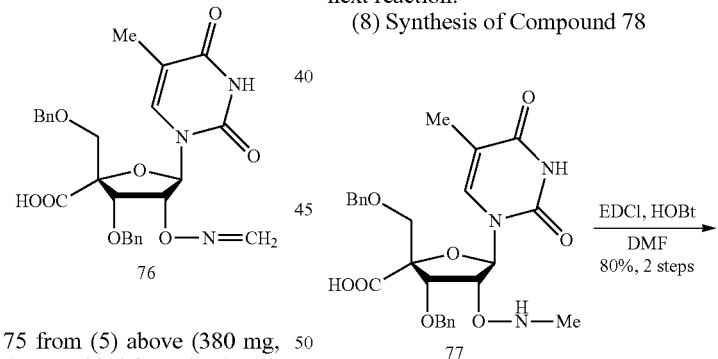

To a solution of compound 75 from (5) above (380 mg, 0.763 mmol) in methanol (5 mL) was added formalin (37 wt % in H$_2$O, 0.08 mL, 0.840 mmol). After the reactant was stirred for 2 hours at room temperature, the solvent was distilled away. Water was added to the residue, which was then extracted with ethyl acetate, followed by the extract washed with water and saturated saline and then dried over sodium sulfate. After the solvent was distilled away, the residue was purified by column chromatography (n-hexane:ethyl acetate=1:1→1:2) to give the resultant compound 76 (250 mg:yield 65% (2 steps)) as a white solid.

The physical property data of the resultant compound 76 was as follows: $[\alpha]_D^{26}$=−29.3 (c 1.00, CHCl$_3$); IR $v_{max}$ (KBr): 3172, 3064, 2944, 2872, 1699, 1469, 1366, 1274, 1127, 1070, 916 cm$^{-1}$; $^1$H-NMR (400 MHz, CDCl$_3$): d$_H$ 1.56 (3H, s), 3.84 (1H, d, J=10.4 Hz), 4.14 (1H, d, J=10.4 Hz), 4.64-4.79 (6H, m), 5.11 (1H, dd, J=4.6 Hz, 3.2 Hz), 6.59 (1H, d, J=6.8 Hz), 7.28-7.64 (11H, m).

(7) Synthesis of Compound 77

To a solution of compound 76 from (6) above (250 mg, 0.491 mmol) in methanol was added p-pyridinium toluenesulfonate (1 M, 4.9 mL, 4.91 mmol) and sodium cyanoborohydride (62 mg, 0.982 mmol) and the mixture was then stirred for 10 minutes at 0° C. The reactant was warmed to room temperature and stirred for further 2 hours. After the solvent was distilled away, the resultant product was diluted with ethyl acetate, washed with water and saturated saline and then dried over sodium sulfate. After the solvent was distilled away, the resultant compound 77 (235 mg) was used for the next reaction.

(8) Synthesis of Compound 78

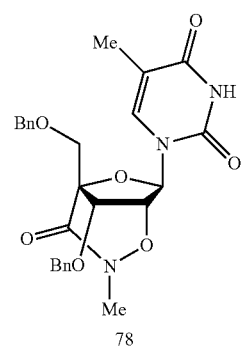

To a solution of compound 77 from (7) (235 mg, 0.459 mmol) in N,N-dimethylformamide (4 mL) was added 1-ethyl-3-(3-dimethylaminopropyl) carbodiimide hydrochloride (105.5 mg, 0.551 mmol) and 1-hydroxybenzotriazole (74.5 mg, 0.551 mmol) and the mixture was stirred for one day at room temperature. After adding the water, the mixture was extracted with ethyl acetate, followed by the extract washed with water and saturated saline and then dried over sodium sulfate. After the solvent was distilled away, the resultant crude product was purified by column chromatography (n-hexane:ethyl acetate=4:1→1:1) to give compound 78 (190 mg:yield 80% (2 steps)) as a white solid.

The physical property data of the resultant compound 78 was as follows: $[\alpha]_D^{26}$=+62.3 (c 1.00, CHCl$_3$); IR $\nu_{max}$ (KBr): 3164, 3029, 2926, 2878, 1698, 1456, 1392, 1362, 1274, 1215, 1155, 1094, 1065, 983 cm$^{-1}$; $^1$H-NMR (400 MHz, CDCl$_3$): $d_H$ 1.42 (3H, s), 3.25 (3H, s), 3.95 (1H, d, J=11.6 Hz), 4.25 (1H, d, J=11.6 Hz), 4.34 (1H, d, J=3.2 Hz), 4.56 (1H, d, J=10.8 Hz), 4.59-4.64 (3H, m), 4.73 (1H, d, J=10.8 Hz), 6.08 (1H, s), 7.23-7.37 (10H, m), 7.62 (1H, d, J=1.6 Hz).

(9) Synthesis of Compound 79

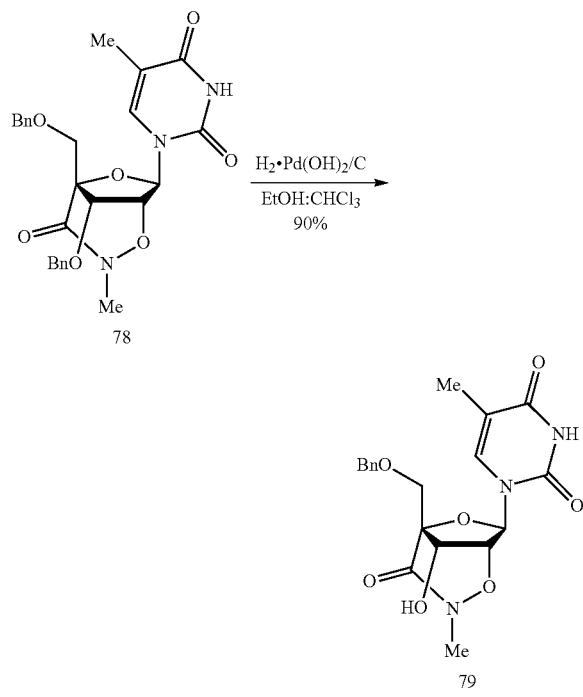

To a solution of compound 78 from (8) above (190 mg, 0.385 mmol) in ethanol:chloroform=5:1 (5 mL) was added palladium hydroxide on carbon (190 mg) and the mixture was stirred. After several replacements with hydrogen gas were performed in the reaction container, the content was stirred overnight at room temperature under hydrogen stream. After filtration of the solution, the solvent was distilled away and the resultant crude product was purified by column chromatography (n-hexane:ethyl acetate=1:1-400% ethyl acetate) to give compound 79 (105 mg:yield 90%) as a white solid.

The physical property data of the resultant compound 79 was as follows: $[\alpha]_D^{26}$=+14.9 (c 1.00, CHCl$_3$); IR $\nu_{max}$ (KBr): 3444, 3226, 3070, 2941, 1678, 1469, 1412, 1281, 1199, 1078, 988 cm$^{-1}$; $^1$H-NMR (400 MHz, CD$_3$OD): $d_H$ 1.88 (3H, s), 3.25 (3H, s), 3.90 (1H, d, J=12.8 Hz), 4.22 (1H, d, J=12.8 Hz), 4.55 (1H, J=3.6 Hz), 4.73 (1H, J=3.6 Hz), 6.08 (1H, s), 7.98 (1H, d, J=1.2 Hz).

(10) Synthesis of Compound 80

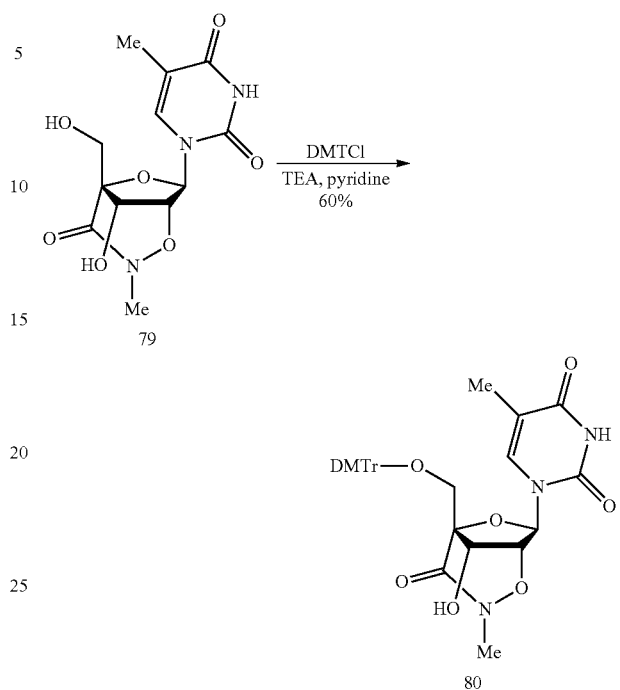

To a solution of compound 79 from (9) above (50 mg, 0.159 mmol) in pyridine (3 mL) was added 4,4'-dimethoxytrityl chloride (65 mg, 0.191 mmol) and triethylamine (0.1 mL, 0.795 mmol) and the mixture was stirred for 8 hours at room temperature. On ice cooling saturated sodium bicarbonate solution was added to the mixture which was then extracted with ethyl acetate, and the organic layer was washed with water and saturated saline and then dried over sodium sulfate. After the solvent was distilled away, the resultant product was purified by column chromatography (1% triethylamine-added n-hexane:ethyl acetate=2:1→100% ethyl acetate) to give compound 80 (58 mg:yield 60%) as a light yellow solid.

The physical property data of the resultant compound 80 was as follows: $[\alpha]_D^{28}$=-21.1 (c 1.00, CHCl$_3$); IR $\nu_{max}$ (KBr): 3339, 3189, 3062, 2926, 2850, 1693, 1608, 1509, 1464, 1395, 1253, 1177, 1080, 1033, 978 cm$^{-1}$; $^1$H-NMR (400 MHz, CDCl$_3$): $d_H$ 1.41 (3H, s), 3.22 (3H, s), 3.72 (1H, d, J=12 Hz), 3.78 (6H, s), 3.97 (1H, d, J=12 Hz), 4.69 (1H, d, J=3.6 Hz), 4.72 (1H, d, J=3.6 Hz), 6.05 (1H, s), 6.82-6.85 (4H, m), 7.25-7.42 (9H, m), 7.67 (1H, s).

(11) Synthesis of Compound 81

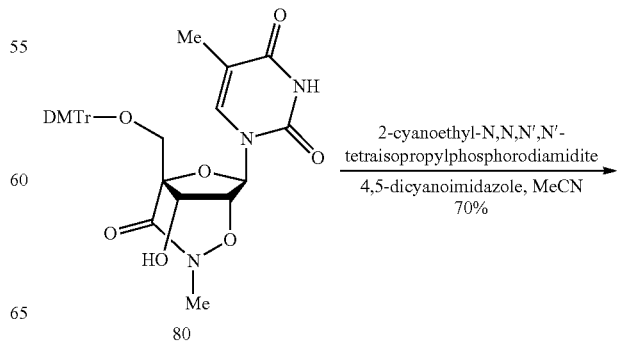

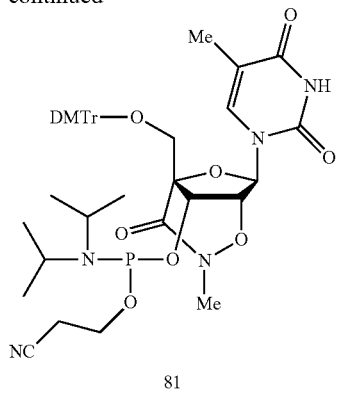

81

To a solution of compound 80 from (36) above (50 mg, 0.08 mmol) in anhydrous acetonitrile was added 2-cyanoethyl-N,N,N',N'-tetraisopropyl phosphoramidite (0.04 mL, 0.138 mmol) and 4,5-dicyanoimidazole (9.5 mg, 0.08 mmol) and the mixture was then stirred for 7 hours at room temperature. After the reaction, saturated sodium bicarbonate solution was added to the reactant which was then extracted with ethyl acetate. The organic layer was washed with water and saturated saline and then dried over sodium sulfate. After the solvent was distilled away, the resultant crude product was purified by column chromatography (1% triethylamine-added n-hexane:ethyl acetate=2:1-4:1) to give compound 81 (46 mg, 70%) as a white solid.

The physical property data of the resultant compound 81 was as follows: $^{31}$P-NMR (100 MHz, CDCl$_3$): d$_P$ 151.23, 151.82.

Example 16

Synthesis and Purification of the Oligonucleotide Analogues

10mer of the oligonucleotide analogues containing compound 81 (amidite) from Example 15 above (compounds 82-85: showed in Table 8 below) were synthesized using Expedite™ 8909 (from ABI) in the scale of 0.2 µmol. This synthesis was carried out according to the standard phosphoramidite protocol and the compound 81 (amidite unit) was dissolved in acetonitrile to use in the synthesis. In Table 8, the compound 81 is indicated by X. Duration of the coupling reaction between an amidite unit (compound 81) and a hydroxyl group at 5'-terminus was extended from 1.5 minutes (standard condition) to 30 minutes. The oligonucleotide analogues with the 5'-terminus protected with a DMTr group supported on a solid phase were treated with 0.05 M solution of potassium carbonate in methanol and then neutralized with 1.0 M TEAA (triethylamine monoacetate), after which the solvent was distilled away. The resultant crude product was partially purified by the gel filtration column NAP™ 10 Column (GE Health Care) and then purified by reversed-phase HPLC(SHIMADZU LC-10AT$_{VP}$, SHIMADZU SPD-10A$_{VP}$, SHIMADZU CTO-10$_{VP}$, using WatersXBridge™ OST C$_{18}$ 2.5 µm (10 mm×50 mm) as a preparative column).

The purities of the synthesized oligonucleotide analogues (compounds 82-85) were determined using reversed-phase HPLC (WatersXBridge™ Shield RP18 2.5 µm (4.6 mm×50 mm) (condition: gradient 5→14% (v/v) acetonitrile in 0.1 M triethyl ammonium acetate buffer (pH 7.0), 1 mL/min for 30 minutes). The molecular weights were determined by MALDI-TOF-MASS. The results are shown in Table 8.

TABLE 8

| Oligonucleotide | | MALDI-TOF-MASS | |
|---|---|---|---|
| | | Calculated (M − H$^-$) | Found (M − H$^-$) |
| 5'-TTTTTXTTTT-3' | (Compound 82) | 3048.50 | 3049.40 |
| 5'-TTTXTXTTTT-3' | (Compound 83) | 3119.51 | 3120.71 |
| 5'-TTTXTXTXTT-3' | (Compound 84) | 3190.10 | 3191.50 |
| 5'-TTTTTTTTXT-3' | (Compound 85) | 3048.50 | 3049.21 |

Example 17

Determination of the Melting Temperature (Tm)

After compounds 82-84 (antisense strands), which were the oligonucleotide strands synthesized in Example 16 above, and sense strands (3'-AAAAAAAAAA-5') were subjected to an annealing treatment, their Tm values were measured to determine the hybridization ability of the antisense strands.

The sample solution (130 µL) containing 100 mM NaCl, 10 mM sodium phosphate buffer (pH 7.2), 4 µM antisense strands and 4 µM sense strands was heated in a boiled water bath and then cooled to room temperature over 10 hours. Nitrogen stream was passed into a cell chamber of a spectrophotometer (Shimadzu, UV-1650PC) for dew condensation prevention, and the sample solution was gradually cooled to 5° C. and kept at 10° C. for 20 minutes before starting the measurements. The temperature was raised to 85° C. at the rate of 0.5° C./min while ultraviolet absorption spectra were measured at 260 nm at intervals of 0.1° C. Lidded cells were used to prevent concentration change due to rising temperature. The results are shown in Table 9.

TABLE 9

| | | Sense strand | | | |
|---|---|---|---|---|---|
| | | RNA complementary strand | | DNA complementary strand | |
| Antisense strand | | Tm (° C.) | Δ Tm/mod. (° C.) | Tm (° C.) | Δ Tm/mod. (° C.) |
| 5'-TTTTTTTTTT-3' | (Compound 21) | 18.2 | | 19.7 | |
| 5'-TTTTTXTTTT-3' | (Compound 82) | 19.8 | +3.3 | 11.5 | −7.3 |

TABLE 9-continued

| Antisense strand | Sense strand | | | |
|---|---|---|---|---|
| | RNA complementary strand | | DNA complementary strand | |
| | Tm (° C.) | Δ Tm/mod. (° C.) | Tm (° C.) | Δ Tm/mod. (° C.) |
| 5'-TTTXTXTTTT-3' (Compound 83) | 25.0 | +3.4 | 14.6 | -2.5 |
| 5'-TTTXTXTXTT-3' (Compound 84) | 29.1 | +3.6 | 22.7 | +1.0 |

Δ Tm/mod. = Δ Tm/modified base

As shown in Table 9, the oligonucleotide analogues of the invention have higher affinities to single-stranded RNAs than to single-stranded DNAs and the more artificial nucleic acids introduced into an oligonucleotide, the higher Tm value it has. Therefore, the nucleotide analogues of the invention are believed to be useful for the synthesis of the oligonucleotides suitable for antisense therapies.

Industrial Applicability

According to the present invention, the novel 2',4'-bridged artificial nucleosides and nucleotides with a bridging containing an amide bond are provided. An oligonucleotide containing the 2',4'-bridged artificial nucleotide has a good binding affinity for a single-stranded RNA comparable to that of publicly known 2',4'-BNA/LNA and a stronger nuclease resistance than LNA. Since the binding affinity of the aforementioned oligonucleotide to a single-stranded RNA is much higher than that of S-oligo, it is expected that the oligonucleotides are applicable to nucleic acid drugs.

The invention claimed is:

1. A compound represented by the following formula I or formula II or a salt thereof:

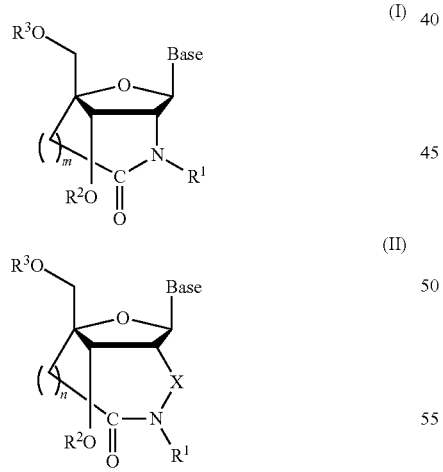

wherein,

Base represents a purin-9-yl group or a 2-oxo-1,2-dihydropyrimidin-1-yl group that may have any one or more substituents selected from group α, wherein the group α consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, or a protecting group for an amino group on nucleic acid synthesis;

$R^2$ and $R^3$ represents, each independently, a hydrogen atom, a protecting group for a hydroxyl group on nucleic acid synthesis, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group α and may contain heteroatoms, an aralkyl group with an aryl moiety having 3 to 12 carbon atoms that may have any one or more substituents selected from the group α and may contain heteroatoms, an acyl group that may have any one or more substituents selected from the group α, a silyl group that may have any one or more substituents selected from the group α, a phosphate group that may have any one or more substituents selected from the group α, a phosphate group protected with a protecting group for nucleic acid synthesis, —P($R^4$)$R^5$ (wherein $R^4$ and $R^5$ represent, each independently, a hydroxyl group, a hydroxyl group protected with a protecting group for nucleic acid synthesis, a mercapto group, a mercapto group protected with a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms or an amino group substituted with an alkyl group having 1 to 6 carbon atoms.);

X represents an oxygen atom, a sulfur atom, an amino group or a methylene group;

m is an integer from 0 to 2; and n is an integer from 0 to 1.

2. The compound or salt thereof according to claim 1, wherein the Base in the formula I or formula II is a 6-aminopurin-9-yl group, a 2,6-diaminopurin-9-yl group, a 2-amino-6-chloropurin-9-yl group, a 2-amino-6-fluoropurin- 9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2,6-dichloropurin-9-yl group, a 6-mercaptopurin-9-yl group, a 2-oxo-4-amino-1,2-dihydropyrimidin-1-yl group, a 4-amino-2-oxo-5-fluoro-1,2-dihydropyrimidin-1-yl group, a 4-amino-2-oxo-5-chloro-1,2-dihydropyrimidin-1-yl group, a 2-oxo-4-methoxy-1,2-dihydropyrimidin-1-yl group, a 2-oxo-4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group or a 4-amino-5-methyl-2-oxo-1,2-dihydropyrimidin-1-yl group.

3. The compound or salt thereof according to claim 1, wherein the $R^1$ in the formula I or formula II is a hydrogen atom, a methyl group, an ethyl group, an n-propyl group, an isopropyl group, a phenyl group or a benzyl group.

4. The compound or salt thereof according to claim 1, wherein the m in the formula I is 0.

5. The compound or salt thereof according to claim 1, wherein the n in the formula II is 0.

6. The compound or salt thereof according to claim 1, wherein the Base in the formula I or formula II is a 2-oxo-4-hydroxy-5-methyl-1,2-dihydropyrimidin-1-yl group.

7. An oligonucleotide containing at least one nucleoside structure represented by the following formula III or formula IV or pharmacologically acceptable salts thereof:

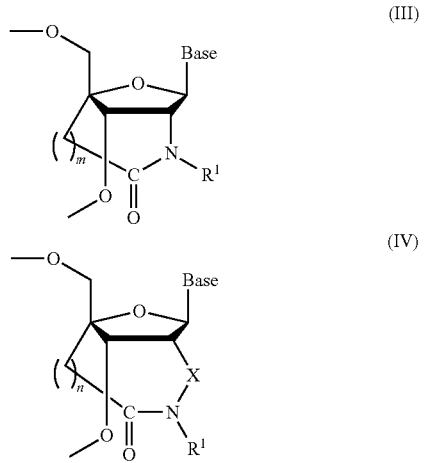

wherein

Base represents a purin-9-yl group or a 2-oxo-1,2-dihydropyrimidin-1-yl group that may have any one or more substituents selected from group α, wherein the group α consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group a and may contain heteroatoms, an aralkyl group with an aryl moiety having 3 to 12 carbon atoms that may have any one or more substituents selected from the group α and may contain heteroatoms, or a protecting group for an amino group on nucleic acid synthesis;

X represents an oxygen atom, a sulfur atom, an amino group or a methylene group;

m is an integer from 0 to 2; and n is an integer from 0 to 1.

8. The compound or salt thereof according to claim 2, wherein the $R^1$ in the formula I or formula II is a hydrogen atom, a methyl group, an ethyl group, an n-propyl group, an isopropyl group, a phenyl group or a benzyl group.

9. The compound or salt thereof according to claim 2, wherein the m in the formula I is 0.

10. The compound or salt thereof according to claim 3, wherein the m in the formula I is 0.

11. The compound or salt thereof according to claim 2, wherein the n in the formula II is 0.

12. The compound or salt thereof according to claim 3, wherein the n in the formula II is 0.

13. The compound or salt thereof according to claim 2, wherein the Base in the formula I or formula II is a 2-oxo-4-hydroxy-5-methyl-1,2-dihydropyrimidin-1-yl group.

14. The compound or salt thereof according to claim 3, wherein the Base in the formula I or formula II is a 2-oxo-4-hydroxy-5-methyl-1,2-dihydropyrimidin-1-yl group.

15. The compound or salt thereof according to claim 4, wherein the Base in the formula I or formula II is a 2-oxo-4-hydroxy-5-methyl-1,2-dihydropyrimidin-1-yl group.

16. The compound or salt thereof according to claim 5, wherein the Base in the formula I or formula II is a 2-oxo-4-hydroxy-5-methyl-1,2-dihydropyrimidin-1-yl group.

17. The compound or salt thereof according to claim 8, wherein the m in the formula I is 0.

18. The compound or salt thereof according to claim 8, wherein the n in the formula II is 0.

19. The compound or salt thereof according to claim 8, wherein the Base in the formula I or formula II is a 2-oxo-4-hydroxy-5-methyl-1,2-dihydropyrimidin-1-yl group.

* * * * *

UNITED STATES PATENT AND TRADEMARK OFFICE
CERTIFICATE OF CORRECTION

PATENT NO.         : 8,541,562 B2
APPLICATION NO.    : 13/502611
DATED              : September 24, 2013
INVENTOR(S)        : Satoshi Obika et al.

It is certified that error appears in the above-identified patent and that said Letters Patent is hereby corrected as shown below:

In the Drawings

Drawing Sheet should consist of label -- "FIG. 1"

In the Specifications

Examples, col 14, line 6 should read -- "5'-O-dimethoxytrityl-2'-N,4'-C-oxomethylene thymi-"

Examples, col 25, line 66 should read -- "(1H,s), 6.86-7.45 (13H, m), 7.78 (1H,s); MS (FAB): m/z 586"

Signed and Sealed this
First Day of April, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,541,562 C1
APPLICATION NO. : 90/013257
DATED : August 21, 2014
INVENTOR(S) : Satoshi Obika et al.

It is certified that error appears in the above-identified patent and that said Letters Patent is hereby corrected as shown below:

In the Specification

Ex Parte Reexamination Certificate, col 1, line 23 should read -- "formula II or a salt thereof:"

Ex Parte Reexamination Certificate, col 1, line 48 should read -- "substituents selected from group α, wherein the group α"

Ex Parte Reexamination Certificate, col 1, line 64 should read -- "more substituents selected from the group α and may"

Ex Parte Reexamination Certificate, col 1, line 67 should read -- "or more substituents selected from the group α and may"

Ex Parte Reexamination Certificate, col 2, line 10 should read -- "ents selected from the group α and may contain heteroa-"

Ex Parte Reexamination Certificate, col 2, line 13 should read -- "ents selected from the group α and may contain heteroa-"

Ex Parte Reexamination Certificate, col 2, line 15 should read -- "substituents selected from the group α, a silyl group that"

Ex Parte Reexamination Certificate, col 2, line 17 should read -- "group α, a phosphate group that may have any one or"

Ex Parte Reexamination Certificate, col 2, line 18 should read -- "more substituents selected from the group α, a phosphate"

Signed and Sealed this
Third Day of February, 2015

Michelle K. Lee
*Deputy Director of the United States Patent and Trademark Office*

CERTIFICATE OF CORRECTION (continued)
U.S. Pat. No. 8,541,562 C1

Ex Parte Reexamination Certificate, col 2, line 61 should read -- "substituents selected from group α, wherein the group α"

(12) EX PARTE REEXAMINATION CERTIFICATE (10266th)
United States Patent
Obika et al.

(10) Number: US 8,541,562 C1
(45) Certificate Issued: Aug. 21, 2014

(54) BRIDGED ARTIFICIAL NUCLEOSIDE AND NUCLEOTIDE

(75) Inventors: Satoshi Obika, Osaka (JP); Yoshiyuki Hari, Osaka (JP); Tetsuya Kodama, Osaka (JP); Aiko Yahara, Osaka (JP); Masaru Nishida, Osaka (JP)

(73) Assignee: Osaka University, Yamadaoka, Suita-Shi, Osaka (JP)

Reexamination Request:
No. 90/013,257, Jun. 3, 2014

Reexamination Certificate for:
Patent No.: 8,541,562
Issued: Sep. 24, 2013
Appl. No.: 13/502,611
Filed: Apr. 18, 2012

Certificate of Correction issued Apr. 1, 2014

(21) Appl. No.: 90/013,257
(22) PCT Filed: Oct. 19, 2010
(86) PCT No.: PCT/JP2010/068409
§ 371 (c)(1), (2), (4) Date: Apr. 18, 2012
(87) PCT Pub. No.: WO2011/052436
PCT Pub. Date: May 5, 2011

(30) Foreign Application Priority Data

Oct. 29, 2009 (JP) .................................. 2009-248979
Feb. 4, 2010 (JP) .................................. 2010-023209

(51) Int. Cl.
*C07H 21/02* (2006.01)
*C07H 19/02* (2006.01)
*C07H 19/00* (2006.01)

(52) U.S. Cl.
USPC ........................ 536/23.1; 536/28.1; 536/27.1

(58) Field of Classification Search
None
See application file for complete search history.

(56) References Cited

To view the complete listing of prior art documents cited during the proceeding for Reexamination Control Number 90/013,257, please refer to the USPTO's public Patent Application Information Retrieval (PAIR) system under the Display References tab.

*Primary Examiner* — Alan Diamond

(57) ABSTRACT

It is an object of the present invention to provide a novel molecule for antisense therapies which is not susceptible to nuclease degradation in vivo and has a high binding affinity and specificity for the target mRNAs and which can efficiently regulate expression of specific genes. The novel artificial nucleoside of the present invention has an amide bond introduced into a bridge structure of 2',4'-BNA/LNA. The oligonucleotide containing the 2',4'-bridged artificial nucleotide has a binding affinity for a single-stranded RNA comparable to known 2',4'-BNA/LNA and has an increased nuclease resistance over LNA. Particularly, it is expected to be applied to nucleic acid drugs because of its much stronger binding affinity for single-stranded RNAs than S-oligo's affinity.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1 and 7 are determined to be patentable as amended.

Claims 2-6 and 8-19 were not reexamined.

1. A compound represented by the following formula I or formula II or a salt thereof.

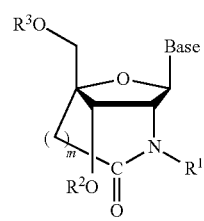

(I)

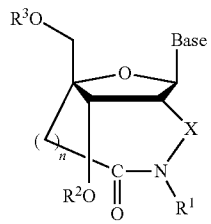

(II)

wherein,
Base represents a purin-9-yl group or a 2-oxo-1,2-dihydropyrimidin-1-yl group that may have any one or more substituents selected from group a, wherein the group a consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group a and may contain heteroatoms, an aralkyl group with an aryl moiety having 3 to 12 carbon atoms that may have any one or more substituents selected from the group a and may contain heteroatoms, or a protecting group for an amino group on nucleic acid synthesis;

$R^2$ and $R^3$ represents, each independently, a hydrogen atom, a protecting group for a hydroxyl group on nucleic acid synthesis, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group a and may contain heteroatoms, an aralkyl group with an aryl moiety having 3 to 12 carbon atoms that may have any one or more substituents selected from the group a and may contain heteroatoms, an acyl group that may have any one or more substituents selected from the group a, a silyl group that may have any one or more substituents selected from the group a, a phosphate group that may have any one or more substituents selected from the group a, a phosphate group protected with a protecting group for nucleic acid synthesis, $—P(R^4)R^5$ (wherein $R^4$ and $R^5$ represent, each independently, a hydroxyl group, a hydroxyl group protected with a protecting group for nucleic acid synthesis, a mercapto group, a mercapto group protected with a protecting group for nucleic acid synthesis, an amino group, an alkoxy group having 1 to 5 carbon atoms, an alkylthio group having 1 to 5 carbon atoms, an cyanoalkoxy group having 1 to 6 carbon atoms or an amino group substituted with an alkyl group having 1 to 6 carbon atoms.);

X represents an oxygen atom, a sulfur atom, *or* an amino group [or a methylene group];
m is an integer from 0 to 2; and
n is an integer from 0 to 1.

7. An oligonucleotide containing at least one nucleoside structure represented by the following formula III or formula IV or pharmacologically acceptable salts thereof:

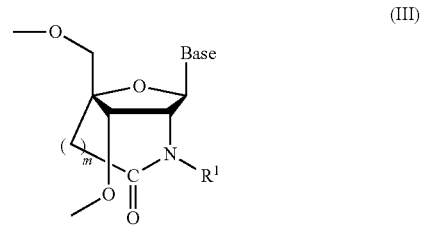

(III)

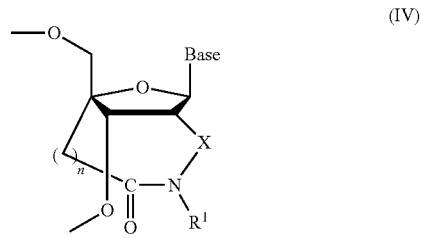

(IV)

wherein
Base represents a purin-9-yl group or a 2-oxo-1,2-dihydropyrimidin-1-yl group that may have any one or more substituents selected from group a, wherein the group a consists of a hydroxyl group, a hydroxyl group protected with a protecting group for nucleic acid synthesis, linear alkyl groups having 1 to 6 carbon atoms, linear alkoxy groups having 1 to 6 carbon atoms, a mercapto group, a mercapto group protected with a protecting group for nucleic acid synthesis, linear alkylthio groups having 1 to 6 carbon atoms, an amino group, linear alkylamino groups having 1 to 6 carbon atoms, an amino group protected with a protecting group for nucleic acid synthesis and halogen atoms;

$R^1$ represents a hydrogen atom, an alkyl group having 1 to 7 carbon atoms that may be branched or form a cyclic group, an alkenyl group having 2 to 7 carbon atoms that may be branched or form a cyclic group, an aryl group having 3 to 12 carbon atoms that may have any one or more substituents selected from the group [a] *a* and may contain heteroatoms, an aralkyl group with an aryl moiety having 3 to 12 carbon atoms that may have any one or more substituents selected from the group a and may contain heteroatoms, or a protecting group for an amino group on nucleic acid synthesis;

X represents an oxygen atom, a sulfur atom, *or* an amino group [or a methylene group];

m is an integer from 0 to 2; and n is an integer from 0 to 1.

\* \* \* \* \*